US008865758B2

(12) United States Patent
Page et al.

(10) Patent No.: US 8,865,758 B2
(45) Date of Patent: *Oct. 21, 2014

(54) PYRAZOLO PIPERIDINE DERIVATIVES AS NADPH OXIDASE INHIBITORS

(75) Inventors: Patrick Page, Saint-Julien-en-Genevois (FR); Benoît Laleu, Collonges-sous-Salève (FR); Francesca Gaggini, Geneva (CH); Mike Orchard, Oxon (GB)

(73) Assignee: Genkyotex SA, Plan-les-Ouates (CH)

( * ) Notice: Subject to any disclaimer, the term of this patent is extended or adjusted under 35 U.S.C. 154(b) by 0 days.

This patent is subject to a terminal disclaimer.

(21) Appl. No.: 13/579,290

(22) PCT Filed: Feb. 17, 2011

(86) PCT No.: PCT/IB2011/050667
§ 371 (c)(1),
(2), (4) Date: Aug. 16, 2012

(87) PCT Pub. No.: WO2011/101804
PCT Pub. Date: Aug. 25, 2011

(65) Prior Publication Data
US 2012/0316163 A1 Dec. 13, 2012

(30) Foreign Application Priority Data

Feb. 18, 2010 (EP) .................................. 10153927

(51) Int. Cl.
A01N 43/56 (2006.01)
A61K 31/415 (2006.01)
C07D 231/56 (2006.01)
C07D 231/54 (2006.01)
C07D 487/00 (2006.01)
C07D 513/02 (2006.01)
C07D 515/02 (2006.01)
A61K 9/00 (2006.01)
C07D 471/04 (2006.01)

(52) U.S. Cl.
CPC .................................. C07D 471/04 (2013.01)
USPC ......... 514/405; 548/363.1; 546/118; 424/400

(58) Field of Classification Search
CPC ........................... C07D 401/04; C07D 471/04
USPC ......... 548/363.1; 546/118; 424/400; 514/405
See application file for complete search history.

(56) References Cited

U.S. PATENT DOCUMENTS

| 6,107,306 | A | 8/2000 | Carpino et al. |
| 8,288,432 | B2 | 10/2012 | Page et al. |
| 8,389,518 | B2 | 3/2013 | Page et al. |
| 8,455,485 | B2 | 6/2013 | Page et al. |
| 8,455,486 | B2 | 6/2013 | Page et al. |
| 8,481,562 | B2 | 7/2013 | Page et al. |
| 2010/0048560 | A1 | 2/2010 | Page et al. |
| 2010/0120749 | A1 | 5/2010 | Page et al. |
| 2011/0172266 | A1 | 7/2011 | Page et al. |
| 2011/0178081 | A1 | 7/2011 | Page et al. |
| 2011/0178082 | A1 | 7/2011 | Page et al. |
| 2011/0269757 | A1 | 11/2011 | Page et al. |
| 2012/0172352 | A1 | 7/2012 | Page et al. |
| 2012/0316380 | A1 | 12/2012 | Page et al. |
| 2013/0123256 | A1 | 5/2013 | Page et al. |
| 2013/0143879 | A1 | 6/2013 | Page et al. |
| 2013/0158027 | A1 | 6/2013 | Page et al. |
| 2013/0296362 | A1 | 11/2013 | Page et al. |

FOREIGN PATENT DOCUMENTS

| WO | WO 2008/113856 | 9/2008 |
| WO | WO 2008/116926 | 10/2008 |
| WO | WO 2010/035217 | 4/2010 |
| WO | WO 2010/035219 | 4/2010 |
| WO | WO 2010/035220 | 4/2010 |
| WO | WO 2010/035221 | 4/2010 |
| WO | WO 2011/036651 | 3/2011 |
| WO | WO 2011/101805 | 8/2011 |

OTHER PUBLICATIONS

Englert, S. M. et al. "Pyrazolones Derived from the Carbethoxypiperidones" *Journal of American Chemical Society*, Mar. 1934, pp. 700-702, vol. 56.

Carpino, P. et al. "Pyrazolinone-piperidine Dipeptide Growth Hormone Secretagogues (GHSs): Discovery of Capromorelin" *Bioorganic & Medicinal Chemistry*, Feb. 20, 2003, pp. 581-590, vol. 11, No. 4.

Carpino, P. et al. "Discovery and Biological Characterization of Capromorelin Analogues with Extended Half-Lives" *Bioorganic & Medicinal Chemistry Letters*, Nov. 18, 2002, pp. 3279-3282, vol. 12, No. 22.

Guillou, S. et al. "N-arylation of 3-alkoxypyrazoles, the case of the pyridines" *Tetrahedron*, Feb. 10, 2010, pp. 2654-2663, vol. 66, No. 14.

Cai, H. et al. "The vascular NAD(P)H oxidases as therapeutic targets in cardiovascular diseases" *TRENDS in Pharmacological Sciences*, Sep. 2003, pp. 471-478, vol. 24, No. 9.

Thabut, G. et al. "Tumor Necrosis Factor-α Increases Airway Smooth Muscle Oxidants Production through a NADPH Oxidase-like System to Enhance Myosin Light Chain Phosphorylation and Contractility" *The Journal of Biological Chemistry*, Jun. 21, 2002, pp. 22814-22821, vol. 277, No. 25.

Djordjevic, T. et al. "Human Urotensin II Is a Novel Activator of NADPH Oxidase in Human Pulmonary Artery Smooth Muscle Cells" *Arteriosclerosis, Thrombosis, and Vascular Biology*, 2005, pp. 519-525, vol. 25.

Yang, S. et al. "Characterization of Interferon Gamma Receptors on Osteoclasts: Effect of Interferon Gamma on Osteoclastic Superoxide Generation" *Journal of Cellular Biochemistry*, 2002, pp. 645-654, vol. 84.

(Continued)

*Primary Examiner* — Kendra D Carter
(74) *Attorney, Agent, or Firm* — Saliwanchik, Lloyd & Eisenschenk

(57) ABSTRACT

The present invention is related to pyrazolo piperidine derivatives of Formula (I), pharmaceutical composition thereof and to their use for the treatment and/or prophylaxis of disorders or conditions related to Nicotinamide adenine dinucleotide phosphate oxidase (NADPH Oxidase).

15 Claims, No Drawings

(56) References Cited

OTHER PUBLICATIONS

Pillarsetti, S. et al. "Role of oxidative stress and inflammation in the origin of Type 2 diabetes—a paradigm shift" *Expert Opinion on Therapeutic Targets*, 2004, pp. 401-408, vol. 8, No. 5.

Shi, Y. et al. "Increased NAD(P)H Oxidase and Reactive Oxygen Species in Coronary Arteries After Balloon Injury" *Arteriosclerosis, Thrombosis, and Vascular Biology*, 2001, pp. 739-745, vol. 21.

Brigham, K. "Role of Free Radicals in Lung Injury" *Chest*, Jun. 1986, pp. 859-863, vol. 89, No. 6.

Liu, J. et al. "Extracellular superoxide enhances 5-HT-induced murine pulmonary artery vasoconstriction" *American Journal of Physiology—Lung Cellular and Molecular Physiology*, 2004, pp. L111-L118, vol. 287.

Nunomura, A. et al. "Oxidative Damage Is the Earliest Event in Alzheimer Disease" *Journal of Neuropathology and Experimental Neurology*, Aug. 2001, pp. 759-767, vol. 60, No. 8.

Girouard, H. et al. "Neurovascular coupling in the normal brain and in hypertension, stroke, and Alzheimer disease" *Journal of Applied Physiology*, 2006, pp. 328-335, vol. 100.

Vernet, P. et al. "Analysis of Reactive Oxygen Species Generating Systems in Rat Epididymal Spermatozoa" *Biology of Reproduction*, 2001, pp. 1102-1113, vol. 65.

Leto, T. L. et al. "Role of Nox Family NADPH Oxidases in Host Defense" *Antioxidants & Redox Signaling*, 2006, pp. 1549-1561, vol. 8, Nos. 9-10.

Cheng, G. et al. "Homologs of gp91*phox*: cloning and tissue expression of Nox3, Nox4, and Nox5" *Gene*, 2001, pp. 131-140, vol. 269.

Written Opinion in International Application No. PCT/IB2011/050667, Jun. 22, 2011, pp. 1-8.

PYRAZOLO PIPERIDINE DERIVATIVES AS NADPH OXIDASE INHIBITORS

CROSS-REFERENCE TO RELATED APPLICATION

This application is the U.S. national stage application of International Patent Application No. PCT/IB2011/050667, filed Feb. 17, 2011, the disclosure of which is hereby incorporated by reference in its entirety, including all figures, tables and amino acid or nucleic acid sequences.

FIELD OF THE INVENTION

The present invention relates to pyrazolo piperidine derivatives of Formula (I), pharmaceutical composition thereof and to their use for the preparation of a medicament for the treatment and/or prophylaxis of cardiovascular diseases, respiratory disorders, disorders affecting the metabolism, skin and/or bone diseases, neurodegenerative diseases, kidney diseases, reproduction disorders, inflammatory disorders and cancers. Specifically, the present invention is related to pyrazolo piperidine derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super-oxide anion [$.O_2^-$], hydroxyl [HO.], peroxyl [ROO.], alkoxyl [RO.] and hydroperoxyl [HOO.]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al., 2002, *J. Biol. Chem.*, 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, *Chest,* 89(6): 859-863). NADPH oxidase-dependent ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al., 2005, *Arterioscler. Thromb. Vasc. Biol.,* 25, 519-525; Liva et al., 2004, *Am. J. Physiol. Lung, Cell. Mol. Physiol.,* 287: L111-118). Further, pulmonary fibrosis has been characterized by lung inflammation and excessive generation of ROS.

Osteoclasts, which are macrophage-like cells that play a crucial role in bone turn-over (e.g. bone resorption), generate ROS through NADPH oxidase-dependent mechanisms (Yang et al., 2002, *J. Cell. Chem.* 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al., 2000, *Free Rad. Biol. Med.,* 28:91-101).

Further, it has been suggested that controlling oxidative stress (ROS) in mitochondria and/or inflammation may be a beneficial approach for the treatment of diabetes (Pillarisetti et al., 2004, *Expert Opin. Ther. Targets,* 8(5):401-408).

ROS are also strongly implicated in the pathogenesis of atherosclerosis, cell proliferation, hypertension and reperfusion injury cardiovascular diseases in general (Cai et al., 2003, *Trends Pharmacol. Sci.,* 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al., 2001, *Throm. Vasc. Biol.,* 2001, 21, 739-745)

It is believed that oxidative stress or free radical damage is also a major causative factor in neurodegenerative diseases. Such damages may include mitochondrial abnormalities, neuronal demyelination, apoptosis, neuronal death and reduced cognitive performance, potentially leading to the development of progressive neurodegenerative disorders (Nunomura et al., 2001, *J. Neuropathol. Exp. Neurol.,* 60:759-767; Girouard, 2006, *J. Appl. Physiol.* 100:328-335).

Further, the generation of ROS by sperm has been demonstrated in a large number of species and has been suggested to be attributed to an NADPH oxidase within spermatozoa (Vernet et al., *Biol. Reprod.,* 2001, 65:1102-1113). Excessive ROS generation has been suggested to be implicated in sperm pathology, including male infertility and also in some penile disorders and prostate cancer.

NADPH oxidases are multi-subunit enzymes made up of a membrane-bound cytochrome b558 domain and three cytosolic protein subunits, p47phox, p67phox and a small GTPase, Rac. Seven iso forms of NOX enzymes have been identified including NOX1, NOX2, NOX3, NOX4, NOX5, DUOX1 and DUOX2 (Leto et al., 2006, *Antioxid Redox Signal,* 8(9-10):1549-61; Cheng et al., 2001, *Gene,* 16; 269(1-2):131-40).

Thus, ROS derived from NADPH contribute to the pathogenesis of numerous diseases, especially cardiovascular diseases or disorders, respiratory disorder or disease, disease or disorder affecting the metabolism, bone disorders, neurodegenerative diseases, inflammatory diseases, reproduction disorder or disease, pain, cancer and disease or disorders of the gastrointestinal system. Therefore, it would be highly desirable to develop new active agents focusing on the ROS signalling cascade, especially on NADPH oxidases (NOX).

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, respiratory disorders, disorders affecting the metabolism, skin and/or bone diseases, neurodegenerative diseases, kidney diseases, reproduction disorders, inflammatory disorders, cancers, allergic disorders, traumatisms, septic, hemorrhagic and anaphylactic shock, diseases or disorders of the gastrointestinal system, angiogenesis and angiogenesis-dependent conditions. Notably, the invention is related to new molecules useful in the inhibition or reduction of ROS production in cells.

A first aspect of the invention provides a pyrazolo piperidine derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined below, as well as tautomers, geometrical isomers, optically active forms, pharmaceutically acceptable salts and pharmaceutically active derivative thereof with the proviso that the compound is not selected from the group consisting of:

5-methyl-2-phenyl-1,2,4,5,6,7-hexahydro-3H-pyrazolo[4,3-c]pyridin-3-one;

5-ethyl-2-phenyl-1,2,4,5,6,7-hexahydro-3H-pyrazolo[4,3-c]pyridin-3-one;

2-phenyl-5-propyl-1,2,4,5,6,7-hexahydro-3H-pyrazolo[4,3-c]pyridin-3-one;

5-butyl-2-phenyl-1,2,4,5,6,7-hexahydro-3H-pyrazolo[4,3-c]pyridin-3-one;

5-(3-methylbutyl)-2-phenyl-1,2,4,5,6,7-hexahydro-3H-pyrazolo[4,3-c]pyridin-3-one;

5-benzyl-1,2,4,5,6,7-hexahydro-3H-pyrazolo[4,3-c]pyridin-3-one.

A second aspect of the invention relates to a pyrazolo piperidine derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined below, as well as tautomers, geometrical isomers, optically active forms, pharmaceutically acceptable salts and pharmaceutically active derivative thereof for use as a medicament.

A third aspect of the invention relates to a pharmaceutical composition containing at least one a pyrazolo piperidine derivative according to the invention, as well as pharmaceutically acceptable salts and pharmaceutically active derivative thereof and a pharmaceutically acceptable carrier, diluent or excipient thereof.

A fourth aspect of the invention resides in a use of a pyrazolo piperidine derivative according to the invention as well as pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and/or other diseases, and disorders associated with Nicotinamide adenine dinucleotide phosphate oxidase (NADPH Oxidase).

A fifth aspect of the invention relates to a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase). The method comprises administering a pyrazolo piperidine derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined below, as well as tautomers, geometrical isomers, optically active forms, pharmaceutically acceptable salts and pharmaceutically active derivative thereof in a patient in need thereof.

A sixth aspect of the invention relates to a pyrazolo piperidine derivative according to Formula (I), wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined below, as well as tautomers, geometrical isomers, optically active forms, pharmaceutically acceptable salts and pharmaceutically active derivative thereof, for the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system, angiogenesis and angiogenesis-dependent and other diseases and/or disorders associated with Nicotinamide adenine dinucleotide phosphate oxidase (NADPH Oxidase).

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms. Particularly, those include $C_1$-$C_6$ alkyl.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3,7,11,15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH═CH$_2$), n-2-propenyl (allyl, —CH$_2$CH═CH$_2$), isopropenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —CH$_2$C≡CH), 2-butynyl, 2-pentene-4-ynyl, and the like. Particularly, these include $C_2$-$C_8$ alkynyl, more preferably $C_2$-$C_6$ alkynyl and the like. Preferably those include $C_2$-$C_6$ alkynyl which refers to groups having 2 to 6 carbon atoms and having at least 1 or 2 sites of alkynyl unsaturation.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "$C_1$-$C_6$ alkyl aryl" refers to aryl groups having a $C_1$-$C_6$ alkyl substituent, including methyl phenyl, ethyl phenyl and the like.

The term "aryl $C_1$-$C_6$ alkyl" refers to $C_1$-$C_6$ alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, iso quinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "$C_1$-$C_6$ alkyl heteroaryl" refers to heteroaryl groups having a $C_1$-$C_6$ alkyl substituent, including methyl furyl and the like.

The term "heteroaryl $C_1$-$C_6$ alkyl" refers to $C_1$-$C_6$ alkyl groups having a heteroaryl substituent, including furyl methyl and the like.

The term "$C_2$-$C_6$ alkenyl aryl" refers to an aryl groups having a $C_2$-$C_6$ alkenyl substituent, including vinyl phenyl and the like.

The term "aryl $C_2$-$C_6$ alkenyl" refers to a $C_2$-$C_6$ alkenyl groups having an aryl substituent, including phenyl vinyl and the like.

The term "$C_2$-$C_6$ alkenyl heteroaryl" refers to heteroaryl groups having a $C_2$-$C_6$ alkenyl substituent, including vinyl pyridinyl and the like.

The term "heteroaryl $C_2$-$C_6$ alkenyl" refers to $C_1$-$C_6$ alkenyl groups having a heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "$C_1$-$C_6$ alkyl $C_3$-$C_8$-cycloalkyl" refers to $C_3$-$C_8$-cycloalkyl groups having a $C_1$-$C_6$ alkyl substituent, including methyl cyclopentyl and the like.

The term "$C_3$-$C_8$-cycloalkyl $C_1$-$C_6$ alkyl" refers to $C_1$-$C_6$ alkyl groups having a $C_3$-$C_8$-cycloalkyl substituent, including 3-cyclopentyl propyl and the like.

The term "$C_1$-$C_6$ alkyl heterocycloalkyl" refers to heterocycloalkyl groups having a $C_1$-$C_6$ alkyl substituent, including 4-methylpiperidinyl and the like.

The term "heterocycloalkyl $C_1$-$C_6$ alkyl" refers to $C_1$-$C_6$ alkyl groups having a heterocycloalkyl substituent, including (1-methylpiperidin-4-yl)methyl and the like.

The term "carboxy" refers to the group —C(O)OH.

The term "carboxy $C_1$-$C_6$ alkyl" refers to $C_1$-$C_6$ alkyl groups having a carboxy substituent, including 2-carboxyethyl and the like.

The term "acyl" refers to the group —C(O)R where R includes H, "$C_1$-$C_6$ alkyl," preferably "$C_1$-$C_6$ alkyl," "aryl," "heteroaryl," "$C_3$-$C_8$-cycloalkyl," "heterocycloalkyl," "aryl $C_1$-$C_6$ alkyl," "heteroaryl $C_1$-$C_6$ alkyl," "$C_3$-$C_8$-cycloalkyl $C_1$-$C_6$ alkyl" or "heterocycloalkyl $C_1$-$C_6$ alkyl", including acetyl and the like.

The term "acyl $C_1$-$C_6$ alkyl" to $C_1$-$C_6$ alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "$C_1$-$C_6$ alkyl", "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", including acetyloxy and the like.

The term "acyloxy $C_1$-$C_6$ alkyl" refers to $C_1$-$C_6$ alkyl groups having an acyloxy substituent, including 2-(ethylcarbonyloxy)ethyl and the like.

The term "alkoxy" refers to the group —O—R where R includes "$C_1$-$C_6$ alkyl", "aryl", "heteroaryl", "aryl $C_1$-$C_6$ alkyl" or "heteroaryl $C_1$-$C_6$ alkyl". Preferred alkoxy groups include for example, methoxy, ethoxy, phenoxy and the like.

The term "alkoxy $C_1$-$C_6$ alkyl" refers to $C_1$-$C_6$ alkyl groups having an alkoxy substituent, including methoxyethyl and the like.

The term "alkoxycarbonyl" refers to the group —C(O)OR where R includes "$C_1$-$C_6$ alkyl", "aryl", "heteroaryl", "aryl $C_1$-$C_6$ alkyl", "heteroaryl $C_1$-$C_6$ alkyl" or "heteroalkyl".

The term "alkoxycarbonyl $C_1$-$C_6$ alkyl" refers to $C_1$-$C_6$ alkyl groups having an alkoxycarbonyl substituent, including 2-(benzyloxycarbonyl)ethyl and the like.

The term "aminocarbonyl" refers to the group —C(O)NRR' where R and R' are independently H, $C_1$-$C_6$ alkyl, aryl, heteroaryl, "aryl $C_1$-$C_6$ alkyl" or "heteroaryl $C_1$-$C_6$ alkyl," including N-phenyl carbonyl and the like.

The term "aminocarbonyl $C_1$-$C_6$ alkyl" refers to alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl", including acetylamino and the like.

The term "acylamino $C_1$-$C_6$ alkyl" refers to $C_1$-$C_6$ alkyl groups having an acylamino substituent, including 2-(propionylamino)ethyl and the like.

The term "ureido" refers to the group —NRC(O)NR'R" where R, R' and R" are independently H, "$C_1$-$C_6$ alkyl," "$C_2$-$C_6$ alkenyl," "alkynyl," "$C_3$-$C_8$-cycloalkyl," "heterocycloalkyl," "$C_1$-$C_6$ aryl," "hetero aryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl," and where R' and R," together with the nitrogen atom to which they are attached, can optionally form a 3-8-membered heterocycloalkyl ring.

The term "ureido $C_1$-$C_6$ alkyl" refers to $C_1$-$C_6$ alkyl groups having an ureido substituent, including 2-(N'-methylureido)ethyl and the like.

The term "carbamate" refers to the group —NRC(O)OR' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "$C_1$-$C_6$ alkyl aryl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl" and optionally R can also be hydrogen.

The term "amino" refers to the group —NRR' where R and R' are independently H, "$C_1$-$C_6$ alkyl", "aryl", "heteroaryl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —N$^+$RR'R" where R, R' and R" are independently "$C_1$-$C_6$ alkyl", "$C_1$-$C_6$ alkyl aryl", "$C_1$-$C_6$ alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "$C_1$-$C_6$ alkyl," "$C_1$-$C_6$ alkyl" substituted with halogens, e.g., an —OSO$_2$—CF$_3$ group, "$C_2$-$C_6$ alkenyl," "alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl alkyl".

The term "sulfonyloxy $C_1$-$C_6$ alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "$C_1$-$C_6$ alkyl," "$C_1$-$C_6$ alkyl" substituted with halogens, e.g., an —SO$_2$—CF$_3$ group, "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "cycloalkyl $C_1$-$C_6$ alkyl," or "heterocycloalkyl $C_1$-$C_6$ alkyl".

The term "sulfonyl $C_1$-$C_6$ alkyl" refers to alkyl groups having a sulfonyl substituent, including 2-(methylsulfonyl)ethyl and the like.

The term "sulfinyl" refers to a group "—S(O)—R" wherein R is selected from "alkyl," "alkyl" substituted with halogens, e.g., a —SO—CF$_3$ group, "$C_2$-$C_6$ alkenyl," "$C_2$-$C_6$ alkynyl," "$C_3$-$C_8$-cycloalkyl," "heterocycloalkyl," "aryl," "hetero aryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfinyl alkyl" refers to alkyl groups having a sulfinyl substituent, including 2-(methylsulfinyl)ethyl and the like.

The term "sulfanyl" refers to groups —S—R where R includes H, "$C_1$-$C_6$ alkyl," "$C_1$-$C_6$ alkyl" substituted with halogens, e.g., a —S—CF$_3$ group, "$C_2$-$C_6$ alkenyl," "$C_2$-$C_6$ alkynyl," "$C_3$-$C_8$-cycloalkyl," "heterocycloalkyl," "aryl," "hetero aryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "alkynylheteroaryl," "cycloalkyl $C_1$-$C_6$ alkyl," or "heterocycloalkyl $C_1$-$C_6$ alkyl". Preferred sulfanyl groups include methylsulfanyl, ethylsulfanyl, and the like.

The term "sulfanyl $C_1$-$C_6$ alkyl" refers to $C_1$-$C_5$-alkyl groups having a sulfanyl substituent, including 2-(ethylsulfanyl)ethyl and the like.

The term "sulfonylamino" refers to a group —NRSO$_2$—R' where R and R' are independently "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl", "heteroaryl $C_1$-$C_6$ alkyl," "aryl $C_2$-$C_6$ alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl".

The term "sulfonylamino $C_1$-$C_6$ alkyl" refers to alkyl groups having a sulfonylamino substituent, including 2-(ethylsulfonylamino)ethyl and the like.

The term "aminosulfonyl" refers to a group —$SO_2$—NRR' where R and R' are independently H, "$C_1$-$C_6$ alkyl," "$C_2$-$C_6$ alkenyl," "$C_2$-$C_6$ alkynyl," "$C_3$-$C_8$-cycloalkyl," "heterocycloalkyl," "aryl," "heteroaryl," "aryl $C_1$-$C_6$ alkyl," "heteroaryl $C_1$-$C_6$ alkyl," "aryl alkenyl," "heteroaryl $C_2$-$C_6$ alkenyl," "aryl $C_2$-$C_6$ alkynyl," "heteroaryl $C_2$-$C_6$ alkynyl," "$C_3$-$C_8$-cycloalkyl $C_1$-$C_6$ alkyl," or "heterocycloalkyl $C_1$-$C_6$ alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl $C_1$-$C_6$ alkyl" refers to $C_1$-$C_6$ alkyl groups having an aminosulfonyl substituent, including 2-(cyclohexylaminosulfonyl)ethyl and the like.

Unless otherwise constrained by the definition of the individual substituent, all the above substituents should be understood as being all optionally substituted.

Unless otherwise constrained by the definition of the individual substituent, the term "substituted" refers to groups substituted with from 1 to 5 substituents selected from the group consisting of "$C_1$-$C_6$ alkyl," "$C_2$-$C_6$ alkenyl," "$C_2$-$C_6$ alkynyl," "$C_3$-$C_8$-cycloalkyl," "heterocycloalkyl," "$C_1$-$C_6$ alkyl aryl," "$C_1$-$C_6$ alkyl heteroaryl," "$C_1$-$C_6$ alkyl cycloalkyl," "$C_1$-$C_6$ alkyl heterocyclo alkyl," "amino," "aminosulfonyl," "ammonium," "alkoxy," "acylamino," "amino carbonyl," "aryl," "heteroaryl," "sulfinyl," "sulfonyl," "sulphonamide", "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions. The invention further encompasses any tautomers of the compounds according to the invention.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension, idiopathic pulmonary fibrosis and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, dermatitis, wound healing and scar formation.

The term "bone disorder" includes osteoporosis, osteoporasis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuroinflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, kidney fibrosis, glomerulonephritis, nephrotoxicity of aminoglycosides and platinum compounds and hyperactive bladder. In a particular embodiment, the term according to the invention includes chronic kidney diseases or disorders.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase.

The term "liver diseases or disorders" include liver fibrosis, alcohol induced fibrosis, steatosis and non alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, renal cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, lung adenocarcinoma, bladder cancer or epithelial cancer) or the related diseases which require the administration to a mammal in a therapeutic effective dose of a compound expressed by the Formula (I) in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

The term "angiogenesis" includes sprouting angiogenesis, intussusceptive angiogenesis, vasculogenesis, arteriogenesis and lymphangiogenesis. Angiogenesis is the formation of new blood vessels from pre-existing capillaries or post-capillary venules and occurs in pathological conditions such as cancers, arthritis and inflammation. A large variety of tissues, or organs comprised of organized tissues, can support angiogenesis in disease conditions including skin, muscle, gut, connective tissue, joints, bones and the like tissue in which blood vessels can invade upon angiogenic stimuli. As used herein, the term "angiogenesis-dependent condition" is intended to mean a condition where the process of angiogenesis or vasculogenesis sustains or augments a pathological condition. Vasculogenesis results from the formation of new blood vessels arising from angioblasts which are endothelial cell precursors. Both processes result in new blood vessel formation and are included in the meaning of the term angiogenesis-dependent conditions. Similarly, the term "angiogenesis" as used herein is intended to include de novo formation of vessels such as those arising from vasculogenesis as well as those arising from branching and sprouting of existing vessels, capillaries and venules.

The term "angiogenesis inhibitory," means which is effective in the decrease in the extent, amount, or rate of neovascularization. Effecting a decrease in the extent, amount, or rate of endothelial cell proliferation or migration in the tissue is a specific example of inhibiting angiogenesis. Angiogenesis inhibitory activity is particularly useful in the treatment of any cancers as it targets tumor growth process and in the absence of neovascularization of tumor tissue, the tumor tissue does not obtain the required nutrients, slows in growth, ceases additional growth, regresses and ultimately becomes necrotic resulting in killing of the tumor. Further, an angiogenesis inhibitory activity is particularly useful in the treatment of any cancers as it is particularly effective against the formation of metastases because their formation also requires vascularization of a primary tumor so that the metastatic cancer cells can exit the primary tumor and their establishment in a secondary site requires neovascularization to support growth of the metastases.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compounds According to the Invention

In one embodiment, the invention provides a pyrazolo piperidine derivative according to Formula (I):

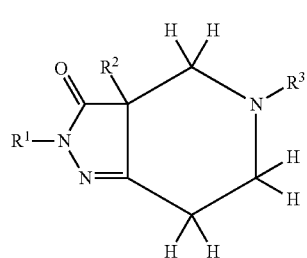

(I)

wherein $R^1$ is selected from H; optionally substituted alkoxycarbonyl; optionally substituted $C_1$-$C_6$ alkyl such as optionally substituted methyl (e.g. methyl), optionally substituted ethyl (e.g. 2-hydroxy ethyl); optionally substituted $C_2$-$C_6$ alkenyl; optionally substituted $C_2$-$C_6$ alkynyl; optionally substituted alkoxy; optionally substituted alkoxy $C_1$-$C_6$ alkyl such as optionally substituted optionally substituted alkoxy ethyl like optionally substituted phenoxy ethyl (e.g. phenoxy ethyl, 4-chlorophenoxy ethyl), optionally substituted methoxy ethyl (e.g. 2-methoxy ethyl); optionally substituted aminoalkyl; optionally substituted acyl; optionally substituted aryl such as optionally substituted phenyl (e.g. phenyl, 3-methoxyphenyl, 2-methoxyphenyl, 3-methoxyphenyl, 4-methoxyphenyl, 1-methoxy phenyl, 3-benzyloxy phenyl, 1-chlorophenyl, 2-chlorophenyl, 3-chlorophenyl, 4-chlorophenyl, 2-fluorophenyl, 2-chloro-4-fluorophenyl, 3-fluorophenyl, 3-benzonitrile, 4-benzonitrile, 3-phenyl acetamide); optionally substituted $C_1$-$C_6$ alkyl aryl; optionally substituted aryl $C_1$-$C_6$ alkyl such as optionally substituted aryl methyl such as optionally substituted phenyl methyl (e.g. benzyl, 4-chlorobenzyl, 2-methoxy benzyl, 3-methoxy benzyl, 4-methoxy benzyl); optionally substituted heteroaryl such as optionally substituted benzodioxolyl (e.g. 1,3 benzodioxol-5-yl), optionally substituted benzothiazolyl (e.g. 2-methyl 1,3-benzothiazol-6-yl); optionally substituted $C_1$-$C_6$ alkyl heteroaryl; optionally substituted heteroaryl $C_1$-$C_6$ alkyl such as optionally substituted optionally substituted heteroaryl methyl such as optionally substituted optionally substituted imidazo[1,2,a]pyridine-2-yl methyl (e.g. 2-imidazo[1,2,a]pyridine-2-ylmethyl); optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl such as optionally substituted piperidine (e.g. (e.g. 1-methyl piperidin-4-yl, 2-piperidin-1-ylethyl); optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl such as optionally substituted heterocycloalkyl ethyl like morpholinyl ethyl (e.g. 2-morpholin-4-ylethyl) or optionally substituted piperidine ethyl (e.g. 2-piperinin-1-yl ethyl); $R^2$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl such as optionally substituted pyridin alkyl like optionally substituted pyridin methyl (e.g. pyridine-3-yl-methyl); optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl such as optionally substituted phenyl alkyl like optionally substituted phenyl methyl (e.g. benzyl) and optionally substituted heteroaryl $C_1$-$C_6$ alkyl such as optionally substituted heteroaryl methyl like optionally substituted pyridine methyl (e.g. pyridine-3-ylmethyl); $R^3$ is selected from —S(O)—$R^4$, —S(O)$_2$—$R^4$, optionally substituted $C_3$-$C_8$-cycloalkyl, optionally substituted heterocycloalkyl and —$CR^5R^6R^7$; $R^4$ is selected from H; optionally substituted amino; optionally substituted $C_1$-$C_6$ alkyl such as optionally substituted methyl (e.g. methyl); optionally substituted $C_2$-$C_6$ alkenyl; optionally substituted $C_2$-$C_6$ alkynyl; optionally substituted alkoxy; optionally substituted alkoxy $C_1$-$C_6$ alkyl such optionally substituted aminoalkyl; optionally substituted acyl; optionally substituted aryl such as optionally substituted phenyl (e.g. 4-methyl phenyl); optionally substituted $C_1$-$C_6$ alkyl aryl; optionally substituted aryl $C_1$-$C_6$ alkyl such as optionally substituted aryl methyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^5$ is selected from H and —$CR^8R^9R^{10}$; $R^6$ is selected from H and —$CR^{11}R^{12}R^{13}$; $R^7$ is selected from H, —$CR^{14}R^{15}R^{16}$ and —C(O)—$R^{17}$; $R^8$, $R^9$, $R^{10}$, $R^{11}$, $R^{12}$, $R^{13}$, $R^{14}$, $R^{15}$, $R^{16}$ and $R^{17}$-are independently selected from H; halogen; optionally substituted amino; optionally substituted acyl; optionally substituted $C_1$-$C_6$ alkyl such as optionally substituted alkoxy alkyl like alkoxy methyl (e.g. 2-phenoxy methyl); optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_6$ alkyl; —$CR^8R^9R^{10}$, —$CR^{11}R^{12}R^{13}$ or —$CR^{14}R^{15}R^{16}$ can independently form an optionally substituted ring selected from an optionally substituted aryl such as optionally substituted phenyl (e.g. phenyl, 3-cyano phenyl, 4-cyano phenyl, 2-chlorophenyl, 3-chlorophenyl, 4-chlorophenyl, 1-chlorophenyl, 2-chlorophenyl, 4-dichlorophenyl, 3,4-dichlorophenyl, 3,5-dichlorophenyl, 3-trifluoromethyl phenyl, 4-methoxyphenyl, 3-methoxyphenyl, 4-methoxyphenyl, 3-chloro-4-fluorophenyl, 3-fluoro-4-cyano phenyl-4-benzyloxy phenyl, 4-methyl sulfonyl phenyl, 4-methyl phenyl acetamide, N-methyl phenylamide); an optionally substituted heteroaryl such as optionally substituted pyridine (e.g. pyridine-2-yl, pyridine-3-yl, 6-chloropyridin-3-yl); an optionally substituted $C_3$-$C_8$-cycloalkyl or an optionally substituted heterocycloalkyl, as well as tautomers, geometrical isomers, optically active forms, pharmaceutically acceptable salts and pharmaceutically active derivative thereof with the proviso that the compound is not selected from the group consisting of:

5-methyl-2-phenyl-1,2,4,5,6,7-hexahydro-3H-pyrazolo[4,3-c]pyridin-3-one;
5-ethyl-2-phenyl-1,2,4,5,6,7-hexahydro-3H-pyrazolo[4,3-c]pyridin-3-one;
2-phenyl-5-propyl-1,2,4,5,6,7-hexahydro-3H-pyrazolo[4,3-c]pyridin-3-one;
5-butyl-2-phenyl-1,2,4,5,6,7-hexahydro-3H-pyrazolo[4,3-c]pyridin-3-one;
5-(3-methylbutyl)-2-phenyl-1,2,4,5,6,7-hexahydro-3H-pyrazolo[4,3-c]pyridin-3-one;
5-benzyl-1,2,4,5,6,7-hexahydro-3H-pyrazolo[4,3-c]pyridin-3-one (RN 1093759-87-5).

In a particular embodiment, the invention provides a tautomer of compound according to Formula (I), selected from a compound of Formula (Ia) and a compound of Formula (Ib):

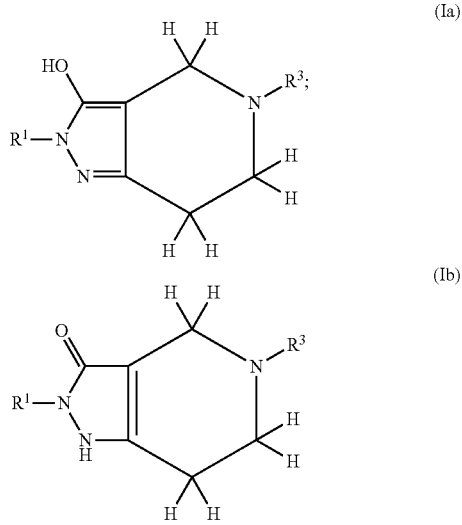

as well as optically active forms, pharmaceutically acceptable salts and pharmaceutically active derivative thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In a particular embodiment, is provided a pyrazolo piperidine derivative according to Formula (I) selected from the following group:

5-benzyl-2-(4-chlorobenzyl)-1,2,4,5,6,7-hexahydro-3H-pyrazolo[4,3-c]pyridin-3-one;
5-benzyl-2-(2-chloro-4-fluorophenyl)-1,2,4,5,6,7-hexahydro-3H-pyrazolo[4,3-c]pyridin-3-one;
5-benzyl-2-[3-(benzyloxy)phenyl]-1,2,4,5,6,7-hexahydro-3H-pyrazolo[4,3-c]pyridin-3-one;
5-benzyl-2-(3-chlorophenyl)-1,2,4,5,6,7-hexahydro-3H-pyrazolo[4,3-c]pyridin-3-one;
5-benzyl-2-[2-(4-chlorophenoxy)ethyl]-1,2,4,5,6,7-hexahydro-3H-pyrazolo[4,3-c]pyridin-3-one;
5-benzyl-2-methyl-1,2,4,5,6,7-hexahydro-3H-pyrazolo[4,3-c]pyridin-3-one;
2-benzyl-5-(4-chlorobenzyl)-1,2,4,5,6,7-hexahydro-3H-pyrazolo[4,3-c]pyridin-3-one;
2-benzyl-5-(3-chlorobenzyl)-1,2,4,5,6,7-hexahydro-3H-pyrazolo[4,3-c]pyridin-3-one;
2-benzyl-5-(4-methoxybenzyl)-1,2,4,5,6,7-hexahydro-3H-pyrazolo[4,3-c]pyridin-3-one;
2,5-dibenzyl-1,2,4,5,6,7-hexahydro-3H-pyrazolo[4,3-c]pyridin-3-one;
5-benzyl-2-phenyl-1,2,4,5,6,7-hexahydro-3H-pyrazolo[4,3-c]pyridin-3-one;
5-(4-chlorobenzyl)-2-methyl-1,2,4,5,6,7-hexahydro-3H-pyrazolo[4,3-c]pyridin-3-one;
5-(4-methoxybenzyl)-2-methyl-1,2,4,5,6,7-hexahydro-3H-pyrazolo[4,3-c]pyridin-3-one;
5-(3-chlorobenzyl)-2-methyl-1,2,4,5,6,7-hexahydro-3H-pyrazolo[4,3-c]pyridin-3-one;
2-benzyl-5-(3-methoxybenzyl)-1,2,4,5,6,7-hexahydro-3H-pyrazolo[4,3-c]pyridin-3-one;
2-benzyl-5-(3,5-dimethoxybenzyl)-1,2,4,5,6,7-hexahydro-3H-pyrazolo[4,3-c]pyridin-3-one;
2-[2-(4-chlorophenoxy)ethyl]-5-(4-methoxybenzyl)octahydro-3H-pyrazolo[4,3-c]pyridin-3-one;
5-(4-chlorobenzyl)-2-phenyl-1,2,4,5,6,7-hexahydro-3H-pyrazolo[4,3-c]pyridin-3-one;
2-benzyl-5-(3,4-dichlorobenzyl)-1,2,4,5,6,7-hexahydro-3H-pyrazolo[4,3-c]pyridin-3-one;
2-benzyl-5-(3,5-dichlorobenzyl)-1,2,4,5,6,7-hexahydro-3H-pyrazolo[4,3-c]pyridin-3-one;
2-benzyl-5-(2,4-dichlorobenzyl)-1,2,4,5,6,7-hexahydro-3H-pyrazolo[4,3-c]pyridin-3-one;
5-benzyl-2-(3-methoxyphenyl)-1,2,4,5,6,7-hexahydro-3H-pyrazolo[4,3-c]pyridin-3-one;
5-(4-chlorobenzyl)-2-(3-methoxyphenyl)-1,2,4,5,6,7-hexahydro-3H-pyrazolo[4,3-c]pyridin-3-one;
5-[4-(benzyloxy)benzyl]-2-(3-methoxyphenyl)-1,2,4,5,6,7-hexahydro-3H-pyrazolo[4,3-c]pyridin-3-one;
5-(3-chlorobenzyl)-2-(3-methoxyphenyl)-1,2,4,5,6,7-hexahydro-3H-pyrazolo[4,3-c]pyridin-3-one;
5-benzyl-2-(2-methoxyphenyl)-1,2,4,5,6,7-hexahydro-3H-pyrazolo[4,3-c]pyridin-3-one;
5-(2-chlorobenzyl)-2-(3-methoxyphenyl)-1,2,4,5,6,7-hexahydro-3H-pyrazolo[4,3-c]pyridin-3-one;
4-{[2-(3-methoxyphenyl)-3-oxo-1,2,3,4,6,7-hexahydro-5H-pyrazolo[4,3-c]pyridin-5-yl]methyl}benzonitrile
5-(4-chlorobenzyl)-2-(1-methylpiperidin-4-yl)-1,2,4,5,6,7-hexahydro-3H-pyrazolo[4,3-c]pyridin-3-one;
5-(4-chlorobenzyl)-2-(3-methoxybenzyl)-1,2,4,5,6,7-hexahydro-3H-pyrazolo[4,3-c]pyridin-3-one;
5-(4-chlorobenzyl)-2-(2-methoxybenzyl)-1,2,4,5,6,7-hexahydro-3H-pyrazolo[4,3-c]pyridin-3-one;
2-(3-methoxyphenyl)-5-(pyridin-2-ylmethyl)-1,2,4,5,6,7-hexahydro-3H-pyrazolo[4,3-c]pyridin-3-one;
5-(4-methoxybenzyl)-2-(2-methoxyethyl)-1,2,4,5,6,7-hexahydro-3H-pyrazolo[4,3-c]pyridin-3-one;
5-(4-methoxybenzyl)-2-(1-methylpiperidin-4-yl)-1,2,4,5,6,7-hexahydro-3H-pyrazolo[4,3-c]pyridin-3-one;
5-(4-chlorobenzyl)-2-(2-methoxyethyl)-1,2,4,5,6,7-hexahydro-3H-pyrazolo[4,3-c]pyridin-3-one;
5-(4-methoxybenzyl)-2-(2-morpholin-4-ylethyl)-1,2,4,5,6,7-hexahydro-3H-pyrazolo[4,3-c]pyridin-3-one;
2-(1,3-benzodioxol-5-yl)-5-(4-chlorobenzyl)-1,2,4,5,6,7-hexahydro-3H-pyrazolo[4,3-c]pyridin-3-one;
2-(1,3-benzodioxol-5-yl)-5-(4-methoxybenzyl)-1,2,4,5,6,7-hexahydro-3H-pyrazolo[4,3-c]pyridin-3-one;
5-(2,4-dichlorobenzyl)-2-(3-methoxyphenyl)-1,2,4,5,6,7-hexahydro-3H-pyrazolo[4,3-c]pyridin-3-one;
5-(4-chlorobenzyl)-2-(4-methoxyphenyl)-1,2,4,5,6,7-hexahydro-3H-pyrazolo[4,3-c]pyridin-3-one;

2-phenyl-5-(pyridin-3-ylmethyl)-1,2,4,5,6,7-hexahydro-3H-pyrazolo[4,3-c]pyridin-3-one;
2-(2-methoxybenzyl)-5-(4-methoxybenzyl)-1,2,4,5,6,7-hexahydro-3H-pyrazolo[4,3-c]pyridin-3-one;
2-(3-methoxybenzyl)-5-(4-methoxybenzyl)-1,2,4,5,6,7-hexahydro-3H-pyrazolo[4,3-c]pyridin-3-one;
4-[(2-benzyl-3-oxo-1,2,3,4,6,7-hexahydro-5H-pyrazolo[4,3-c]pyridin-5-yl)methyl]benzonitrile;
2-(2-hydroxyethyl)-5-(4-methoxybenzyl)-1,2,4,5,6,7-hexahydro-3H-pyrazolo[4,3-c]pyridin-3-one;
4-{[2-(1,3-benzodioxol-5-yl)-3-oxo-1,2,3,4,6,7-hexahydro-5H-pyrazolo[4,3-c]pyridin-5-yl]methyl}benzonitrile;
3-[5-(4-chlorobenzyl)-3-oxo-1,3,4,5,6,7-hexahydro-2H-pyrazolo[4,3-c]pyridin-2-yl]benzonitrile;
5-(4-chlorobenzyl)-2-(2-hydroxyethyl)-1,2,4,5,6,7-hexahydro-3H-pyrazolo[4,3-c]pyridin-3-one;
5-(4-chlorobenzyl)-2-(2-morpholin-4-ylethyl)-1,2,4,5,6,7-hexahydro-3H-pyrazolo[4,3-c]pyridin-3-one;
3a-benzyl-5-(4-chlorobenzyl)-2-methyl-2,3a,4,5,6,7-hexahydro-3H-pyrazolo[4,3-c]pyridin-3-one;
5-(2-phenoxyethyl)-2-phenyl-1,2,4,5,6,7-hexahydro-3H-pyrazolo[4,3-c]pyridin-3-one;
4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;
N-{4-[(3-oxo-2-phenyl-1,2,3,4,6,7-hexahydro-5H-pyrazolo[4,3-c]pyridin-5-yl)methyl]phenyl}acetamide;
N-methyl-4-[(3-oxo-2-phenyl-1,2,3,4,6,7-hexahydro-5H-pyrazolo[4,3-c]pyridin-5-yl)methyl]benzamide;
4-[5-(4-chlorobenzyl)-3-oxo-1,3,4,5,6,7-hexahydro-2H-pyrazolo[4,3-c]pyridin-2-yl]benzonitrile;
5-(methylsulfonyl)-2-phenyl-1,2,4,5,6,7-hexahydro-3H-pyrazolo[4,3-c]pyridin-3-one;
5-[(4-methylphenyl)sulfonyl]-2-phenyl-1,2,4,5,6,7-hexahydro-3H-pyrazolo[4,3-c]pyridin-3-one;
4-{[2-(2-hydroxyethyl)-3-oxo-1,2,3,4,6,7-hexahydro-5H-pyrazolo[4,3-c]pyridin-5-yl]methyl}benzonitrile;
4-{[2-(4-chlorophenyl)-3-oxo-1,2,3,4,6,7-hexahydro-5H-pyrazolo[4,3-c]pyridin-5-yl]methyl}benzonitrile;
2-(1,3-benzodioxol-5-yl)-5-(3-chloro-4-fluorobenzyl)-1,2,4,5,6,7-hexahydro-3H-pyrazolo[4,3-c]pyridin-3-one;
5-(3-chloro-4-fluorobenzyl)-2-(2-methyl-1,3-benzothiazol-6-yl)-1,2,4,5,6,7-hexahydro-3H-pyrazolo[4,3-c]pyridin-3-one;
4-{[2-(3-methoxybenzyl)-3-oxo-1,2,3,4,6,7-hexahydro-5H-pyrazolo[4,3-c]pyridin-5-yl]methyl}benzonitrile;
2-(2-methyl-1,3-benzothiazol-6-yl)-5-[4-(methylsulfonyl)benzyl]-1,2,4,5,6,7-hexahydro-3H-pyrazolo[4,3-c]pyridin-3-one;
5-(4-chlorobenzyl)-2-(2-methyl-1,3-benzothiazol-6-yl)-1,2,4,5,6,7-hexahydro-3H-pyrazolo[4,3-c]pyridin-3-one;
2-benzyl-5-(pyridin-2-ylmethyl)-1,2,4,5,6,7-hexahydro-3H-pyrazolo[4,3-c]pyridin-3-one;
3-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;
2-(2-methyl-1,3-benzothiazol-6-yl)-5-(pyridin-3-ylmethyl)-1,2,4,5,6,7-hexahydro-3H-pyrazolo[4,3-c]pyridin-3-one;
3-[(2-benzyl-3-oxo-1,2,3,4,6,7-hexahydro-5H-pyrazolo[4,3-c]pyridin-5-yl)methyl]benzonitrile;
4-{[2-(4-methoxyphenyl)-3-oxo-1,2,3,4,6,7-hexahydro-5H-pyrazolo[4,3-c]pyridin-5-yl]methyl}benzonitrile;
3-fluoro-4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;
2-(1,3-benzodioxol-5-yl)-5-[4-(methylsulfonyl)benzyl]-1,2,4,5,6,7-hexahydro-3H-pyrazolo[4,3-c]pyridin-3-one;
2-(1,3-benzodioxol-5-yl)-5-[3-(trifluoromethyl)benzyl]-1,2,4,5,6,7-hexahydro-3H-pyrazolo[4,3-c]pyridin-3-one;
2-(3-methoxybenzyl)-5-(pyridin-3-ylmethyl)-1,2,4,5,6,7-hexahydro-3H-pyrazolo[4,3-c]pyridin-3-one;
2-(2-methoxybenzyl)-5-(pyridin-3-ylmethyl)-1,2,4,5,6,7-hexahydro-3H-pyrazolo[4,3-c]pyridin-3-one;
4-{[2-(2-methoxybenzyl)-3-oxo-1,2,3,4,6,7-hexahydro-5H-pyrazolo[4,3-c]pyridin-5-yl]methyl}benzonitrile;
2-(4-chlorophenyl)-5-(pyridin-3-ylmethyl)-1,2,4,5,6,7-hexahydro-3H-pyrazolo[4,3-c]pyridin-3-one;
3-[3-oxo-5-(pyridin-3-ylmethyl)-1,3,4,5,6,7-hexahydro-2H-pyrazolo[4,3-c]pyridin-2-yl]benzonitrile;
4-{[3-oxo-2-(2-piperidin-1-ylethyl)-1,2,3,4,6,7-hexahydro-5H-pyrazolo[4,3-c]pyridin-5-yl]methyl}benzonitrile;
N-{3-[3-oxo-5-(pyridin-3-ylmethyl)-1,3,4,5,6,7-hexahydro-2H-pyrazolo[4,3-c]pyridin-2-yl]phenyl}acetamide;
2-(2-fluorophenyl)-5-(pyridin-3-ylmethyl)-1,2,4,5,6,7-hexahydro-3H-pyrazolo[4,3-c]pyridin-3-one;
4-{[2-(2-fluorophenyl)-3-oxo-1,2,3,4,6,7-hexahydro-5H-pyrazolo[4,3-c]pyridin-5-yl]methyl}benzonitrile;
5-[(6-chloropyridin-3-yl)methyl]-2-(2-methoxyethyl)-1,2,4,5,6,7-hexahydro-3H-pyrazolo[4,3-c]pyridin-3-one;
N-{3-[5-(3-chloro-4-fluorobenzyl)-3-oxo-1,3,4,5,6,7-hexahydro-2H-pyrazolo[4,3-c]pyridin-2-yl]phenyl}acetamide;
4-{[2-(4-methoxybenzyl)-3-oxo-1,2,3,4,6,7-hexahydro-5H-pyrazolo[4,3-c]pyridin-5-yl]methyl}benzonitrile;
5-(4-chlorobenzyl)-2-methyl-3a-(pyridin-3-ylmethyl)-2,3a,4,5,6,7-hexahydro-3H-pyrazolo[4,3-c]pyridin-3-one;
2-(2-methyl-1,3-benzothiazol-6-yl)-5-[3-(trifluoromethyl)benzyl]-1,2,4,5,6,7-hexahydro-3H-pyrazolo[4,3-c]pyridin-3-one;
5-(3-chloro-4-fluorobenzyl)-2-(4-chlorophenyl)-1,2,4,5,6,7-hexahydro-3H-pyrazolo[4,3-c]pyridin-3-one;
3-[5-(3-chloro-4-fluorobenzyl)-3-oxo-1,3,4,5,6,7-hexahydro-2H-pyrazolo[4,3-c]pyridin-2-yl]benzonitrile;
3-{3-oxo-5-[3-(trifluoromethyl)benzyl]-1,3,4,5,6,7-hexahydro-2H-pyrazolo[4,3-c]pyridin-2-yl}benzonitrile;
3-{5-[(6-chloropyridin-3-yl)methyl]-3-oxo-1,3,4,5,6,7-hexahydro-2H-pyrazolo[4,3-c]pyridin-2-yl}benzonitrile;
2-benzyl-5-(3-chloro-4-fluorobenzyl)-1,2,4,5,6,7-hexahydro-3H-pyrazolo[4,3-c]pyridin-3-one;
2-(4-chlorophenyl)-5-[(6-chloropyridin-3-yl)methyl]-1,2,4,5,6,7-hexahydro-3H-pyrazolo[4,3-c]pyridin-3-one;
5-[(6-chloropyridin-3-yl)methyl]-2-(2-fluorophenyl)-1,2,4,5,6,7-hexahydro-3H-pyrazolo[4,3-c]pyridin-3-one;
5-[(6-chloropyridin-3-yl)methyl]-2-(1-methylpiperidin-4-yl)-1,2,4,5,6,7-hexahydro-3H-pyrazolo[4,3-c]pyridin-3-one;
2-benzyl-5-[(6-chloropyridin-3-yl)methyl]-1,2,4,5,6,7-hexahydro-3H-pyrazolo[4,3-c]pyridin-3-one;
4-{5-[(6-chloropyridin-3-yl)methyl]-3-oxo-1,3,4,5,6,7-hexahydro-2H-pyrazolo[4,3-c]pyridin-2-yl}benzonitrile;
2-benzyl-5-(pyridin-3-ylmethyl)-1,2,4,5,6,7-hexahydro-3H-pyrazolo[4,3-c]pyridin-3-one;
2-(2-methyl-1,3-benzothiazol-6-yl)-5-(pyridin-2-ylmethyl)-1,2,4,5,6,7-hexahydro-3H-pyrazolo[4,3-c]pyridin-3-one;
5-(2-chlorobenzyl)-2-(2-methyl-1,3-benzothiazol-6-yl)-1,2,4,5,6,7-hexahydro-3H-pyrazolo[4,3-c]pyridin-3-one;
2-benzyl-5-(methylsulfonyl)-1,2,4,5,6,7-hexahydro-3H-pyrazolo[4,3-c]pyridin-3-one; and
2-(imidazo[1,2-a]pyridin-2-ylmethyl)-5-[(4-methylphenyl)sulfonyl]-1,2,4,5,6,7-hexahydro-3H-pyrazolo[4,3-c]pyridin-3-one.

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as a cardiovascular disorder or disease, a respiratory disorder or disease, a disease or disorder affecting the metabolism, a skin disorder, a bone disorder, a neuroinflammatory disorder, a neurodegenerative disorder, a kidney disease, a reproduction disorder, a disease or disorder affecting the eye and/or the lens, a condition affecting the inner ear, an inflammatory disorder or disease, a liver disease, pain, a cancer, angiogenesis, angiogenesis-dependent conditions and/or a disease or disorders of the gastrointestinal system.

Pharmaceutical compositions of the invention can contain one or more pyrazolo piperidine derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably injectable.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences, 21st Edition,* 2005, University of the Sciences in Philadelphia, Lippincott Williams & Wilkins, which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, acacia, gelatin, sorbitol, tragacanth, mucilage of starch and polyvinylpyrrolidone. Fillers include, but are not limited to, lactose, sugar, microcrystalline cellulose, maize starch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum.

The compounds of this invention can also be administered in sustained release forms or from sustained release drug delivery systems. A description of representative sustained release materials can also be found in the incorporated materials in *Remington's Pharmaceutical Sciences.*

Mode of Administration

Compositions of this invention may be administered in any manner, including, but not limited to, orally, parenterally, sublingually, transdermally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v.

infusion. In a preferred embodiment, pyrazolo piperidine derivatives according to the invention are administered intravenously or subcutaneously.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Combination

According to one embodiment of the invention, the compounds according to the invention and pharmaceutical formulations thereof can be administered alone or in combination with a co-agent useful in the treatment of cancer, such as substances used in conventional chemotherapy directed against solid tumors and for control of establishment of metastases or substances used in hormonotherapy or any other molecule that act by triggering programmed cell death e.g. for example a co-agent selected from the category of drugs that stop the synthesis of pre DNA molecule building blocks such as methotrexate (Abitrexate®), fluorouracil (Adrucil®), hydroxyurea (Hydrea®), and mercaptopurine (Purinethol®). e.g. for example a co-agent selected from the category of drugs that directly damage the DNA in the nucleus of the cell such as cisplatin (Platinol®) and antibiotics—daunorubicin (Cerubidine®), doxorubicin (Adriamycin®), and etoposide (VePesid®). e.g. for example a co-agent selected from the category of drugs that effect the synthesis or breakdown of the mitotic spindles such as Vinblastine (Velban®), Vincristine (Oncovin®) and Pacitaxel (Taxol®).

According to another embodiment of the invention, the compounds according to the invention and pharmaceutical formulations thereof can be administered in combination with agents targeting cell-surface proteins such as gene transfer of cytokine receptor chain and receptor-targeted cytotoxin administration According to another embodiment of the invention, the compounds according to the invention and pharmaceutical formulations thereof can be administered in combination with radiation therapy.

The invention encompasses the administration of a compound according to the invention or of a pharmaceutical formulation thereof, wherein the compound according to the invention or the pharmaceutical formulation thereof is administered to an individual prior to, simultaneously or sequentially with other therapeutic regimens or co-agents useful in the treatment of cancers (e.g. multiple drug regimens), in a therapeutically effective amount. Compounds according to the invention or the pharmaceutical formulations thereof that are administered simultaneously with said co-agents can be administered in the same or different composition(s) and by the same or different route(s) of administration.

In another particular embodiment, the compounds and methods of the invention are contemplated for use in the treatment of cancers wherein the administration of a compound according to the invention is typically conducted during or after chemotherapy, hormonotherapy or radiotherapy.

In another particular embodiment, the compounds and methods of the invention are contemplated for use in the treatment of cancers wherein the administration of a compound according to the invention is typically conducted after a regimen of chemotherapy, hormonotherapy or radiotherapy at times where the tumor tissue will be responding to the toxic assault by inducing angiogenesis to recover by the provision of a blood supply and nutrients to the tumor tissue.

In another embodiment, the administration of a compound according to the invention is performed after surgery where solid tumors have been removed as a prophylaxis against metastases.

Patients

In an embodiment, patients according to the invention are patients suffering from a cardiovascular disorder or disease.

In another embodiment, patients according to the invention are patients suffering from a respiratory disorder or disease.

In another embodiment, patients according to the invention are patients suffering from a disease or disorder affecting the metabolism.

In another embodiment, patients according to the invention are patients suffering from a skin disorder.

In another embodiment, patients according to the invention are patients suffering from a bone disorder.

In another embodiment, patients according to the invention are patients suffering from a neuroinflammatory disorder and/or a neurodegenerative disorder.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease.

In another embodiment, patients according to the invention are patients suffering from a liver disease.

In another embodiment, patients according to the invention are patients suffering from pain, such as inflammatory pain.

In another embodiment, patients according to the invention are patients suffering from a cancer.

In another embodiment, patients according to the invention are suffering from angiogenesis or an angiogenesis-dependent condition.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

Use According to the Invention

In another embodiment, the invention provides a pyrazolo piperidine derivative according to Formula (I) wherein $R^1$ is selected from H; optionally substituted alkoxycarbonyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^2$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl and optionally substituted heteroaryl $C_1$-$C_6$ alkyl; $R^3$ is selected from H, —S(O)—$R^4$, —S(O)$_2$—$R^4$, optionally substituted $C_3$-$C_8$-cycloalkyl, optionally substituted heterocycloalkyl and —$CR^5R^6R^7$; $R^4$ is selected from H; optionally substituted amino; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl such optionally substituted aminoalkyl; optionally substituted acyl; optionally substituted aryl; optionally substituted $C_1$-$C_6$ alkyl aryl; optionally substituted aryl $C_1$-$C_6$ alkyl such as optionally substituted aryl methyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_6$ alkyl; $R^5$ is selected from H and —$CR^8R^9R^{10}$; $R^6$ is selected from H and —$CR^{11}R^{12}R^{13}$; $R^7$ is selected from H, —$CR^{14}R^{15}R^{16}$ and —C(O)—$R^{17}$; $R^8$, $R^9$, $R^{10}$, $R^{11}$, $R^{12}$, $R^{13}$, $R^{14}$, $R^{15}$, $R^{16}$ and $R^{17}$-are independently selected from H; halogen; optionally substituted amino; optionally substituted acyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; —$CR^8R^9R^{10}$, —$CR^{11}R^{12}R^{13}$ or —$CR^{14}R^{15}R^{16}$ can independently form an optionally substituted ring selected from an optionally substituted aryl; an optionally substituted heteroaryl; an optionally substituted $C_3$-$C_8$-cycloalkyl or an optionally substituted heterocycloalkyl, as well as tautomers, geometrical isomers, optically active forms, pharmaceutically acceptable salts and pharmaceutically active derivative thereof for use as a medicament.

In a further particular embodiment, is provided a pyrazolo piperidine derivative according to Formula (I) as defined above for use as a medicament with the proviso that the compound is not selected from the group consisting of:
5-methyl-2-phenyl-1,2,4,5,6,7-hexahydro-3H-pyrazolo[4,3-c]pyridin-3-one;
5-ethyl-2-phenyl-1,2,4,5,6,7-hexahydro-3H-pyrazolo[4,3-c]pyridin-3-one;
2-phenyl-5-propyl-1,2,4,5,6,7-hexahydro-3H-pyrazolo[4,3-c]pyridin-3-one;
5-butyl-2-phenyl-1,2,4,5,6,7-hexahydro-3H-pyrazolo[4,3-c]pyridin-3-one;
5-(3-methylbutyl)-2-phenyl-1,2,4,5,6,7-hexahydro-3H-pyrazolo[4,3-c]pyridin-3-one.

In a further embodiment, the invention provides a pyrazolo piperidine derivative according to the invention wherein $R^1$ is selected from optionally substituted aryl and optionally substituted heteroaryl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^1$ is selected from optionally substituted $C_1$-$C_6$ alkyl; optionally substituted $C_2$-$C_6$ alkenyl; optionally substituted $C_2$-$C_6$ alkynyl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^1$ is selected from optionally substituted aryl $C_1$-$C_6$ alkyl and optionally substituted heteroaryl $C_1$-$C_6$ alkyl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^1$ is optionally substituted heterocycloalkyl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^1$ is optionally substituted heterocycloalkyl $C_1$-$C_6$ alkyl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^1$ is optionally substituted alkoxy $C_1$-$C_6$ alkyl; $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^2$ is H; $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^2$ is selected from optionally substituted aryl $C_1$-$C_6$ alkyl and optionally substituted heteroaryl $C_1$-$C_6$ alkyl; $R^1$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^3$ is —$CR^5R^6R^7$; $R^1$, $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$ are as defined in the detailed description.

In another further embodiment, the invention provides a pyrazolo piperidine derivative according to the invention wherein $R^3$ is —$CR^5R^6R^7$; $R^5$ and $R^6$ are H; $R^7$ is —$CR^{14}R^{15}R^{16}$; $R^1$, $R^2$, $R^{14}$, $R^{15}$, $R^{16}$ and $R^{17}$ are as defined in the detailed description.

In another further embodiment, the invention provides a pyrazolo piperidine derivative according to the invention wherein $R^3$ is —$CR^5R^6R^7$; $R^5$ and $R^6$ are H; $R^7$ is —$CR^{14}R^{15}R^{16}$; —$CR^{14}R^{15}R^{16}$ form a ring selected from optionally substituted aryl and optionally substituted heteroaryl; $R^1$ and $R^2$ are as defined in the detailed description.

In another embodiment, the invention provides a pyrazolo piperidine derivative according to the invention wherein $R^3$ is $S(O)_2$—$R^4$; $R^1$, $R^2$ and $R^4$ are as defined in the detailed description.

In another further embodiment, the invention provides a pyrazolo piperidine derivative according to the invention wherein $R^3$ is $S(O)_2$—$R^4$ and $R^4$ is selected from optionally substituted $C_1$-$C_6$ alkyl; optionally substituted $C_2$-$C_6$ alkenyl and optionally substituted $C_2$-$C_6$ alkynyl; $R^1$ and $R^2$ are as defined in the detailed description.

In another further embodiment, the invention provides a pyrazolo piperidine derivative according to the invention wherein $R^3$ is $S(O)_2$—$R^4$ and $R^4$ is selected from optionally substituted aryl and optionally substituted heteroaryl; $R^1$ and $R^2$ are as defined in the detailed description.

In another embodiment, the invention provides a use of a pyrazolo piperidine derivative according to Formula (I) wherein $R^1$ is selected from H; optionally substituted alkoxycarbonyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^2$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl and optionally substituted heteroaryl $C_1$-$C_6$ alkyl; $R^3$ is selected from H, —S(O)—$R^4$, —S(O)$_2$—$R^4$, optionally substituted $C_3$-$C_8$-cycloalkyl, optionally substituted heterocycloalkyl and —$CR^5R^6R^7$; $R^4$ is selected from H; optionally substituted amino; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl such optionally substituted aminoalkyl; optionally substituted acyl; optionally substituted aryl; optionally substituted $C_1$-$C_6$ alkyl aryl; optionally substituted aryl $C_1$-$C_6$ alkyl such as optionally substituted aryl methyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^5$ is selected from H and —$CR^8R^9R^{10}$; $R^6$ is selected from H and —$CR^{11}R^{12}R^{13}$; $R^7$ is selected from H, —$CR^{14}R^{15}R^{16}$ and —C(O)—$R^{17}$; $R^8$, $R^9$, $R^{10}$, $R^{11}$, $R^{12}$, $R^{13}$, $R^{14}$, $R^{15}$, $R^{16}$ and $R^{17}$ are independently selected from H; halogen; optionally substituted amino; optionally substituted acyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; —$CR^8R^9R^{10}$, —$CR^{11}R^{12}R^{13}$ or —$CR^{14}R^{15}R^{16}$ can independently form an optionally substituted ring selected from an optionally substituted aryl; an optionally substituted heteroaryl; an optionally substituted $C_3$-$C_8$-cycloalkyl or an optionally substituted heterocycloalkyl, as well as tautomers, geometrical isomers, optically active forms, pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

In another embodiment, the invention provides a pyrazolo piperidine derivative according to Formula (I) wherein $R^1$ is selected from H; optionally substituted alkoxycarbonyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl and optionally substituted heterocycloalkyl $C_1$-$C_6$ alkyl; $R^2$ is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl and optionally substituted heteroaryl $C_1$-$C_6$ alkyl; $R^3$ is selected from H, —S(O)—$R^4$, —S(O)$_2$—$R^4$, optionally substituted $C_3$-$C_8$-cycloalkyl, optionally substituted heterocycloalkyl and —$CR^5R^6R^7$; $R^4$ is selected from H; optionally substituted amino; optionally substituted $C_1$-$C_6$ alkyl; optionally substituted $C_2$-$C_6$ alkenyl; optionally substituted C$_2$-C$_6$ alkynyl; optionally substituted alkoxy; optionally substituted alkoxy C$_1$-C$_6$ alkyl such optionally substituted aminoalkyl; optionally substituted acyl; optionally substituted aryl; optionally substituted C$_1$-C$_6$ alkyl aryl; optionally substituted aryl C$_1$-C$_6$ alkyl such as optionally substituted aryl methyl; optionally substituted heteroaryl; optionally substituted C$_1$-C$_6$ alkyl heteroaryl; optionally substituted heteroaryl C$_1$-C$_6$ alkyl; optionally substituted C$_2$-C$_6$ alkenyl aryl; optionally substituted aryl C$_2$-C$_6$ alkenyl; optionally substituted C$_2$-C$_6$ alkenyl heteroaryl; optionally substituted heteroaryl C$_2$-C$_6$ alkenyl; optionally substituted C$_3$-C$_5$-cycloalkyl; optionally substituted heterocycloalkyl; optionally substituted C$_1$-C$_6$ alkyl C$_3$-C$_8$-cycloalkyl; optionally substituted C$_3$-C$_8$-cycloalkyl C$_1$-C$_6$ alkyl; optionally substituted C$_1$-C$_6$ alkyl heterocycloalkyl and optionally substituted heterocycloalkyl C$_1$-C$_6$ alkyl; R$^5$ is selected from H and —CR$^8$R$^9$R$^{10}$; R$^6$ is selected from H and —CR$^{11}$R$^{12}$R$^{13}$; R$^7$ is selected from H, —CR$^{14}$R$^{15}$R$^{16}$ and —C(O)—R$^{17}$; R$^8$, R$^9$, R$^{10}$, R$^{11}$, R$^{12}$, R$^{13}$, R$^{14}$, R$^{15}$, R$^{16}$ and R$^{17}$-are independently selected from H; halogen; optionally substituted amino; optionally substituted acyl; optionally substituted C$_1$-C$_6$ alkyl; optionally substituted C$_2$-C$_6$ alkenyl; optionally substituted C$_2$-C$_6$ alkynyl; optionally substituted aryl; optionally substituted C$_1$-C$_6$ alkyl aryl; optionally substituted aryl C$_1$-C$_6$ alkyl; optionally substituted heteroaryl; optionally substituted C$_1$-C$_6$ alkyl heteroaryl; optionally substituted heteroaryl C$_1$-C$_6$ alkyl; optionally substituted C$_2$-C$_6$ alkenyl aryl; optionally substituted aryl C$_2$-C$_6$ alkenyl; optionally substituted C$_2$-C$_6$ alkenyl heteroaryl; optionally substituted heteroaryl C$_2$-C$_6$ alkenyl; optionally substituted C$_3$-C$_8$-cycloalkyl; optionally substituted heterocycloalkyl; optionally substituted C$_1$-C$_6$ alkyl C$_3$-C$_8$-cycloalkyl; optionally substituted C$_3$-C$_8$-cycloalkyl C$_1$-C$_6$ alkyl; optionally substituted C$_1$-C$_6$ alkyl heterocycloalkyl and optionally substituted heterocycloalkyl C$_1$-C$_6$ alkyl; —CR$^8$R$^9$R$^{10}$, —CR$^{11}$R$^{12}$R$^{13}$ or —CR$^{14}$R$^{15}$R$^{16}$ can independently form an optionally substituted ring selected from an optionally substituted aryl; an optionally substituted heteroaryl; an optionally substituted C$_3$-C$_8$-cycloalkyl or an optionally substituted heterocycloalkyl, as well as tautomers, geometrical isomers, optically active forms, pharmaceutically acceptable salts and pharmaceutically active derivative thereof for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase).

Compounds of the present invention include in particular those selected from the following group:

5-benzyl-2-(4-chlorobenzyl)-1,2,4,5,6,7-hexahydro-3H-pyrazolo[4,3-c]pyridin-3-one;
5-benzyl-2-(2-chloro-4-fluorophenyl)-1,2,4,5,6,7-hexahydro-3H-pyrazolo[4,3-c]pyridin-3-one;
5-benzyl-2-[3-(benzyloxy)phenyl]-1,2,4,5,6,7-hexahydro-3H-pyrazolo[4,3-c]pyridin-3-one;
2-(2-chloro-4-fluorophenyl)-1,2,4,5,6,7-hexahydro-3H-pyrazolo[4,3-c]pyridin-3-one;
2-benzyl-1,2,4,5,6,7-hexahydro-3H-pyrazolo[4,3-c]pyridin-3-one;
5-benzyl-2-(3-chlorophenyl)-1,2,4,5,6,7-hexahydro-3H-pyrazolo[4,3-c]pyridin-3-one;
5-benzyl-2-[2-(4-chlorophenoxy)ethyl]-1,2,4,5,6,7-hexahydro-3H-pyrazolo[4,3-c]pyridin-3-one;
5-benzyl-2-methyl-1,2,4,5,6,7-hexahydro-3H-pyrazolo[4,3-c]pyridin-3-one;
2-benzyl-5-(4-chlorobenzyl)-1,2,4,5,6,7-hexahydro-3H-pyrazolo[4,3-c]pyridin-3-one;
2-benzyl-5-(3-chlorobenzyl)-1,2,4,5,6,7-hexahydro-3H-pyrazolo[4,3-c]pyridin-3-one;
2-benzyl-5-(4-methoxybenzyl)-1,2,4,5,6,7-hexahydro-3H-pyrazolo[4,3-c]pyridin-3-one;
2,5-dibenzyl-1,2,4,5,6,7-hexahydro-3H-pyrazolo[4,3-c]pyridin-3-one;
5-benzyl-2-phenyl-1,2,4,5,6,7-hexahydro-3H-pyrazolo[4,3-c]pyridin-3-one;
5-(4-chlorobenzyl)-2-methyl-1,2,4,5,6,7-hexahydro-3H-pyrazolo[4,3-c]pyridin-3-one;
5-(4-methoxybenzyl)-2-methyl-1,2,4,5,6,7-hexahydro-3H-pyrazolo[4,3-c]pyridin-3-one;
5-(3-chlorobenzyl)-2-methyl-1,2,4,5,6,7-hexahydro-3H-pyrazolo[4,3-c]pyridin-3-one;
2-benzyl-5-(3-methoxybenzyl)-1,2,4,5,6,7-hexahydro-3H-pyrazolo[4,3-c]pyridin-3-one;
2-benzyl-5-(3,5-dimethoxybenzyl)-1,2,4,5,6,7-hexahydro-3H-pyrazolo[4,3-c]pyridin-3-one;
2-[2-(4-chlorophenoxy)ethyl]-5-(4-methoxybenzyl)octahydro-3H-pyrazolo[4,3-c]pyridin-3-one;
5-(4-chlorobenzyl)-2-phenyl-1,2,4,5,6,7-hexahydro-3H-pyrazolo[4,3-c]pyridin-3-one;
2-benzyl-5-(3,4-dichlorobenzyl)-1,2,4,5,6,7-hexahydro-3H-pyrazolo[4,3-c]pyridin-3-one;
2-benzyl-5-(3,5-dichlorobenzyl)-1,2,4,5,6,7-hexahydro-3H-pyrazolo[4,3-c]pyridin-3-one;
2-benzyl-5-(2,4-dichlorobenzyl)-1,2,4,5,6,7-hexahydro-3H-pyrazolo[4,3-c]pyridin-3-one;
5-benzyl-2-(3-methoxyphenyl)-1,2,4,5,6,7-hexahydro-3H-pyrazolo[4,3-c]pyridin-3-one;
5-(4-chlorobenzyl)-2-(3-methoxyphenyl)-1,2,4,5,6,7-hexahydro-3H-pyrazolo[4,3-c]pyridin-3-one;
5-[4-(benzyloxy)benzyl]-2-(3-methoxyphenyl)-1,2,4,5,6,7-hexahydro-3H-pyrazolo[4,3-c]pyridin-3-one;
5-(3-chlorobenzyl)-2-(3-methoxyphenyl)-1,2,4,5,6,7-hexahydro-3H-pyrazolo[4,3-c]pyridin-3-one;
5-benzyl-2-(2-methoxyphenyl)-1,2,4,5,6,7-hexahydro-3H-pyrazolo[4,3-c]pyridin-3-one
5-(2-chlorobenzyl)-2-(3-methoxyphenyl)-1,2,4,5,6,7-hexahydro-3H-pyrazolo[4,3-c]pyridin-3-one;
4-{[2-(3-methoxyphenyl)-3-oxo-1,2,3,4,6,7-hexahydro-5H-pyrazolo[4,3-c]pyridin-5-yl]methyl}benzonitrile;
5-(4-chlorobenzyl)-2-(1-methylpiperidin-4-yl)-1,2,4,5,6,7-hexahydro-3H-pyrazolo[4,3-c]pyridin-3-one;
5-(4-chlorobenzyl)-2-(3-methoxybenzyl)-1,2,4,5,6,7-hexahydro-3H-pyrazolo[4,3-c]pyridin-3-one;
5-(4-chlorobenzyl)-2-(2-methoxybenzyl)-1,2,4,5,6,7-hexahydro-3H-pyrazolo[4,3-c]pyridin-3-one;
2-(3-methoxyphenyl)-5-(pyridin-2-ylmethyl)-1,2,4,5,6,7-hexahydro-3H-pyrazolo[4,3-c]pyridin-3-one;
5-(4-methoxybenzyl)-2-(2-methoxyethyl)-1,2,4,5,6,7-hexahydro-3H-pyrazolo[4,3-c]pyridin-3-one;
5-(4-methoxybenzyl)-2-(1-methylpiperidin-4-yl)-1,2,4,5,6,7-hexahydro-3H-pyrazolo[4,3-c]pyridin-3-one;
5-(4-chlorobenzyl)-2-(2-methoxyethyl)-1,2,4,5,6,7-hexahydro-3H-pyrazolo[4,3-c]pyridin-3-one;
5-(4-methoxybenzyl)-2-(2-morpholin-4-ylethyl)-1,2,4,5,6,7-hexahydro-3H-pyrazolo[4,3-c]pyridin-3-one;

2-(1,3-benzodioxol-5-yl)-5-(4-chlorobenzyl)-1,2,4,5,6,7-hexahydro-3H-pyrazolo[4,3-c]pyridin-3-one;
2-(1,3-benzodioxol-5-yl)-5-(4-methoxybenzyl)-1,2,4,5,6,7-hexahydro-3H-pyrazolo[4,3-c]pyridin-3-one;
5-(2,4-dichlorobenzyl)-2-(3-methoxyphenyl)-1,2,4,5,6,7-hexahydro-3H-pyrazolo[4,3-c]pyridin-3-one;
5-(4-chlorobenzyl)-2-(4-methoxyphenyl)-1,2,4,5,6,7-hexahydro-3H-pyrazolo[4,3-c]pyridin-3-one;
2-phenyl-5-(pyridin-3-ylmethyl)-1,2,4,5,6,7-hexahydro-3H-pyrazolo[4,3-c]pyridin-3-one;
2-(2-methoxybenzyl)-5-(4-methoxybenzyl)-1,2,4,5,6,7-hexahydro-3H-pyrazolo[4,3-c]pyridin-3-one;
2-(3-methoxybenzyl)-5-(4-methoxybenzyl)-1,2,4,5,6,7-hexahydro-3H-pyrazolo[4,3-c]pyridin-3-one;
4-[(2-benzyl-3-oxo-1,2,3,4,6,7-hexahydro-5H-pyrazolo[4,3-c]pyridin-5-yl)methyl]benzonitrile;
2-(2-hydroxyethyl)-5-(4-methoxybenzyl)-1,2,4,5,6,7-hexahydro-3H-pyrazolo[4,3-c]pyridin-3-one;
4-{[2-(1,3-benzodioxol-5-yl)-3-oxo-1,2,3,4,6,7-hexahydro-5H-pyrazolo[4,3-c]pyridin-5-yl]methyl}benzonitrile;
3-[5-(4-chlorobenzyl)-3-oxo-1,3,4,5,6,7-hexahydro-2H-pyrazolo[4,3-c]pyridin-2-yl]benzonitrile;
5-(4-chlorobenzyl)-2-(2-hydroxyethyl)-1,2,4,5,6,7-hexahydro-3H-pyrazolo[4,3-c]pyridin-3-one;
5-(4-chlorobenzyl)-2-(2-morpholin-4-ylethyl)-1,2,4,5,6,7-hexahydro-3H-pyrazolo[4,3-c]pyridin-3-one;
3a-benzyl-5-(4-chlorobenzyl)-2-methyl-2,3a,4,5,6,7-hexahydro-3H-pyrazolo[4,3-c]pyridin-3-one;
5-(2-phenoxyethyl)-2-phenyl-1,2,4,5,6,7-hexahydro-3H-pyrazolo[4,3-c]pyridin-3-one;
4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;
N-{4-[(3-oxo-2-phenyl-1,2,3,4,6,7-hexahydro-5H-pyrazolo[4,3-c]pyridin-5-yl)methyl]phenyl}acetamide;
N-methyl-4-[(3-oxo-2-phenyl-1,2,3,4,6,7-hexahydro-5H-pyrazolo[4,3-c]pyridin-5-yl)methyl]benzamide;
4-[5-(4-chlorobenzyl)-3-oxo-1,3,4,5,6,7-hexahydro-2H-pyrazolo[4,3-c]pyridin-2-yl]benzonitrile;
5-(methylsulfonyl)-2-phenyl-1,2,4,5,6,7-hexahydro-3H-pyrazolo[4,3-c]pyridin-3-one;
5-[(4-methylphenyl)sulfonyl]-2-phenyl-1,2,4,5,6,7-hexahydro-3H-pyrazolo[4,3-c]pyridin-3-one;
4-{[2-(2-hydroxyethyl)-3-oxo-1,2,3,4,6,7-hexahydro-5H-pyrazolo[4,3-c]pyridin-5-yl]methyl}benzonitrile;
4-{[2-(4-chlorophenyl)-3-oxo-1,2,3,4,6,7-hexahydro-5H-pyrazolo[4,3-c]pyridin-5-yl]methyl}benzonitrile;
2-(1,3-benzodioxol-5-yl)-5-(3-chloro-4-fluorobenzyl)-1,2,4,5,6,7-hexahydro-3H-pyrazolo[4,3-c]pyridin-3-one;
5-(3-chloro-4-fluorobenzyl)-2-(2-methyl-1,3-benzothiazol-6-yl)-1,2,4,5,6,7-hexahydro-3H-pyrazolo[4,3-c]pyridin-3-one;
4-{[2-(3-methoxybenzyl)-3-oxo-1,2,3,4,6,7-hexahydro-5H-pyrazolo[4,3-c]pyridin-5-yl]methyl}benzonitrile;
2-(2-methyl-1,3-benzothiazol-6-yl)-5-[4-(methylsulfonyl)benzyl]-1,2,4,5,6,7-hexahydro-3H-pyrazolo[4,3-c]pyridin-3-one;
5-(4-chlorobenzyl)-2-(2-methyl-1,3-benzothiazol-6-yl)-1,2,4,5,6,7-hexahydro-3H-pyrazolo[4,3-c]pyridin-3-one;
2-benzyl-5-(pyridin-2-ylmethyl)-1,2,4,5,6,7-hexahydro-3H-pyrazolo[4,3-c]pyridin-3-one;
3-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;
2-(2-methyl-1,3-benzothiazol-6-yl)-5-(pyridin-3-ylmethyl)-1,2,4,5,6,7-hexahydro-3H-pyrazolo[4,3-c]pyridin-3-one;
3-[(2-benzyl-3-oxo-1,2,3,4,6,7-hexahydro-5H-pyrazolo[4,3-c]pyridin-5-yl)methyl]benzonitrile;
4-{[2-(4-methoxyphenyl)-3-oxo-1,2,3,4,6,7-hexahydro-5H-pyrazolo[4,3-c]pyridin-5-yl]methyl}benzonitrile;
3-fluoro-4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;
2-(1,3-benzodioxol-5-yl)-5-[4-(methylsulfonyl)benzyl]-1,2,4,5,6,7-hexahydro-3H-pyrazolo[4,3-c]pyridin-3-one;
2-(1,3-benzodioxol-5-yl)-5-[3-(trifluoromethyl)benzyl]-1,2,4,5,6,7-hexahydro-3H-pyrazolo[4,3-c]pyridin-3-one;
2-(3-methoxybenzyl)-5-(pyridin-3-ylmethyl)-1,2,4,5,6,7-hexahydro-3H-pyrazolo[4,3-c]pyridin-3-one;
2-(2-methoxybenzyl)-5-(pyridin-3-ylmethyl)-1,2,4,5,6,7-hexahydro-3H-pyrazolo[4,3-c]pyridin-3-one;
4-{[2-(2-methoxybenzyl)-3-oxo-1,2,3,4,6,7-hexahydro-5H-pyrazolo[4,3-c]pyridin-5-yl]methyl}benzonitrile;
2-(4-chlorophenyl)-5-(pyridin-3-ylmethyl)-1,2,4,5,6,7-hexahydro-3H-pyrazolo[4,3-c]pyridin-3-one;
3-[3-oxo-5-(pyridin-3-ylmethyl)-1,3,4,5,6,7-hexahydro-2H-pyrazolo[4,3-c]pyridin-2-yl]benzonitrile;
4-{[3-oxo-2-(2-piperidin-1-ylethyl)-1,2,3,4,6,7-hexahydro-5H-pyrazolo[4,3-c]pyridin-5-yl]methyl}benzonitrile;
N-{3-[3-oxo-5-(pyridin-3-ylmethyl)-1,3,4,5,6,7-hexahydro-2H-pyrazolo[4,3-c]pyridin-2-yl]phenyl}acetamide;
2-(2-fluorophenyl)-5-(pyridin-3-ylmethyl)-1,2,4,5,6,7-hexahydro-3H-pyrazolo[4,3-c]pyridin-3-one;
4-{[2-(2-fluorophenyl)-3-oxo-1,2,3,4,6,7-hexahydro-5H-pyrazolo[4,3-c]pyridin-5-yl]methyl}benzonitrile;
5-[(6-chloropyridin-3-yl)methyl]-2-(2-methoxyethyl)-1,2,4,5,6,7-hexahydro-3H-pyrazolo[4,3-c]pyridin-3-one;
N-{3-[5-(3-chloro-4-fluorobenzyl)-3-oxo-1,3,4,5,6,7-hexahydro-2H-pyrazolo[4,3-c]pyridin-2-yl]phenyl}acetamide;
4-{[2-(4-methoxybenzyl)-3-oxo-1,2,3,4,6,7-hexahydro-5H-pyrazolo[4,3-c]pyridin-5-yl]methyl}benzonitrile;
5-(4-chlorobenzyl)-2-methyl-3a-(pyridin-3-ylmethyl)-2,3a,4,5,6,7-hexahydro-3H-pyrazolo[4,3-c]pyridin-3-one;
2-(2-methyl-1,3-benzothiazol-6-yl)-5-[3-(trifluoromethyl)benzyl]-1,2,4,5,6,7-hexahydro-3H-pyrazolo[4,3-c]pyridin-3-one;
5-(3-chloro-4-fluorobenzyl)-2-(4-chlorophenyl)-1,2,4,5,6,7-hexahydro-3H-pyrazolo[4,3-c]pyridin-3-one;
3-[5-(3-chloro-4-fluorobenzyl)-3-oxo-1,3,4,5,6,7-hexahydro-2H-pyrazolo[4,3-c]pyridin-2-yl]benzonitrile;
3-{3-oxo-5-[3-(trifluoromethyl)benzyl]-1,3,4,5,6,7-hexahydro-2H-pyrazolo[4,3-c]pyridin-2-yl}benzonitrile;
3-{5-[(6-chloropyridin-3-yl)methyl]-3-oxo-1,3,4,5,6,7-hexahydro-2H-pyrazolo[4,3-c]pyridin-2-yl}benzonitrile;
2-benzyl-5-(3-chloro-4-fluorobenzyl)-1,2,4,5,6,7-hexahydro-3H-pyrazolo[4,3-c]pyridin-3-one;
2-(4-chlorophenyl)-5-[(6-chloropyridin-3-yl)methyl]-1,2,4,5,6,7-hexahydro-3H-pyrazolo[4,3-c]pyridin-3-one;
5-[(6-chloropyridin-3-yl)methyl]-2-(2-fluorophenyl)-1,2,4,5,6,7-hexahydro-3H-pyrazolo[4,3-c]pyridin-3-one;
5-[(6-chloropyridin-3-yl)methyl]-2-(1-methylpiperidin-4-yl)-1,2,4,5,6,7-hexahydro-3H-pyrazolo[4,3-c]pyridin-3-one;
2-benzyl-5-[(6-chloropyridin-3-yl)methyl]-1,2,4,5,6,7-hexahydro-3H-pyrazolo[4,3-c]pyridin-3-one;
4-{5-[(6-chloropyridin-3-yl)methyl]-3-oxo-1,3,4,5,6,7-hexahydro-2H-pyrazolo[4,3-c]pyridin-2-yl}benzonitrile;
2-benzyl-5-(pyridin-3-ylmethyl)-1,2,4,5,6,7-hexahydro-3H-pyrazolo[4,3-c]pyridin-3-one;
2-(2-methyl-1,3-benzothiazol-6-yl)-5-(pyridin-2-ylmethyl)-1,2,4,5,6,7-hexahydro-3H-pyrazolo[4,3-c]pyridin-3-one;

5-(2-chlorobenzyl)-2-(2-methyl-1,3-benzothiazol-6-yl)-1,2,4,5,6,7-hexahydro-3H-pyrazolo[4,3-c]pyridin-3-one;

2-benzyl-5-(methylsulfonyl)-1,2,4,5,6,7-hexahydro-3H-pyrazolo[4,3-c]pyridin-3-one; and 2-(imidazo[1,2-a]pyridin-2-ylmethyl)-5-[(4-methylphenyl)sulfonyl]-1,2,4,5,6,7-hexahydro-3H-pyrazolo[4,3-c]pyridin-3-one.

In another embodiment, the invention provides a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers allergic disorders, traumatisms, septic, hemorrhagic and anaphylactic shock, disorders of the gastrointestinal system, angiogenesis, angiogenesis-dependent conditions and other diseases and disorders associated with Nicotinamide adenine dinucleotide phosphate oxidase (NADPH Oxidase). The method comprises administering a compound according to Formula (I) in a patient in need thereof.

In another embodiment, the invention provides a method for inhibiting angiogenesis in a patient in need thereof, wherein the method comprises administering an angiogenesis inhibiting dose of a compound of Formula (I) in a patient in need thereof.

In another embodiment, the invention provides a method of inhibiting tumor neovascularization by inhibiting tumor angiogenesis according to the present methods. Similarly, the invention provides a method for inhibiting tumor growth by practicing the angiogenesis-inhibiting methods.

In a particular embodiment, the compounds and methods of the invention are contemplated for use in treatment of a tumor tissue of a patient with a tumor, solid tumor, a metastasis, a cancer, a melanoma, a skin cancer, a breast cancer, a hemangioma or angiofibroma and the like cancer, and the angiogenesis to be inhibited is tumor tissue angiogenesis where there is neovascularization of a tumor tissue. Typical solid tumor tissues treatable by the present compounds and methods include, but are not limited to, tumors of the skin, melanoma, lung, pancreas, breast, colon, laryngeal, ovarian, prostate, colorectal, head, neck, testicular, lymphoid, marrow, bone, sarcoma, renal, sweat gland, and the like tissues. Further examples of cancers treated are glioblastomas.

In another particular embodiment, the compounds and methods of the invention are contemplated for use in treatment of an inflamed tissue and the angiogenesis to be inhibited is inflamed tissue angiogenesis where there is neovascularization of inflamed tissue. In this case, the compound and method according to the invention contemplate the inhibition of angiogenesis in arthritic tissues, such as in a patient with chronic articular rheumatism, in immune or non-immune inflamed tissues, in psoriatic tissue and the like.

In embodiments, the invention contemplates inhibition of angiogenesis in a tissue. The extent of angiogenesis in a tissue, and therefore the extent of inhibition achieved by the present methods, can be evaluated by a variety of methods, such as are described herein.

According to an embodiment of the invention, the disease or condition is a cancer.

According to an embodiment of the invention, the compound according to the invention is to be administered in combination with a co-agent useful in the treatment of cancer.

According to an embodiment of the invention, the compound according to the invention is to be administered in combination with radiation therapy.

In another embodiment, the invention provides a pharmaceutical composition containing at least one derivative pyrazolo piperidine according to Formula (I) and a pharmaceutically acceptable carrier, diluent or excipient thereof.

The compounds of invention have been named according the IUPAC standards used in the program ACD/Name (product version 10.01).

Compounds according to the present invention comprise a compound according to Formula (I), its tautomers, its geometrical isomers, its optically active forms as enantiomers, diastereomers and its racemate forms, as well as pharmaceutically acceptable salts thereof. The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

Synthesis of Compounds of the Invention:

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approach for obtaining compounds of Formula (I) is depicted in Scheme 1 below.

Scheme 1

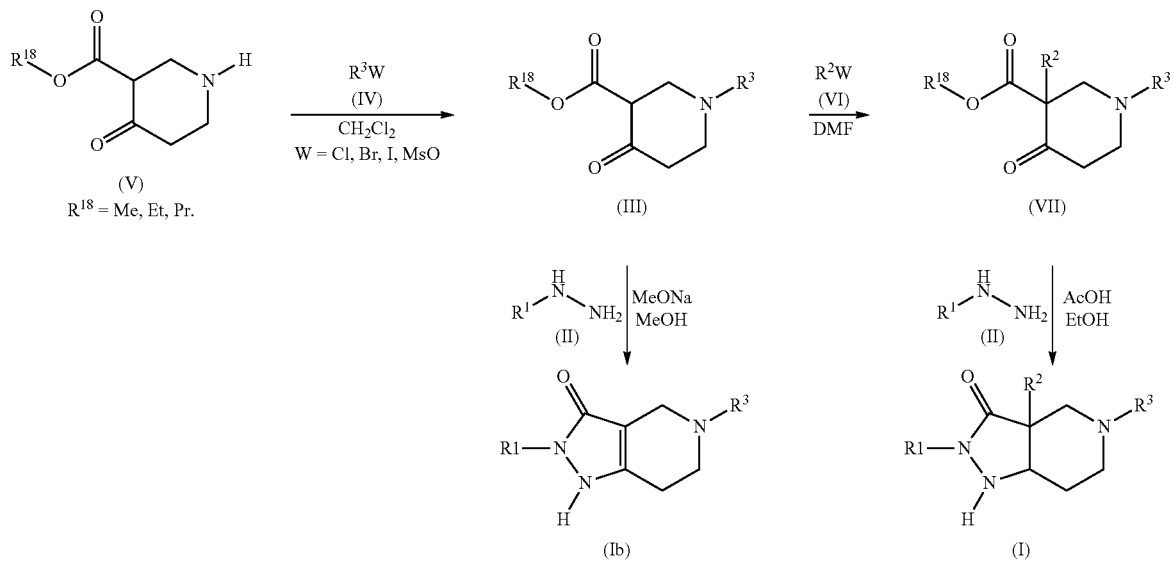

Pyrazolo piperidine derivatives according to Formula (I), whereby the substituents $R^1$, $R^2$ and $R^3$, are as above defined, may be prepared in three chemical steps, from custom made or commercially available substituted piperidine derivatives according to Formula (V), alkyl halides or sulfonyl chlorides according to Formula (IV) and alkyl halides of Formula (VI) and hydrazine derivatives according to Formula (II), following the synthetic protocol outlined in Scheme 1 above. In a more specific method, a piperidine derivative according to Formula (V) wherein $R^{18}$ is defined as above is treated with an alkylating agent such as alkyl chlorides, bromides, iodides or mesylates, or a sulfonyl chloride wherein $R^3$ is as defined above, in presence of a suitable base, e.g. Triethylamine, di-isopropyl ethyl amine, sodium hydride or potassium carbonate as a base in a suitable solvent, e.g. dichloromethane, N,N-dimethylformamide or tetrahydrofuran, at room temperature or by traditional thermal method or using microwave technology. The intermediate compounds according to Formula (III) are further reacted with a hydrazine derivative according to Formula (II), wherein $R^1$ is as defined above. The pyrazolo derivatives according to Formula (Ib), i.e. of Formula (I) wherein $R^2$ is H, are isolated after cyclation, preferably in a protic solvent, in presence of a base such as sodium methanolate, sodium isopropanolate or the like, using standard refluxing conditions well known to the person skilled in the art as shown in Scheme 1. In a subsequent step, the intermediate compounds of Formula (III) are treated with an alkylating agent of Formula (VI) such as alkyl chlorides, bromides, iodides or mesylates, wherein $R^3$ is as defined above, in presence of a suitable base, e.g. sodium hydride as a base in a suitable solvent, e.g. N,N-dimethylformamide at room temperature or by traditional thermal method depending of the intrinsic reactivity of compounds of Formula (VI). The resulting intermediate compounds according to Formula (VII) are further reacted with hydrazine derivative according to Formula (II), wherein $R^1$ is as defined above. The pyrazolo derivatives according to Formula (I), are isolated after cyclisation, preferably in a protic solvent, in presence of an acid such as acetic acid or the like, using standard refluxing conditions well known to the person skilled in the art as shown in Scheme 1.

The following abbreviations refer respectively to the definitions below:

Å (Angström), min (minute), h (hour), g (gram), MHz (Megahertz), mL (milliliter), mm (millimeter), mmol (millimole), mM (millimolar), ng (nanogram), nm (nanometer), BLM (Bleomycin), BSA (Bovine serum albumin), DCF (2,7-dichlorodihydrofluorescein), DCM (dichloromethane), DMSO (Dimethyl Sulfoxide), DMF (N,N-Dimethylformamide), DAPI (4,6 Diamidino-2-phenylindole), DPI (Diphenyl-iodonium), EDTA (ethylenediamine tetraacetic acid), EGF (Epidermal Growth Factor), EtOAc (Ethyl acetate), FCS (Foetal Calf Serum), HBSS (Hank's Buffered Salt Solution), HPLC (High performance liquid chromatography), H₂DCF-DA (2',7'-dichlorodihydrofluorescein diacetate), MEM (2-methoxyethoxymethyl), MS (Mass Spectrometry), NADPH (Nicotinamide adenine dinucleotide diphosphate reduced form), NBT (Nitroblue tetrazolium), NMR (Nuclear magnetic resonance), PBS (Phosphate Buffered Saline), TFA (Trifluoroacetic acid), TGF-β (Tumor Growth Factor beta), ROS (Reactive oxygen species), SOD (Superoxide dismutase), SPA (Scintillation proximity assay), TLC (Thin layer chromatography), HPLC (ultra performance liquid chromatography), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, 2005 and Theodora W. Greene and Peter G. M. Wuts in "Protective Groups in Organic Synthesis", Wiley Interscience, 4th Edition 2006.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not to be viewed as limiting the scope of the invention.

The HPLC, NMR and MS data provided in the examples described below are obtained as followed: HPLC: column Waters Symmetry C8 50×4.6 mm, Conditions: MeCN/$H_2O$, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak®HR C186 μm 60 Å, 40×30 mm (up to 100 mg) or with XTerra® Prep MS C8, 10 μm, 50×300 mm (up to 1 g). All the purifications are performed with a gradient of MeCN/$H_2O$ 0.09% TFA; UV detection at 254 nm and 220 nm; flow 20 mL/min (up to 50 mg). TLC Analysis is performed on Merck Precoated 60 $F_{254}$ plates. Purifications by flash chromatography are performed on $SiO_2$ support, using cyclohexane/EtOAc or DCM/MeOH mixtures as eluents.

Example 1

Formation of 2-phenyl-5-(pyridin-3-ylmethyl)-1,2,4,5,6,7-hexahydro-3H-pyrazolo[4,3-c]pyridin-3-one (43)(Compound Ib, Scheme 1)

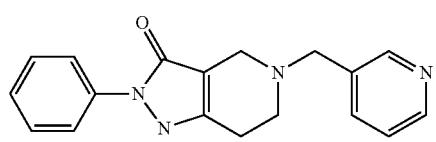

(43)

a) methyl 4-oxo-1-(pyridin-3-ylmethyl)piperidine-3-carboxylate (Compound of Formula (III), Scheme 1)

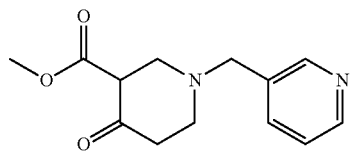 [SMILES: COC(=O)C1CN(Cc2cccnc2)CCC1=O]

0.200 g (1.034 mmol) of 1-methyl-4-oxopiperidine-3-carboxylate hydrochloride (commercially available, ABCR), 0.54 mL (3.102 mmol) of diisopropylethylamine, 0.155 g (1.034 mmol) of sodium iodide and 0.170 g (1.034 mmol) of 3-(chloromethyl)pyridine hydrochloride were stirred at 80° C. in 5.0 mL of anhydrous $CH_3CN$. The reaction was monitored by HPLC and UPLC-MS. After 1 h at 80° C., the insoluble inorganic materials were filtered off and the filtrate was concentrated in vacuo to give a yellowish residue. This residue was dissolved in $CH_2Cl_2$, washed with brine, $H_2O$, dried over $Na_2SO_4$ and concentrated in vacuo to give pure methyl 4-oxo-1-(pyridin-3-ylmethyl)piperidine-3-carboxylate (0.257 g, 1.034 mmol, quantitative yield). The product was used for the next step without further manipulation.

b) 2-phenyl-5-(pyridin-3-ylmethyl)-1,2,4,5,6,7-hexahydro-3H-pyrazolo[4,3-c]pyridin-3-one (Compound of Formula (Ib), Scheme 1)

In a three-necked flask, under a $N_2$ atmosphere, 0.257 g (1.034 mmol) of methyl 4-oxo-1-(pyridin-3-ylmethyl)piperidine-3-carboxylate obtained above and 0.111 g (1.034 mmol) of phenylhydrazine were stirred in 3.50 mL of EtOH for 1 h at 60° C. HPLC and UPLC-MS analyses revealed the formation of the hydrazone intermediate. After cooling to room temperature, a solution of EtONa/EtOH—prepared by dissolution of 48 mg (2.068 mmol) of Na in 3.50 mL of EtOH—was added to the reaction mixture and it was stirred for 1 additional hour at room temperature (reaction monitored by HPLC and UPLC-MS). The crude mixture was then concentrated in vacuo to give a reddish residue that was dissolved in 2.0 mL of $H_2O$ and purified by reverse-phase chromatography ($H_2O$ as eluent, isochratic). Lyophilisation of the pure fractions in the desired product afforded 133 mg of the desired 2-phenyl-5-(pyridin-3-ylmethyl)-1,2,4,5,6,7-hexahydro-3H-pyrazolo[4,3-c]pyridin-3-one as a white solid (42% yield). 1HNMR (500 MHz, DMSO-d6): 2.41 (t, J 5.7 Hz, 1H); 2.59 (t, J 5.7 Hz, 2H); 3.03 (s, 2H); 3.62 (s, 2H); 6.75 (tt, J 7.3, 1.3 Hz, 1H); 7.12 (m, 2H); 7.36 (ddd, J 7.9, 4.7, 0.9 Hz, 1H); 7.74 (dt, J 7.9, 1.9 Hz, 1H); 8.12 (m, 2H); 8.46 (dd, J 4.7, 1.6 Hz, 1H); 8.52 (dd, J 1.9, 0.9 Hz, 1H). 307.2.

Example 2

Formation of 3a-benzyl-5-(4-chlorobenzyl)-2-methyl-2,3a,4,5,6,7-hexahydro-3H-pyrazolo[4,3-c]pyridin-3-one (52)(Compound I, Scheme 1)

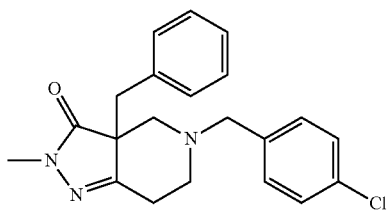

(52)

a) methyl 1-(4-chlorobenzyl)-4-oxopiperidine-3-carboxylate (Compound of Formula (III), Scheme 1)

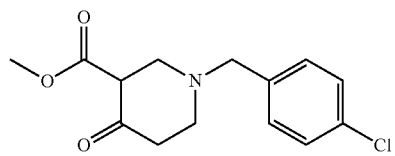 [SMILES: COC(=O)C1CN(Cc2ccc(Cl)cc2)CCC1=O]

0.800 g of methyl 4-oxopiperidine-3-carboxylate hydrochloride (4.134 mmol), 1.44 mL (8.268 mmol) of diisopropylethylamine and 0.852 g (4.134 mmol) of 4-chloro-benzyl bromide were stirred at room temperature in 16.0 mL of anhydrous CH₂Cl₂. The reaction was monitored by HPLC and UPLC-MS. After 16 h at room temperature, brine was added to the reaction mixture. The organic phase was separated, dried over Na₂SO₄ and concentrated in vacuo to give pure methyl methyl 1-(4-chlorobenzyl)-4-oxopiperidine-3-carboxylate (1.164 g, 4.133 mmol, quantitative yield). The product was used for the next step without further manipulation. 282.1.

b) methyl 3-benzyl-1-(4-chlorobenzyl)-4-oxopiperidine-3-carboxylate (Compound of Formula (VII), Scheme 1)

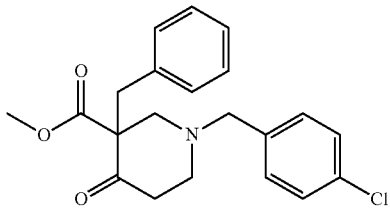 [SMILES: COC(=O)C1(Cc2ccccc2)CN(Cc2ccc(Cl)cc2)CCC1=O]

In a three-necked flask, under a azote atmosphere, sodium hydride (0.115 g, 60% in mineral oil, 2.871 mmol) was added at 0° C. by small portions to a solution of methyl 1-(4-chlorobenzyl)-4-oxopiperidine-3-carboxylate obtained above (0.809 g, 2.871 mmol) in 1.80 mL of anhydrous DMF. The resulting mixture was stirred 30 min at room temperature and then a solution of benzyl bromide (0.341 mL, 2.871 mmol) in 2.20 mL of anhydrous DMF was added. The reaction was followed by HPLC and UPLC-MS. After 24 h at room temperature, it was diluted with ethyl acetate. The organic phase was washed with H₂O, brine, dried over Na₂SO₄ and concentrated in vacuo to give a yellow oil that was purified by flash chromatography (SiO₂, petroleum ether:ethyl acetate 95:5 as eluent). Evaporation and drying in vacuo of the pure fractions gave pure methyl 3-benzyl-1-(4-chlorobenzyl)-4-oxopiperidine-3-carboxylate as a colorless oil. (0.623 g, 1.675 mmol, 58% yield). 372.2.

c) 3a-benzyl-5-(4-chlorobenzyl)-2-methyl-2,3a,4,5,6,7-hexahydro-3H-pyrazolo[4,3-c]pyridin-3-one (Compound of Formula (I), Scheme 1)

In a two-necked flask, under a N₂ atmosphere, 0.200 g (0.538 mmol) of methyl 3-benzyl-1-(4-chlorobenzyl)-4-oxopiperidine-3-carboxylate obtained above and 0.028 mL (0.538 mmol) of methylhydrazine were stirred in 0.9 mL of EtOH for 1 h at 60° C. HPLC and UPLC-MS analyses revealed the formation of the hydrazone intermediate. After cooling to room temperature, 0.062 mL (1.076 mmol) of glacial acetic acid were added. The resulting mixture was stirred at 60° C. and monitored by HPLC and UPLC-MS. After 6 h at 60° C., the crude mixture was partitioned between CH₂Cl₂ and a NaHCO₃ saturated aqueous solution. The organic phase was separated, washed with brine, dried over Na₂SO₄ and concentrated in vacuo to give a yellow oil that was purified by flash chromatography (SiO₂, petroleum ether: ethyl acetate 93:7 as eluent). Evaporation and drying in vacuo of the pure fractions afforded 135 mg (0.367 mmol) of the desired 3a-benzyl-5-(4-chlorobenzyl)-2-methyl-2,3a,4,5,6,7-hexahydro-3H-pyrazolo[4,3-c]pyridin-3-one as a white solid (68% yield). 1HNMR (500 MHz, DMSO-d6): 1.92 (d, J=11.0 Hz, 1H); 2.05 (td, J 11.0, 3.1 Hz, 1H); 2.75-2.81 (m, 1H); 2.89 (d, J=13.2 Hz, 1H); 2.92 (s, 3H); 2.94 (m, 1H); 3.16-3.20 (m, 1H); 3.31 (d, J=13.2 Hz, 1H); 3.50 (d, J=13.2 Hz, 1H); 3.58 (d, J=13.5 Hz, 1H); 3.68 (d, J=13.5 Hz, 1H); 7.04 (m, 2H); 7.16-7.22 (m, 3H); 7.43 (m, 4H). 368.1.

Example 3

Formation of 5-[(4-methylphenyl)sulfonyl]-2-phenyl-1,2,4,5,6,7-hexahydro-3H-pyrazolo[4,3-c]pyridin-3-one (59)(Compound Ib, Scheme I)

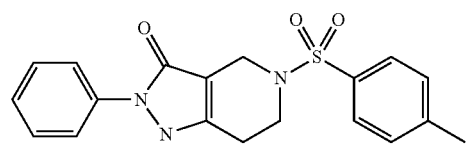

(59)

a) ethyl 1-[(4-methylphenyl)sulfonyl]-4-oxopiperidine-3-carboxylate (Compound of Formula (III), Scheme 1)

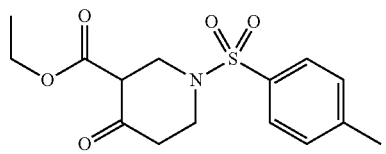 [SMILES: CCOC(=O)C1CN(S(=O)(=O)c2ccc(C)cc2)CCC1=O]

0.200 g (0.97 mmol) of 1-ethyl-4-oxopiperidine-3-carboxylate hydrochloride (commercially available, ABCR) were dissolved in 4 mL of dichloromethane with 0.135 mL (0.97 mmol) of triethylamine. The solution was cooled down to 0° C. and 0.185 g (0.97 mmol) of para-toluenesulfonyl chloride were added followed by 0.135 mL (0.97 mmol) of triethylamine. The reaction was stirred for 20 minutes at 0° C. and overnight at room temperature. Then, the reaction was further diluted with dichloromethane (50 mL) and washed with brine (20 mL×2). The organic layer was dried over Na₂SO₄ and solvent evaporation gave 300 mg of a white solid (95% yield) which was used for the following step without further purification.

b) 5-[(4-methylphenyl)sulfonyl]-2-phenyl-1,2,4,5,6,7-hexahydro-3H-pyrazolo[4,3-c]pyridin-3-one (Compound of Formula (Ib), Scheme 1)

In a three-necked flask, under a N₂ atmosphere, 0.300 g (0.92 mmol) of ethyl 1-[(4-methyl phenyl)sulfonyl]-4-oxopiperidine-3-carboxylate and 0.099 g (0.92 mmol) of phenyl hydrazine were stirred in 3 mL of EtOH for 1 h at 50° C. HPLC and UPLC-MS analysis revealed the formation of the hydrazone intermediate. After having cooled to room temperature, a solution of EtONa/EtOH—prepared by dissolution of 42 mg (1.84 mmol) of Na in 2 mL of EtOH—was added to the reaction mixture and it was stirred for 1 additional hour at room temperature (reaction monitored by HPLC and UPLC-MS). The reaction mixture was diluted with brine (10 mL) and extracted with ethylacetate (50 mL×3). The combined organic phases were dried over Na₂SO₄ and evaporated. The crude (400 mg) was purified by silica flash chromatography using ethylacetate/petroleum ether (80/20, gradient to 100% ethylacetate) yielding 84 mg of a white solid as the desired 5-[(4-methylphenyl)sulfonyl]-2-phenyl-1,2,4,5,6,7-hexahydro-3H-pyrazolo[4,3-c]pyridin-3-one (25% yield). $^1$HNMR (500 MHz, DMSO-d6): 3.95 (s, 3H); 2.64 (t, J=5.5 Hz, 2H); 3.17 (d, J=5 Hz, 2H); 3.30 (m, 2H, hidden by H2O); 7.20 (t, J=7.25 Hz, 1H); 7.40-7.45 (m, 4H); 7.65-7.7 (m, 4H); 11.36 (bs, NH); 370.

The structures of further compounds synthesised herein are listed in the following Table 1:

TABLE 1

| Compound | Structure | Name | Data MS(ESI+) | Method |
|---|---|---|---|---|
| 1 | 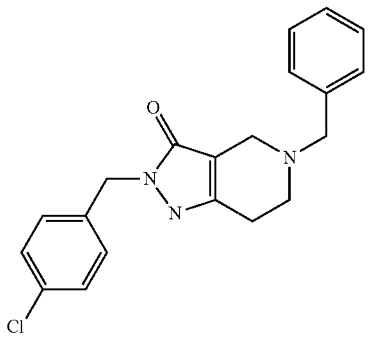 [SMILES: O=c1c2c([nH]n1Cc1ccc(Cl)cc1)CCN(Cc1ccccc1)C2] | 5-benzyl-2-(4-chlorobenzyl)-1,2,4,5,6,7-hexahydro-3H-pyrazolo[4,3-c]pyridin-3-one | 354.9 | Ex. 1, Scheme 1 |
| 2 | 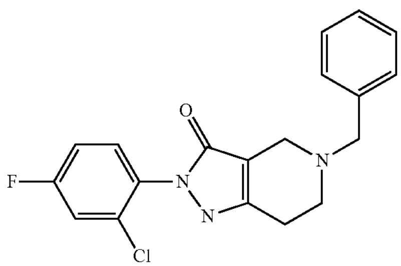 [SMILES: O=c1c2c([nH]n1-c1ccc(F)cc1Cl)CCN(Cc1ccccc1)C2] | 5-benzyl-2-(2-chloro-4-fluorophenyl)-1,2,4,5,6,7-hexahydro-3H-pyrazolo[4,3-c]pyridin-3-one | 358.8 | Ex. 1, Scheme 1 |
| 3 | 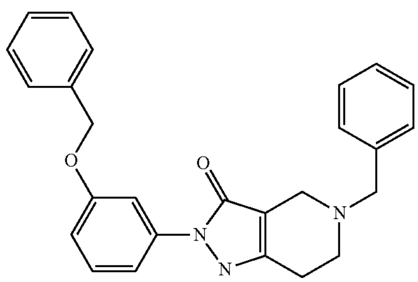 [SMILES: O=c1c2c([nH]n1-c1cccc(OCc3ccccc3)c1)CCN(Cc1ccccc1)C2] | 5-benzyl-2-[3-(benzyloxy)phenyl]-1,2,4,5,6,7-hexahydro-3H-pyrazolo[4,3-c]pyridin-3-one | 412.6 | Ex. 1, Scheme 1 |
| 4 | 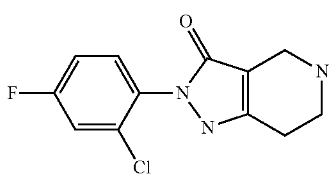 [SMILES: O=c1c2c([nH]n1-c1ccc(F)cc1Cl)CCNC2] | 2-(2-chloro-4-fluorophenyl)-1,2,4,5,6,7-hexahydro-3H-pyrazolo[4,3-c]pyridin-3-one | 268.7 | Ex. 1, Scheme 1 |
| 5 | 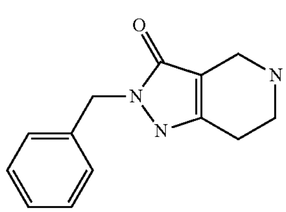 [SMILES: O=c1c2c([nH]n1Cc1ccccc1)CCNC2] | 2-benzyl-1,2,4,5,6,7-hexahydro-3H-pyrazolo[4,3-c]pyridin-3-one | 230.4 | Ex. 1, Scheme 1 |
| 6 | 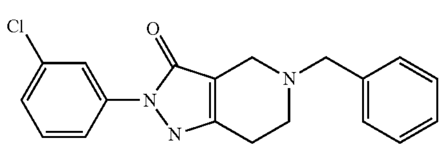 [SMILES: O=c1c2c([nH]n1-c1cccc(Cl)c1)CCN(Cc1ccccc1)C2] | 5-benzyl-2-(3-chlorophenyl)-1,2,4,5,6,7-hexahydro-3H-pyrazolo[4,3-c]pyridin-3-one | 340.7 | Ex. 1, Scheme 1 |

TABLE 1-continued

| Compound | Structure | Name | Data MS(ESI+) | Method |
|---|---|---|---|---|
| 7 | 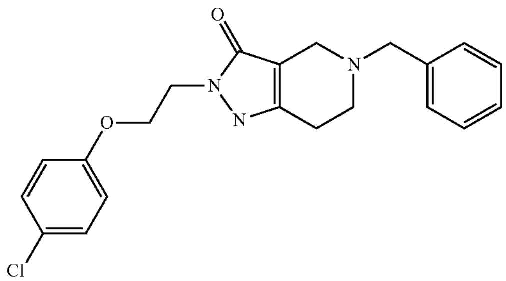 [SMILES: O=c1c2c([nH]n1CCOc1ccc(Cl)cc1)CCN(Cc1ccccc1)C2] | 5-benzyl-2-[2-(4-chlorophenoxy)ethyl]-1,2,4,5,6,7-hexahydro-3H-pyrazolo[4,3-c]pyridin-3-one | 384.9 | Ex. 1, Scheme 1 |
| 8 | 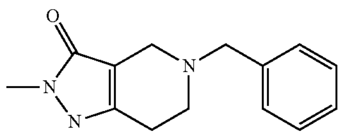 [SMILES: Cn1[nH]c2c(c1=O)CN(Cc1ccccc1)CC2] | 5-benzyl-2-methyl-1,2,4,5,6,7-hexahydro-3H-pyrazolo[4,3-c]pyridin-3-one | 244.5 | Ex. 1, Scheme 1 |
| 9 | 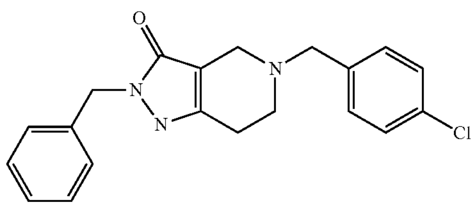 [SMILES: O=c1c2c([nH]n1Cc1ccccc1)CCN(Cc1ccc(Cl)cc1)C2] | 2-benzyl-5-(4-chlorobenzyl)-1,2,4,5,6,7-hexahydro-3H-pyrazolo[4,3-c]pyridin-3-one | 354.9 | Ex. 1, Scheme 1 |
| 10 | 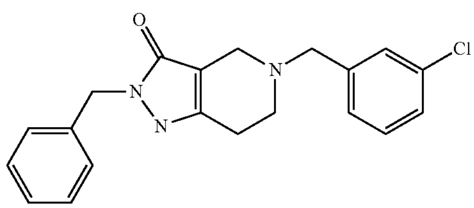 [SMILES: O=c1c2c([nH]n1Cc1ccccc1)CCN(Cc1cccc(Cl)c1)C2] | 2-benzyl-5-(3-chlorobenzyl)-1,2,4,5,6,7-hexahydro-3H-pyrazolo[4,3-c]pyridin-3-one | 354.9 | Ex. 1, Scheme 1 |
| 11 | 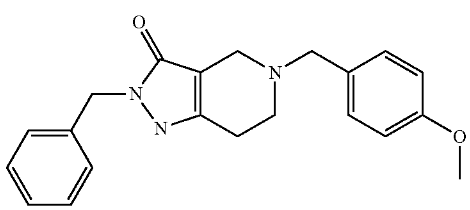 [SMILES: COc1ccc(CN2CCc3[nH]n(Cc4ccccc4)c(=O)c3C2)cc1] | 2-benzyl-5-(4-methoxybenzyl)-1,2,4,5,6,7-hexahydro-3H-pyrazolo[4,3-c]pyridin-3-one | 350.5 | Ex. 1, Scheme 1 |
| 12 | 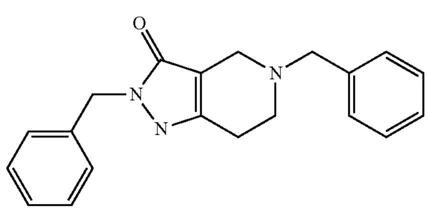 [SMILES: O=c1c2c([nH]n1Cc1ccccc1)CCN(Cc1ccccc1)C2] | 2,5-dibenzyl-1,2,4,5,6,7-hexahydro-3H-pyrazolo[4,3-c]pyridin-3-one | 320.5 | Ex. 1, Scheme 1 |
| 13 | 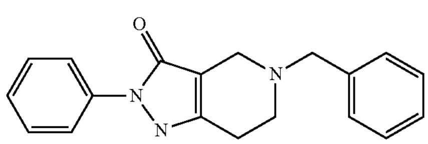 [SMILES: O=c1c2c([nH]n1-c1ccccc1)CCN(Cc1ccccc1)C2] | 5-benzyl-2-phenyl-1,2,4,5,6,7-hexahydro-3H-pyrazolo[4,3-c]pyridin-3-one | 306.5 | Ex. 1, Scheme 1 |
| 14 | 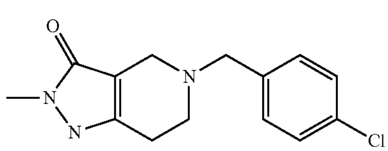 [SMILES: Cn1[nH]c2c(c1=O)CN(Cc1ccc(Cl)cc1)CC2] | 5-(4-chlorobenzyl)-2-methyl-1,2,4,5,6,7-hexahydro-3H-pyrazolo[4,3-c]pyridin-3-one | 278.9 | Ex. 1, Scheme 1 |

TABLE 1-continued

| Compound | Structure | Name | Data MS(ESI+) | Method |
|---|---|---|---|---|
| 15 | 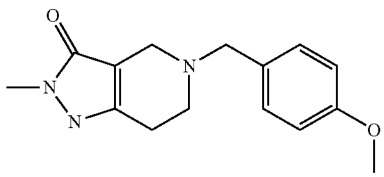 | 5-(4-methoxybenzyl)-2-methyl-1,2,4,5,6,7-hexahydro-3H-pyrazolo[4,3-c]pyridin-3-one | 274.5 | Ex. 1, Scheme 1 |
| 16 | 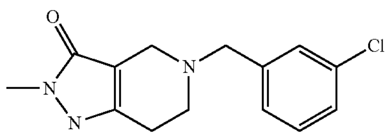 [SMILES: Cn1[nH]c2c(c1=O)CN(Cc1cccc(Cl)c1)CC2] | 5-(3-chlorobenzyl)-2-methyl-1,2,4,5,6,7-hexahydro-3H-pyrazolo[4,3-c]pyridin-3-one | 278.7 | Ex. 1, Scheme 1 |
| 17 | 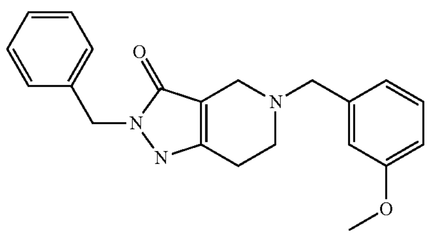 [SMILES: COc1cccc(CN2CCc3[nH]n(Cc4ccccc4)c(=O)c3C2)c1] | 2-benzyl-5-(3-methoxybenzyl)-1,2,4,5,6,7-hexahydro-3H-pyrazolo[4,3-c]pyridin-3-one | 350.4 | Ex. 1, Scheme 1 |
| 18 | 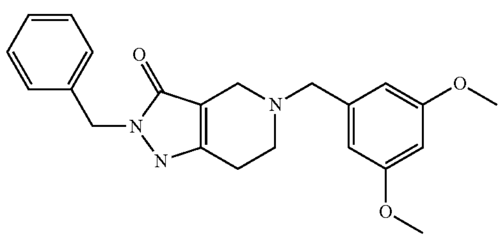 [SMILES: COc1cc(CN2CCc3[nH]n(Cc4ccccc4)c(=O)c3C2)cc(OC)c1] | 2-benzyl-5-(3,5-dimethoxybenzyl)-1,2,4,5,6,7-hexahydro-3H-pyrazolo[4,3-c]pyridin-3-one | 380.6 | Ex. 1, Scheme 1 |
| 19 | 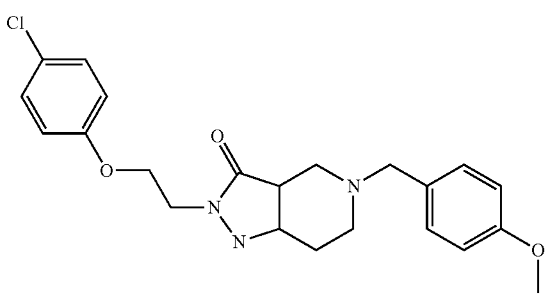 [SMILES: COc1ccc(CN2CCC3NN(CCOc4ccc(Cl)cc4)C(=O)C3C2)cc1] | 2-[2-(4-chlorophenoxy)ethyl]-5-(4-methoxybenzyl)octahydro-3H-pyrazolo[4,3-c]pyridin-3-one | 416.9 | Ex. 1, Scheme 1 |
| 20 | 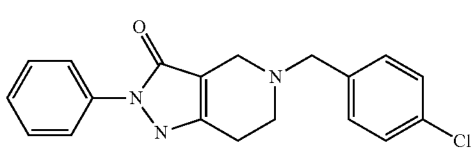 [SMILES: O=c1c2c([nH]n1-c1ccccc1)CCN(Cc1ccc(Cl)cc1)C2] | 5-(4-chlorobenzyl)-2-phenyl-1,2,4,5,6,7-hexahydro-3H-pyrazolo[4,3-c]pyridin-3-one | 340.9 | Ex. 1, Scheme 1 |
| 21 | 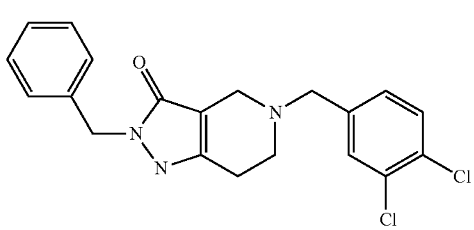 [SMILES: O=c1c2c([nH]n1Cc1ccccc1)CCN(Cc1ccc(Cl)c(Cl)c1)C2] | 2-benzyl-5-(3,4-dichlorobenzyl)-1,2,4,5,6,7-hexahydro-3H-pyrazolo[4,3-c]pyridin-3-one | 389.4 | Ex. 1, Scheme 1 |

TABLE 1-continued

| Compound | Structure | Name | Data MS(ESI+) | Method |
|---|---|---|---|---|
| 22 | 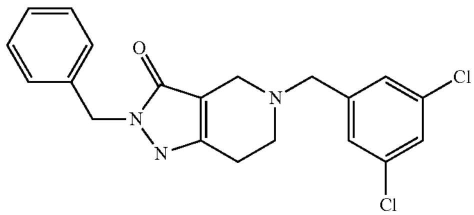 [SMILES: O=c1c2c([nH]n1Cc1ccccc1)CCN(Cc1cc(Cl)cc(Cl)c1)C2] | 2-benzyl-5-(3,5-dichloro-benzyl)-1,2,4,5,6,7-hexahydro-3H-pyrazolo[4,3-c]pyridin-3-one | 389.5 | Ex. 1, Scheme 1 |
| 23 | 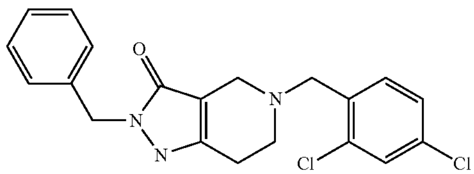 [SMILES: O=c1c2c([nH]n1Cc1ccccc1)CCN(Cc1ccc(Cl)cc1Cl)C2] | 2-benzyl-5-(2,4-dichloro-benzyl)-1,2,4,5,6,7-hexahydro-3H-pyrazolo[4,3-c]pyridin-3-one | 389.4 | Ex. 1, Scheme 1 |
| 24 | 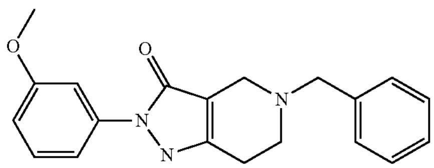 [SMILES: COc1cccc(-n2[nH]c3c(c2=O)CN(Cc2ccccc2)CC3)c1] | 5-benzyl-2-(3-methoxy-phenyl)-1,2,4,5,6,7-hexahydro-3H-pyrazolo[4,3-c]pyridin-3-one | 336.4 | Ex. 1, Scheme 1 |
| 25 | 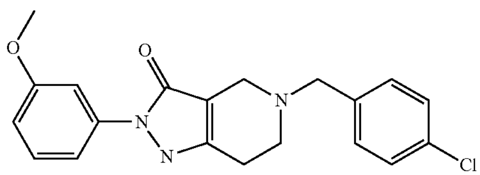 [SMILES: COc1cccc(-n2[nH]c3c(c2=O)CN(Cc2ccc(Cl)cc2)CC3)c1] | 5-(4-chlorobenzyl)-2-(3-methoxyphenyl)-1,2,4,5,6,7-hexahydro-3H-pyrazolo[4,3-c]pyridin-3-one | 371.0 | Ex. 1, Scheme 1 |
| 26 | 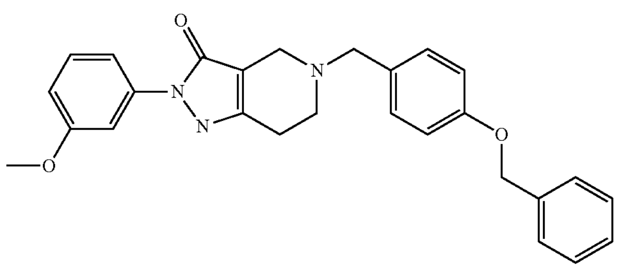 [SMILES: COc1cccc(-n2[nH]c3c(c2=O)CN(Cc2ccc(OCc4ccccc4)cc2)CC3)c1] | 5-[4-(benzyloxy)benzyl]-2-(3-methoxyphenyl)-1,2,4,5,6,7-hexahydro-3H-pyrazolo[4,3-c]pyridin-3-one | 442.6 | Ex. 1, Scheme 1 |
| 27 | 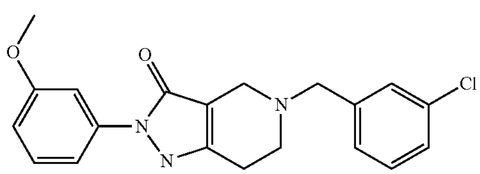 [SMILES: COc1cccc(-n2[nH]c3c(c2=O)CN(Cc2cccc(Cl)c2)CC3)c1] | 5-(3-chlorobenzyl)-2-(3-methoxyphenyl)-1,2,4,5,6,7-hexahydro-3H-pyrazolo[4,3-c]pyridin-3-one | 370.9 | Ex. 1, Scheme 1 |
| 28 | 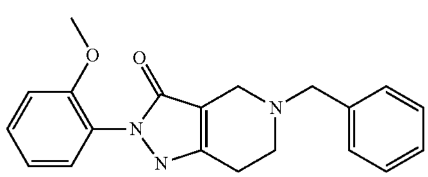 [SMILES: COc1ccccc1-n1[nH]c2c(c1=O)CN(Cc1ccccc1)CC2] | 5-benzyl-2-(2-methoxy-phenyl)-1,2,4,5,6,7-hexahydro-3H-pyrazolo[4,3-c]pyridin-3-one | 336.4 | Ex. 1, Scheme 1 |
| 29 | 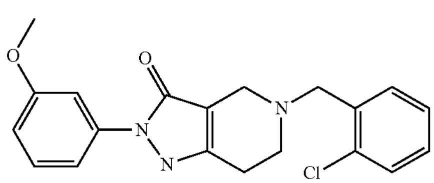 [SMILES: COc1cccc(-n2[nH]c3c(c2=O)CN(Cc2ccccc2Cl)CC3)c1] | 5-(2-chlorobenzyl)-2-(3-methoxyphenyl)-1,2,4,5,6,7-hexahydro-3H-pyrazolo[4,3-c]pyridin-3-one | 371.0 | Ex. 1, Scheme 1 |

TABLE 1-continued

| Compound | Structure | Name | Data MS(ESI+) | Method |
|---|---|---|---|---|
| 30 | 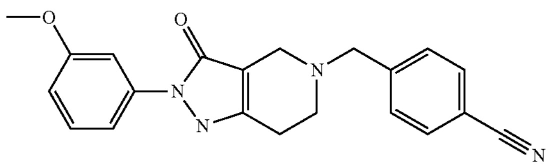 [SMILES: COc1cccc(-n2[nH]c3c(c2=O)CN(Cc2ccc(C#N)cc2)CC3)c1] | 4-{[2-(3-methoxy-phenyl)-3-oxo-1,2,3,4,6,7-hexahydro-5H-pyrazolo[4,3-c]pyridin-5-yl]methyl}benzonitrile | 361.5 | Ex. 1, Scheme 1 |
| 31 | 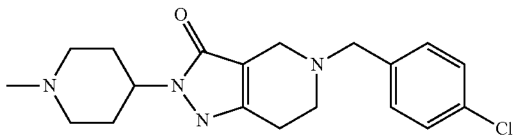 [SMILES: CN1CCC(n2[nH]c3c(c2=O)CN(Cc2ccc(Cl)cc2)CC3)CC1] | 5-(4-chlorobenzyl)-2-(1-methylpiperidin-4-yl)-1,2,4,5,6,7-hexahydro-3H-pyrazolo[4,3-c]pyridin-3-one | 361.9 | Ex. 1, Scheme 1 |
| 32 | 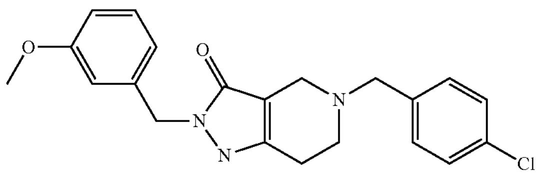 [SMILES: COc1cccc(Cn2[nH]c3c(c2=O)CN(Cc2ccc(Cl)cc2)CC3)c1] | 5-(4-chlorobenzyl)-2-(3-methoxybenzyl)-1,2,4,5,6,7-hexahydro-3H-pyrazolo[4,3-c]pyridin-3-one | 384.9 | Ex. 1, Scheme 1 |
| 33 | 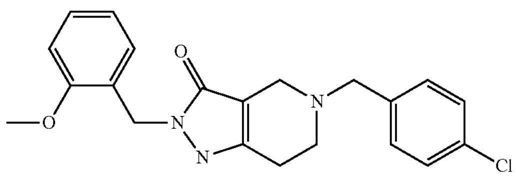 [SMILES: COc1ccccc1Cn1[nH]c2c(c1=O)CN(Cc1ccc(Cl)cc1)CC2] | (4-chlorobenzyl)-2-(2-methoxybenzyl)-1,2,4,5,6,7-hexahydro-3H-pyrazolo[4,3-c]pyridin-3-one | 384.9 | Ex. 1, Scheme 1 |
| 34 | 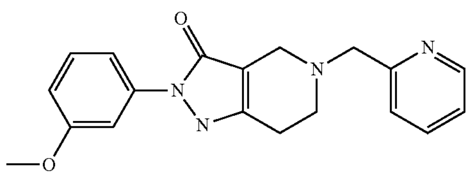 [SMILES: COc1cccc(-n2[nH]c3c(c2=O)CN(Cc2ccccn2)CC3)c1] | 2-(3-methoxyphenyl)-5-(pyridin-2-ylmethyl)-1,2,4,5,6,7-hexahydro-3H-pyrazolo[4,3-c]pyridin-3-one | 337.4 | Ex. 1, Scheme 1 |
| 35 | 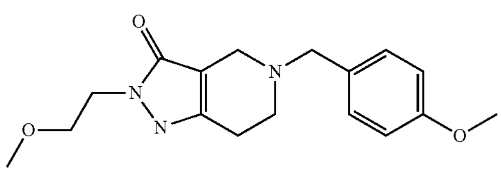 | 5-(4-methoxybenzyl)-2-(2-methoxyethyl)-1,2,4,5,6,7-hexahydro-3H-pyrazolo[4,3-c]pyridin-3-one | 318.4 | Ex. 1, Scheme 1 |
| 36 | 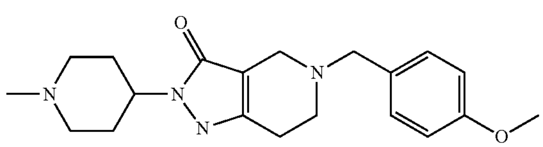 | 5-(4-methoxybenzyl)-2-(1-methylpiperidin-4-yl)-1,2,4,5,6,7-hexahydro-3H-pyrazolo[4,3-c]pyridin-3-one | 357.5 | Ex. 1, Scheme 1 |
| 37 | 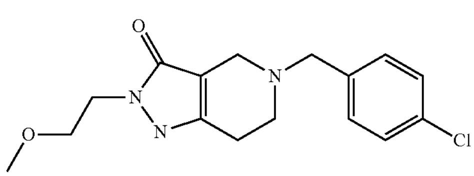 [SMILES: COCCn1[nH]c2c(c1=O)CN(Cc1ccc(Cl)cc1)CC2] | 5-(4-chlorobenzyl)-2-(2-methoxyethyl)-1,2,4,5,6,7-hexahydro-3H-pyrazolo[4,3-c]pyridin-3-one | 322.7 | Ex. 1, Scheme 1 |
| 38 | 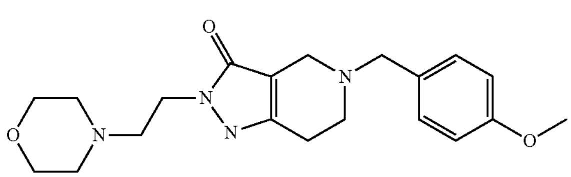 [SMILES: COc1ccc(CN2CCc3[nH]n(CCN4CCOCC4)c(=O)c3C2)cc1] | 5-(4-methoxybenzyl)-2-(2-morpholin-4-ylethyl)-1,2,4,5,6,7-hexahydro-3H-pyrazolo[4,3-c]pyridin-3-one | 373.5 | Ex. 1, Scheme 1 |

TABLE 1-continued

| Compound | Structure | Name | Data MS(ESI+) | Method |
|---|---|---|---|---|
| 39 | 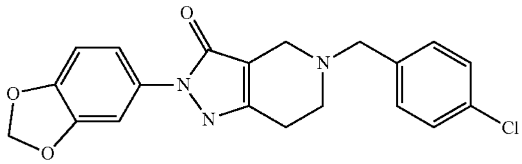 [SMILES: O=c1c2c([nH]n1-c1ccc3c(c1)OCO3)CCN(Cc1ccc(Cl)cc1)C2] | 2-(1,3-benzodioxol-5-yl)-5-(4-chlorobenzyl)-1,2,4,5,6,7-hexahydro-3H-pyrazolo[4,3-c]pyridin-3-one | 384.8 | Ex. 1, Scheme 1 |
| 40 | 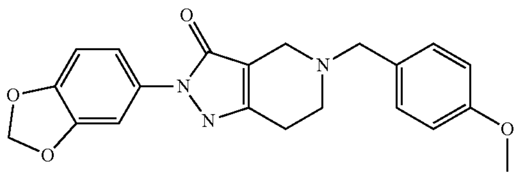 [SMILES: COc1ccc(CN2CCc3[nH]n(-c4ccc5c(c4)OCO5)c(=O)c3C2)cc1] | 2-(1,3-benzodioxol-5-yl)-5-(4-methoxybenzyl)-1,2,4,5,6,7-hexahydro-3H-pyrazolo[4,3-c]pyridin-3-one | 380.5 | Ex. 1, Scheme 1 |
| 41 | 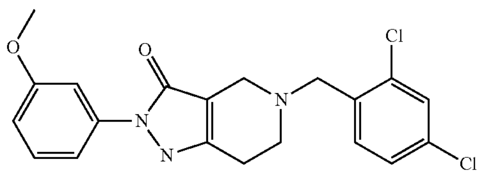 [SMILES: COc1cccc(-n2[nH]c3c(c2=O)CN(Cc2ccc(Cl)cc2Cl)CC3)c1] | 5-(2,4-dichlorobenzyl)-2-(3-methoxyphenyl)-1,2,4,5,6,7-hexahydro-3H-pyrazolo[4,3-c]pyridin-3-one | 405.4 | Ex. 1, Scheme 1 |
| 42 | 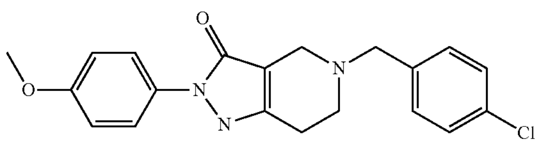 [SMILES: COc1ccc(-n2[nH]c3c(c2=O)CN(Cc2ccc(Cl)cc2)CC3)cc1] | 5-(4-chlorobenzyl)-2-(4-methoxyphenyl)-1,2,4,5,6,7-hexahydro-3H-pyrazolo[4,3-c]pyridin-3-one | 370.9 | Ex. 1, Scheme 1 |
| 43 | 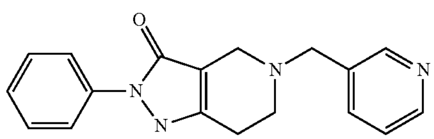 [SMILES: O=c1c2c([nH]n1-c1ccccc1)CCN(Cc1cccnc1)C2] | 2-phenyl-5-(pyridin-3-yl-methyl)-1,2,4,5,6,7-hexahydro-3H-pyrazolo[4,3-c]pyridin-3-one | 307.4 | Ex. 1, Scheme 1 |
| 44 | 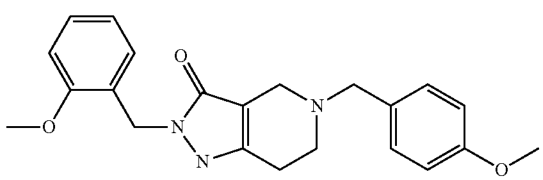 | 2-(2-methoxybenzyl)-5-(4-methoxybenzyl)-1,2,4,5,6,7-hexahydro-3H-pyrazolo[4,3-c]pyridin-3-one | 380.5 | Ex. 1, Scheme 1 |
| 45 | 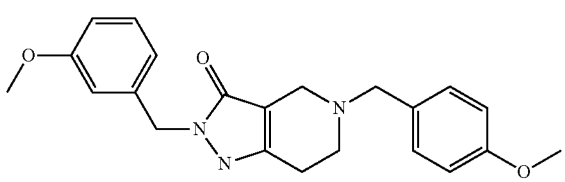 | 2-(3-methoxybenzyl)-5-(4-methoxybenzyl)-1,2,4,5,6,7-hexahydro-3H-pyrazolo[4,3-c]pyridin-3-one | 380.6 | Ex. 1, Scheme 1 |
| 46 | 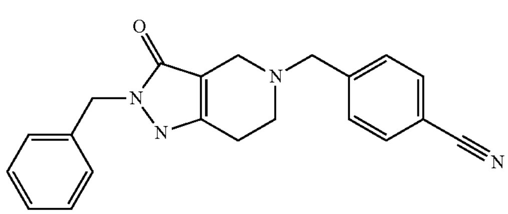 [SMILES: N#Cc1ccc(CN2CCc3[nH]n(Cc4ccccc4)c(=O)c3C2)cc1] | 4-[(2-benzyl-3-oxo-1,2,3,4,6,7-hexahydro-5H-pyrazolo[4,3-c]pyridin-5-yl)methyl]benzonitrile | 345.5 | Ex. 1, Scheme 1 |
| 47 | 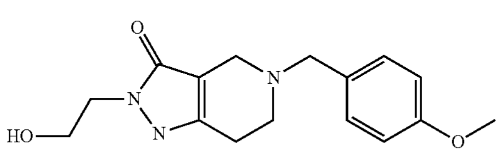 [SMILES: COc1ccc(CN2CCc3[nH]n(CCO)c(=O)c3C2)cc1] | 2-(2-hydroxyethyl)-5-(4-methoxybenzyl)-1,2,4,5,6,7-hexahydro-3H-pyrazolo[4,3-c]pyridin-3-one | 304.4 | Ex. 1, Scheme 1 |

TABLE 1-continued

| Compound | Structure | Name | Data MS(ESI+) | Method |
|---|---|---|---|---|
| 48 | 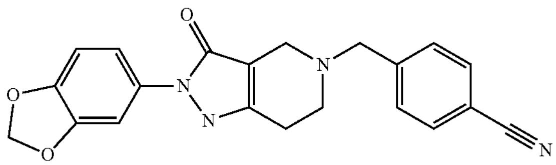 [SMILES: N#Cc1ccc(CN2CCc3[nH]n(-c4ccc5c(c4)OCO5)c(=O)c3C2)cc1] | 4-{[2-(1,3-benzodioxol-5-yl)-3-oxo-1,2,3,4,6,7-hexahydro-5H-pyrazolo[4,3-c]pyridin-5-yl]methyl}benzonitrile | 375.5 | Ex. 1, Scheme 1 |
| 49 | 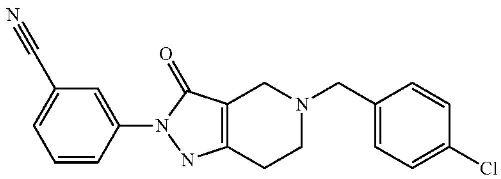 [SMILES: N#Cc1cccc(-n2[nH]c3c(c2=O)CN(Cc2ccc(Cl)cc2)CC3)c1] | 3-[5-(4-chlorobenzyl)-3-oxo-1,3,4,5,6,7-hexahydro-2H-pyrazolo[4,3-c]pyridin-2-yl]benzonitrile | 365.9 | Ex. 1, Scheme 1 |
| 50 | 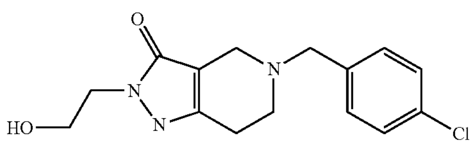 [SMILES: O=c1c2c([nH]n1CCO)CCN(Cc1ccc(Cl)cc1)C2] | 5-(4-chlorobenzyl)-2-(2-hydroxyethyl)-1,2,4,5,6,7-hexahydro-3H-pyrazolo[4,3-c]pyridin-3-one | 308.8 | Ex. 1, Scheme 1 |
| 51 | 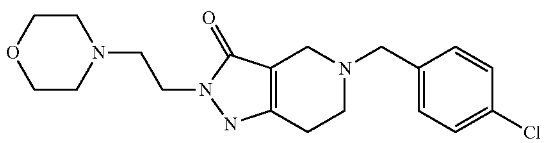 [SMILES: O=c1c2c([nH]n1CCN1CCOCC1)CCN(Cc1ccc(Cl)cc1)C2] | 5-(4-chlorobenzyl)-2-(2-morpholin-4-ylethyl)-1,2,4,5,6,7-hexahydro-3H-pyrazolo[4,3-c]pyridin-3-one | 377.9 | Ex. 1, Scheme 1 |
| 52 | 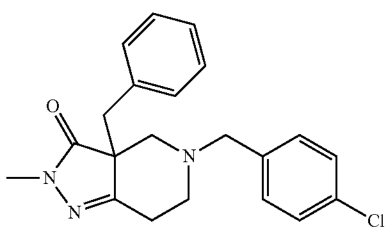 [SMILES: CN1N=C2CCN(Cc3ccc(Cl)cc3)CC2(Cc2ccccc2)C1=O] | 3a-benzyl-5-(4-chlorobenzyl)-2-methyl-2,3a,4,5,6,7-hexahydro-3H-pyrazolo[4,3-c]pyridin-3-one | 368.9 | Ex. 2, Scheme 1 |
| 53 | 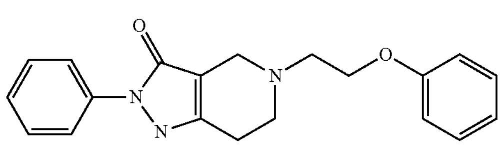 [SMILES: O=c1c2c([nH]n1-c1ccccc1)CCN(CCOc1ccccc1)C2] | 5-(2-phenoxyethyl)-2-phenyl-1,2,4,5,6,7-hexahydro-3H-pyrazolo[4,3-c]pyridin-3-one | 336.5 | Ex. 1, Scheme 1 |
| 54 | 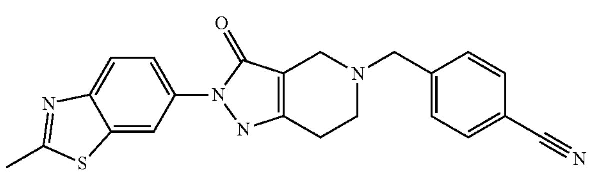 [SMILES: Cc1nc2ccc(-n3[nH]c4c(c3=O)CN(Cc3ccc(C#N)cc3)CC4)cc2s1] | 4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile | 402.5 | Ex. 1, Scheme 1 |
| 55 | 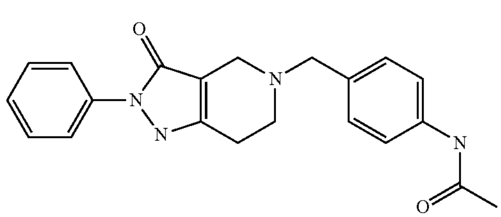 [SMILES: CC(=O)Nc1ccc(CN2CCc3[nH]n(-c4ccccc4)c(=O)c3C2)cc1] | N-{4-[(3-oxo-2-phenyl-1,2,3,4,6,7-hexahydro-5H-pyrazolo[4,3-c]pyridin-5-yl)methyl]phenyl}acetamide | 363.5 | Ex. 1, Scheme 1 |

TABLE 1-continued

| Compound | Structure | Name | Data MS(ESI+) | Method |
|---|---|---|---|---|
| 56 | 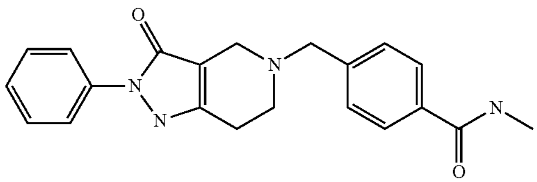 [SMILES: CNC(=O)c1ccc(CN2CCc3[nH]n(-c4ccccc4)c(=O)c3C2)cc1] | N-methyl-4-[(3-oxo-2-phenyl-1,2,3,4,6,7-hexahydro-5H-pyrazolo[4,3-c]pyridin-5-yl)methyl]benzamide | 363.5 | Ex. 1, Scheme 1 |
| 57 | 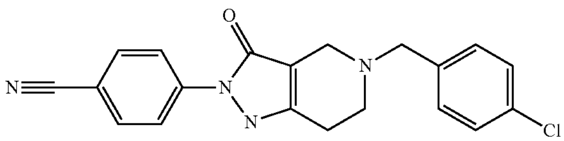 [SMILES: N#Cc1ccc(-n2[nH]c3c(c2=O)CN(Cc2ccc(Cl)cc2)CC3)cc1] | 4-[5-(4-chlorobenzyl)-3-oxo-1,3,4,5,6,7-hexahydro-2H-pyrazolo[4,3-c]pyridin-2-yl]benzonitrile | 365.8 | Ex. 1, Scheme 1 |
| 58 | 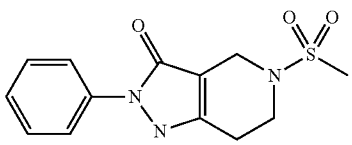 [SMILES: CS(=O)(=O)N1CCc2[nH]n(-c3ccccc3)c(=O)c2C1] | 5-(methylsulfonyl)-2-phenyl-1,2,4,5,6,7-hexahydro-3H-pyrazolo[4,3-c]pyridin-3-one | 294.4 | Ex. 3, Scheme 1 |
| 59 | 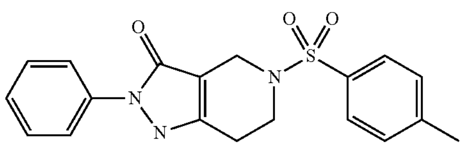 [SMILES: Cc1ccc(S(=O)(=O)N2CCc3[nH]n(-c4ccccc4)c(=O)c3C2)cc1] | 5-[(4-methylphenyl)sulfonyl]-2-phenyl-1,2,4,5,6,7-hexahydro-3H-pyrazolo[4,3-c]pyridin-3-one | 370.4 | Ex. 3, Scheme 1 |
| 60 | 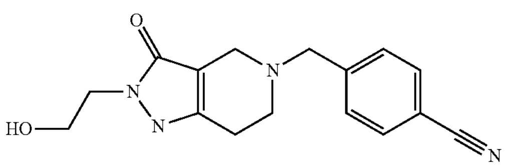 [SMILES: N#Cc1ccc(CN2CCc3[nH]n(CCO)c(=O)c3C2)cc1] | 4-{[2-(2-hydroxyethyl)-3-oxo-1,2,3,4,6,7-hexahydro-5H-pyrazolo[4,3-c]pyridin-5-yl]methyl}benzonitrile | 299.4 | Ex. 1, Scheme 1 |
| 61 | 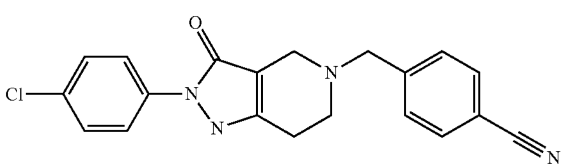 [SMILES: N#Cc1ccc(CN2CCc3[nH]n(-c4ccc(Cl)cc4)c(=O)c3C2)cc1] | 4-{[2-(4-chlorophenyl)-3-oxo-1,2,3,4,6,7-hexahydro-5H-pyrazolo[4,3-c]pyridin-5-yl]methyl}benzonitrile | 365.7 | Ex. 1, Scheme 1 |
| 62 | 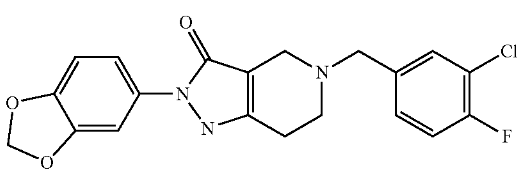 [SMILES: O=c1c2c([nH]n1-c1ccc3c(c1)OCO3)CCN(Cc1ccc(F)c(Cl)c1)C2] | 2-(1,3-benzodioxol-5-yl)-5-(3-chloro-4-fluorobenzyl)-1,2,4,5,6,7-hexahydro-3H-pyrazolo[4,3-c]pyridin-3-one | 402.8 | Ex. 1, Scheme 1 |
| 63 | 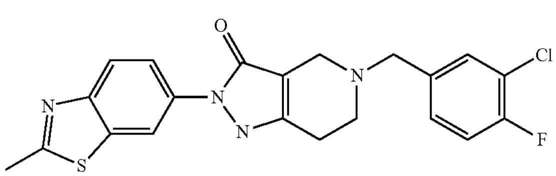 [SMILES: Cc1nc2ccc(-n3[nH]c4c(c3=O)CN(Cc3ccc(F)c(Cl)c3)CC4)cc2s1] | 5-(3-chloro-4-fluorobenzyl)-2-(2-methyl-1,3-benzothiazol-6-yl)-1,2,4,5,6,7-hexahydro-3H-pyrazolo[4,3-c]pyridin-3-one | 429.9 | Ex. 1, Scheme 1 |
| 64 | 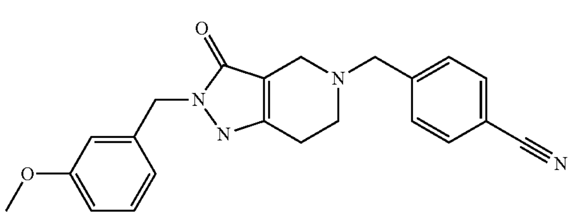 [SMILES: COc1cccc(Cn2[nH]c3c(c2=O)CN(Cc2ccc(C#N)cc2)CC3)c1] | 4-{[2-(3-methoxybenzyl)-3-oxo-1,2,3,4,6,7-hexahydro-5H-pyrazolo[4,3-c]pyridin-5-yl]methyl}benzonitrile | 375.4 | Ex. 1, Scheme 1 |

TABLE 1-continued

| Compound | Name | Data MS(ESI+) | Method |
|---|---|---|---|
| 65 | 2-(2-methyl-1,3-benzo-thiazol-6-yl)-5-[4-(methyl-sulfonyl)benzyl]-1,2,4,5,6,7-hexahydro-3H-pyrazolo[4,3-c]pyridin-3-one | 455.6 | Ex. 1, Scheme 1 |
| 66 | 5-(4-chlorobenzyl)-2-(2-methyl-1,3-benzothiazol-6-yl)-1, 2,4,5,6,7-hexahydro-3H-pyrazolo[4,3-c]pyridin-3-one | 411.9 | Ex. 1, Scheme 1 |
| 67 | 2-benzyl-5-(pyridin-2-yl-methyl)-1,2,4,5,6,7-hexahydro-3H-pyrazolo[4,3-c]pyridin-3-one | 321.4 | Ex. 1, Scheme 1 |
| 68 | 3-{[2-(2-methyl-1,3-benzothiazol-6-yl)-3-oxo-1,2,3,4,6,7-hexahydro-5H-pyrazolo[4,3-c]pyridin-5-yl]methyl}benzonitrile | 402.5 | Ex. 1, Scheme 1 |
| 69 | 2-(2-methyl-1,3-benzothiazol-6-yl)-5-(pyridin-3-ylmethyl)-1,2,4,5,6,7-hexahydro-3H-pyrazolo[4,3-c]pyridin-3-one | 378.6 | Ex. 1, Scheme 1 |
| 70 | 3-[(2-benzyl-3-oxo-1,2,3,4,6,7-hexahydro-5H-pyrazolo[4,3-c]pyridin-5-yl)methyl]benzonitrile | 345.4 | Ex. 1, Scheme 1 |
| 71 | 4-{[2-(4-methoxy-phenyl)-3-oxo-1,2,3,4,6,7-hexahydro-5H-pyrazolo[4,3-c]pyridin-5-yl]methyl}benzonitrile | 361.5 | Ex. 1, Scheme 1 |
| 72 | 3-fluoro-4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile | 420.6 | Ex. 1, Scheme 1 |

TABLE 1-continued

| Compound | Structure | Name | Data MS(ESI+) | Method |
|---|---|---|---|---|
| 73 | 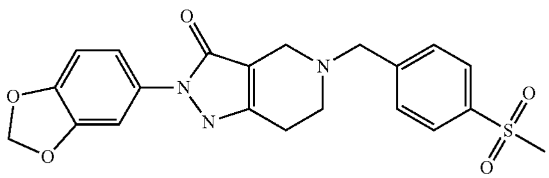 [SMILES: CS(=O)(=O)c1ccc(CN2CCc3[nH]n(-c4ccc5c(c4)OCO5)c(=O)c3C2)cc1] | 2-(1,3-benzodioxol-5-yl)-5-[4-(methylsulfonyl)benzyl]-1,2,4,5,6,7-hexahydro-3H-pyrazolo[4,3-c]pyridin-3-one | 427.4 | Ex. 1, Scheme 1 |
| 74 | 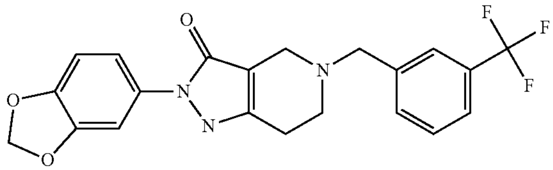 [SMILES: O=c1c2c([nH]n1-c1ccc3c(c1)OCO3)CCN(Cc1cccc(C(F)(F)F)c1)C2] | 2-(1,3-benzodioxol-5-yl)-5-[3-(trifluoromethyl)benzyl]-1,2,4,5,6,7-hexahydro-3H-pyrazolo[4,3-c]pyridin-3-one | 418.5 | Ex. 1, Scheme 1 |
| 75 | 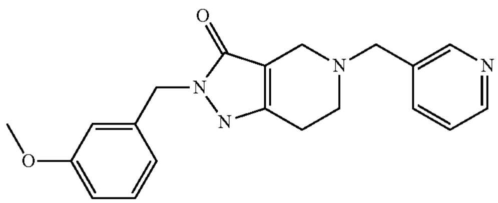 [SMILES: COc1cccc(Cn2[nH]c3c(c2=O)CN(Cc2cccnc2)CC3)c1] | 2-(3-methoxybenzyl)-5-(pyridin-3-ylmethyl)-1,2,4,5,6,7-hexahydro-3H-pyrazolo[4,3-c]pyridin-3-one | 351.5 | Ex. 1, Scheme 1 |
| 76 | 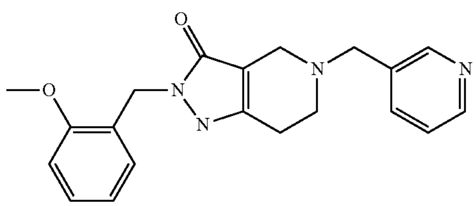 [SMILES: COc1ccccc1Cn1[nH]c2c(c1=O)CN(Cc1cccnc1)CC2] | 2-(2-methoxybenzyl)-5-(pyridin-3-ylmethyl)-1,2,4,5,6,7-hexahydro-3H-pyrazolo[4,3-c]pyridin-3-one | 351.4 | Ex. 1, Scheme 1 |
| 77 | 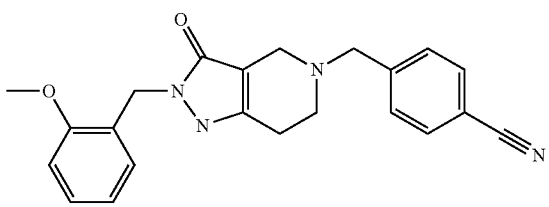 [SMILES: COc1ccccc1Cn1[nH]c2c(c1=O)CN(Cc1ccc(C#N)cc1)CC2] | 4-{[2-(2-methoxybenzyl)-3-oxo-1,2,3,4,6,7-hexahydro-5H-pyrazolo[4,3-c]pyridin-5-yl]methyl}benzonitrile | 375.4 | Ex. 1, Scheme 1 |
| 78 | 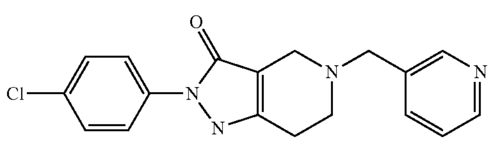 [SMILES: O=c1c2c([nH]n1-c1ccc(Cl)cc1)CCN(Cc1cccnc1)C2] | 2-(4-chlorophenyl)-5-(pyridin-3-ylmethyl)-1,2,4,5,6,7-hexahydro-3H-pyrazolo[4,3-c]pyridin-3-one | 341.8 | Ex. 1, Scheme 1 |
| 79 | 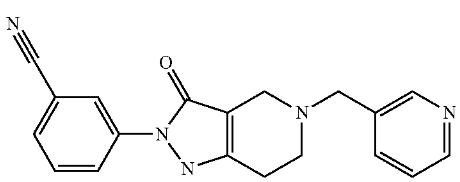 [SMILES: N#Cc1cccc(-n2[nH]c3c(c2=O)CN(Cc2cccnc2)CC3)c1] | 3-[3-oxo-5-(pyridin-3-ylmethyl)-1,3,4,5,6,7-hexahydro-2H-pyrazolo[4,3-c]pyridin-2-yl]benzonitrile | 332.5 | Ex. 1, Scheme 1 |
| 80 | 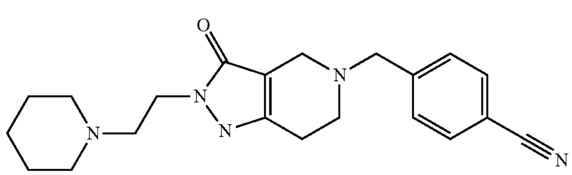 [SMILES: N#Cc1ccc(CN2CCc3[nH]n(CCN4CCCCC4)c(=O)c3C2)cc1] | 4-{[3-oxo-2-(2-piperidin-1-ylethyl)-1,2,3,4,6,7-hexahydro-5H-pyrazolo[4,3-c]pyridin-5-yl]methyl}benzonitrile | 366.6 | Ex. 1, Scheme 1 |

TABLE 1-continued

| Compound | Structure | Name | Data MS(ESI+) | Method |
|---|---|---|---|---|
| 81 | 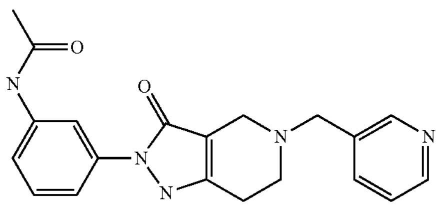 [SMILES: CC(=O)Nc1cccc(-n2[nH]c3c(c2=O)CN(Cc2cccnc2)CC3)c1] | N-{3-[3-oxo-5-(pyridin-3-ylmethyl)-1,3,4,5,6,7-hexahydro-2H-pyrazolo[4,3-c]pyridin-2-yl]phenyl}acetamide | 364.7 | Ex. 1, Scheme 1 |
| 82 | 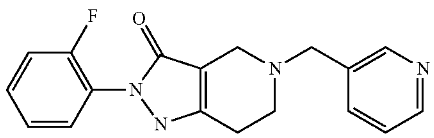 [SMILES: O=c1c2c([nH]n1-c1ccccc1F)CCN(Cc1cccnc1)C2] | 2-(2-fluorophenyl)-5-(pyridin-3-ylmethyl)-1,2,4,5,6,7-hexahydro-3H-pyrazolo[4,3-c]pyridin-3-one | 325.6 | Ex. 1, Scheme 1 |
| 83 | 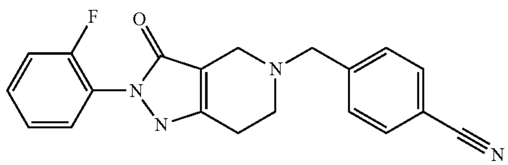 [SMILES: N#Cc1ccc(CN2CCc3[nH]n(-c4ccccc4F)c(=O)c3C2)cc1] | 4-{[2-(2-fluorophenyl)-3-oxo-1,2,3,4,6,7-hexahydro-5H-pyrazolo[4,3-c]pyridin-5-yl]methyl}benzonitrile | 349.5 | Ex. 1, Scheme 1 |
| 84 | 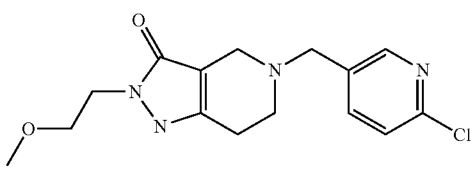 [SMILES: COCCn1[nH]c2c(c1=O)CN(Cc1ccc(Cl)nc1)CC2] | 5-[(6-chloropyridin-3-yl)methyl]-2-(2-methoxyethyl)-1,2,4,5,6,7-hexahydro-3H-pyrazolo[4,3-c]pyridin-3-one | 323.9 | Ex. 1, Scheme 1 |
| 85 | 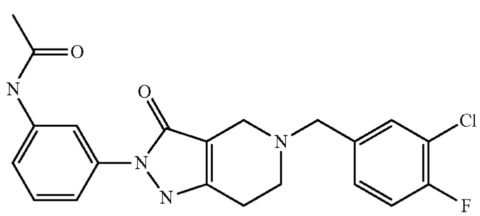 [SMILES: CC(=O)Nc1cccc(-n2[nH]c3c(c2=O)CN(Cc2ccc(F)c(Cl)c2)CC3)c1] | N-{3-[5-(3-chloro-4-fluorobenzyl)-3-oxo-1,3,4,5,6,7-hexahydro-2H-pyrazolo[4,3-c]pyridin-2-yl]phenyl}acetamide | 415.9 | Ex. 1, Scheme 1 |
| 86 | 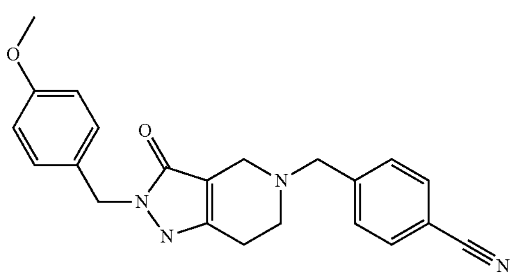 [SMILES: COc1ccc(Cn2[nH]c3c(c2=O)CN(Cc2ccc(C#N)cc2)CC3)cc1] | 4-{[2-(4-methoxybenzyl)-3-oxo-1,2,3,4,6,7-hexahydro-5H-pyrazolo[4,3-c]pyridin-5-yl]methyl}benzonitrile | 375.5 | Ex. 1, Scheme 1 |
| 87 | 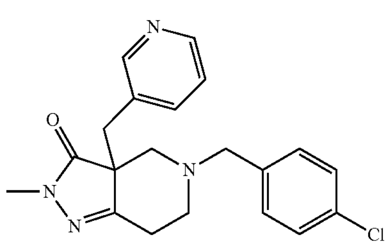 [SMILES: CN1N=C2CCN(Cc3ccc(Cl)cc3)CC2(Cc2cccnc2)C1=O] | 5-(4-chlorobenzyl)-2-methyl-3a-(pyridin-3-ylmethyl)-2,3a,4,5,6,7-hexahydro-3H-pyrazolo[4,3-c]pyridin-3-one | 369.9 | Ex. 2, Scheme 1 |

TABLE 1-continued

| Compound | Structure | Name | Data MS(ESI+) | Method |
|---|---|---|---|---|
| 88 | 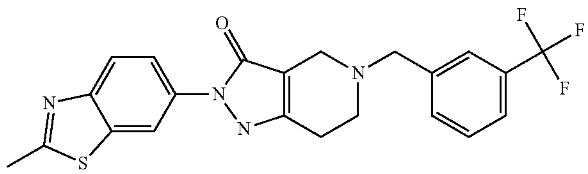 [SMILES: Cc1nc2ccc(-n3[nH]c4c(c3=O)CN(Cc3cccc(C(F)(F)F)c3)CC4)cc2s1] | 2-(2-methyl-1,3-benzothiazol-6-yl)-5-[3-(trifluoromethyl)benzyl]-1,2,4,5,6,7-hexahydro-3H-pyrazolo[4,3-c]pyridin-3-one | 445.7 | Ex. 1, Scheme 1 |
| 89 | 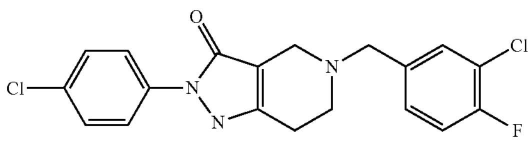 [SMILES: O=c1c2c([nH]n1-c1ccc(Cl)cc1)CCN(Cc1ccc(F)c(Cl)c1)C2] | 5-(3-chloro-4-fluoro-benzyl)-2-(4-chloro-phenyl)-1,2,4,5,6,7-hexahydro-3H-pyrazolo[4,3-c]pyridin-3-one | 393.4 | Ex. 1, Scheme 1 |
| 90 | 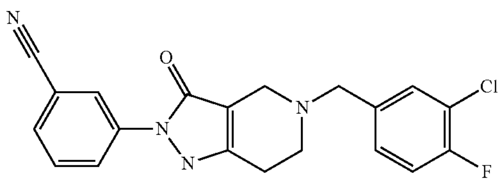 [SMILES: N#Cc1cccc(-n2[nH]c3c(c2=O)CN(Cc2ccc(F)c(Cl)c2)CC3)c1] | 3-[5-(3-chloro-4-fluoro-benzyl)-3-oxo-1,3,4,5,6,7-hexahydro-2H-pyrazolo[4,3-c]pyridin-2-yl]benzonitrile | 383.3 | Ex. 1, Scheme 1 |
| 91 | 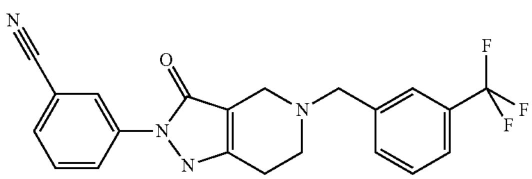 [SMILES: N#Cc1cccc(-n2[nH]c3c(c2=O)CN(Cc2cccc(C(F)(F)F)c2)CC3)c1] | 3-{3-oxo-5-[3-(trifluoro-methyl)benzyl]-1,3,4,5,6,7-hexahydro-2H-pyrazolo[4,3-c]pyridin-2-yl}benzonitrile | 399.6 | Ex. 1, Scheme 1 |
| 92 | 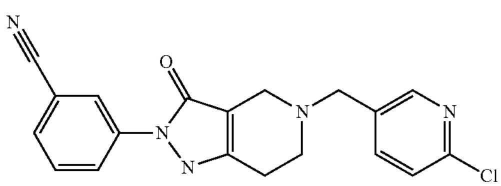 [SMILES: N#Cc1cccc(-n2[nH]c3c(c2=O)CN(Cc2ccc(Cl)nc2)CC3)c1] | 3-{5-[(6-chloropyridin-3-yl)methyl]-3-oxo-1,3,4,5,6,7-hexahydro-2H-pyrazolo[4,3-c]pyridin-2-yl}benzonitrile | 366.4 | Ex. 1, Scheme 1 |
| 93 | 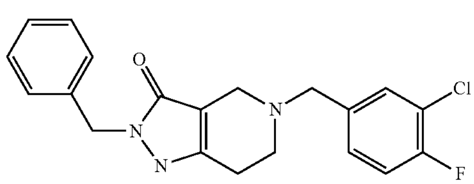 [SMILES: O=c1c2c([nH]n1Cc1ccccc1)CCN(Cc1ccc(F)c(Cl)c1)C2] | 2-benzyl-5-(3-chloro-4-fluorobenzyl)-1,2,4,5,6,7-hexahydro-3H-pyrazolo[4,3-c]pyridin-3-one | 372.5 | Ex. 1, Scheme 1 |
| 94 | 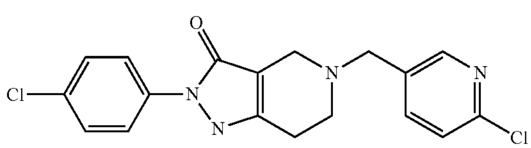 [SMILES: O=c1c2c([nH]n1-c1ccc(Cl)cc1)CCN(Cc1ccc(Cl)nc1)C2] | 2-(4-chlorophenyl)-5-[(6-chloropyridin-3-yl)methyl]-1,2,4,5,6,7-hexahydro-3H-pyrazolo[4,3-c]pyridin-3-one | 376.4 | Ex. 1, Scheme 1 |
| 95 | 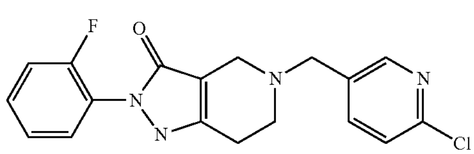 [SMILES: O=c1c2c([nH]n1-c1ccccc1F)CCN(Cc1ccc(Cl)nc1)C2] | 5-[(6-chloropyridin-3-yl)methyl]-2-(2-fluoro-phenyl)-1,2,4,5,6,7-hexahydro-3H-pyrazolo[4,3-c]pyridin-3-one | 359.8 | Ex. 1, Scheme 1 |
| 96 | 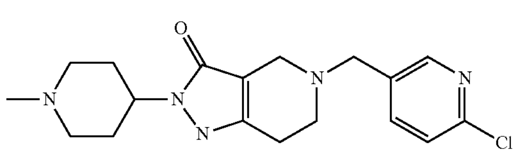 [SMILES: CN1CCC(n2[nH]c3c(c2=O)CN(Cc2ccc(Cl)nc2)CC3)CC1] | 5-[(6-chloropyridin-3-yl)methyl]-2-(1-methyl-piperidin-4-yl)-1,2,4,5,6,7-hexahydro-3H-pyrazolo[4,3-c]pyridin-3-one | 362.6 | Ex. 1, Scheme 1 |

TABLE 1-continued

| Compound | Structure | Name | Data MS(ESI+) | Method |
|---|---|---|---|---|
| 97 | 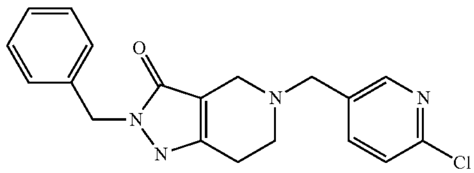 [SMILES: O=c1c2c([nH]n1Cc1ccccc1)CCN(Cc1ccc(Cl)nc1)C2] | 2-benzyl-5-[(6-chloro-pyridin-3-yl)methyl]-1,2,4,5,6,7-hexahydro-3H-pyrazolo[4,3-c]pyridin-3-one | 355.3 | Ex. 1, Scheme 1 |
| 98 | 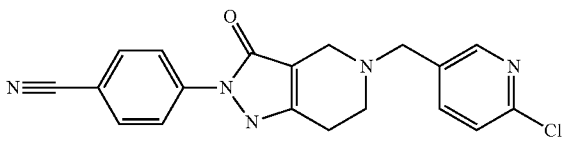 [SMILES: N#Cc1ccc(-n2[nH]c3c(c2=O)CN(Cc2ccc(Cl)nc2)CC3)cc1] | 4-{5-[(6-chloropyridin-3-yl)methyl]-3-oxo-1,3,4,5,6,7-hexahydro-2H-pyrazolo[4,3-c]pyridin-2-yl}benzonitrile | 366.2 | Ex. 1, Scheme 1 |
| 99 | 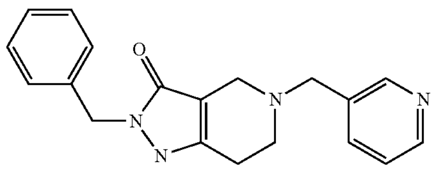 [SMILES: O=c1c2c([nH]n1Cc1ccccc1)CCN(Cc1cccnc1)C2] | 2-benzyl-5-(pyridin-3-ylmethyl)-1,2,4,5,6,7-hexahydro-3H-pyrazolo[4,3-c]pyridin-3-one | 321.3 | Ex. 1, Scheme 1 |
| 100 | 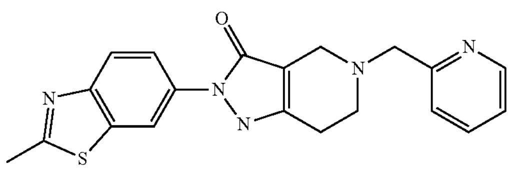 [SMILES: Cc1nc2ccc(-n3[nH]c4c(c3=O)CN(Cc3ccccn3)CC4)cc2s1] | 2-(2-methyl-1,3-benzothiazol-6-yl)-5-(pyridin-2-ylmethyl)-1,2,4,5,6,7-hexahydro-3H-pyrazolo[4,3-c]pyridin-3-one | 378.7 | Ex. 1, Scheme 1 |
| 101 | 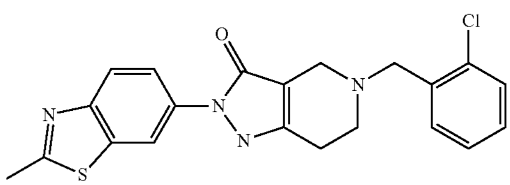 [SMILES: Cc1nc2ccc(-n3[nH]c4c(c3=O)CN(Cc3ccccc3Cl)CC4)cc2s1] | 5-(2-chlorobenzyl)-2-(2-methyl-1,3-benzothiazol-6-yl)-1,2,4,5,6,7-hexahydro-3H-pyrazolo[4,3-c]pyridin-3-one | 411.2 | Ex. 1, Scheme 1 |
| 102 | 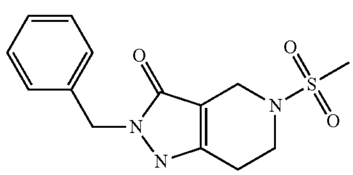 [SMILES: CS(=O)(=O)N1CCc2[nH]n(Cc3ccccc3)c(=O)c2C1] | 2-benzyl-5-(methylsulfonyl)-1,2,4,5,6,7-hexahydro-3H-pyrazolo[4,3-c]pyridin-3-one | 308.8 | Ex. 1, Scheme 1 |
| 103 | 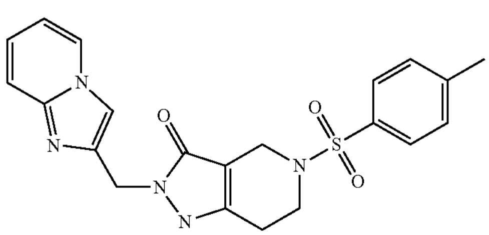 [SMILES: Cc1ccc(S(=O)(=O)N2CCc3[nH]n(Cc4cn5ccccc5n4)c(=O)c3C2)cc1] | 2-(imidazo[1,2-a]pyridin-2-ylmethyl)-5-[(4-methylphenyl)sulfonyl]-1,2,4,5,6,7-hexahydro-3H-pyrazolo[4,3-c]pyridin-3-one | 424.6 | Ex. 1, Scheme 1 |

Example 4

Measurement of Levels of Reactive Oxygen Species in Different Cell Cultures

The activity of the compounds according to the invention may be tested for their activity in the inhibition or reduction of formation of reactive oxygen species (ROS) from oxygen in cells. The activity of the compounds is tested in the following cell cultures by different techniques such as nitroblue tetrazolium, Amplex Red, Chemiluminescence (Luminol) and 2',7'-dichlorodihydrofluorescein diacetate ($H_2$DCF-DA) according to the protocols detailed below.

Human Microglia Cell Line

Human microglia cell line (HMC3, human microglia clone 3) (Janabi et al., 1995, Neurosci. Lett. 195:105) were cultured in MEM (Eagle's minimum essential medium) containing 10% FBS with 50 U/ml penicillin G sodium 50 µg/ml streptomycin sulfate, and incubated at 37° C. for 24 hours. IFN-γ (human IFN-γ, Roche. 11 040 596 001) was added to the culture medium for a final concentration of 10 ng/ml 24 h, before detection of $O_2^-$ formation.

Human Umbilical Vein Endothelial Cells (HUVEC)

HUVEC are cultured in endothelial basal medium supplemented with hydrocortisone (1 μg/mL, Calbiochem), bovine brain extract (12 μg/mL), gentamicin (50 μg/mL, Calbiochem), amphotericin B (50 ng/mL, Calbiochem EGF (10 ng/mL, and 10% FCS until the fourth passage. When the fifth passage was started, cells were cultured with a lower concentration of FCS (2%) in the absence of EGF, if not indicated otherwise. All experiments were done with cells of the fifth passage. The cells were incubated with OxLDL (oxidized low-density lipoprotein) or its buffer as control for 24 h, before detection of $O_2^-$ formation.

HL-60 Cells

Human acute myeloid leukemia cell line HL-60 was cultured in RPMI 1640 (Invitrogen) supplemented with 10% heat-inactivated calf serum, 2 mM glutamine, 100 U/mL penicillin (Sigma), and 100 μg streptomycin (Sigma) at 37° C. under a humidified atmosphere of 5% $CO_2$. HL60 differentiation to the neutrophil phenotype was triggered by adding $Me_2SO$ (final concentration 1.25% v/v for 6 days) to the culture medium.

1. Nitroblue Tetrazolium (NBT)

Intracellular and extracellular superoxide was measured by a colorimetric technique using a quantitative nitroblue tetrazolium (NBT) test. SOD-inhibitable conversion of NBT to formazan, a fine blue precipitate, in the presence of superoxide anion was measured using Fluostar Optima spectrometer (BMG labtech). Following incubation with appropriate stimuli, cells were trypsinized (1× Trypsin-EDTA), collected by centrifugation, and washed with PBS to remove medium. 5×10$^5$ cells were plated on 48-well plates and incubated in Hank's balanced salt solution containing 0.5 mg/mL NBT with or without 800 U/mL SOD in the presence or absence of compounds according to the invention. As a control, DPI was included at a final concentration of 10 μM. After 2.5 h, cells were fixed and washed with methanol to remove non reduced NBT. The reduced formazan was then dissolved in 230 μl of 2M potassium hydroxide and in 280 μl of dimethylsulfoxide. The absorption was measured at 630 nm. For calculation, the absorbance at 630 nm was normalized for each individual well. The mean of the four blank values was subtracted from each corrected value for each time point. NOX activities were expressed as % of the activity in control cells. Residual activity of DPI-treated cells was usually <10%.

2. Amplex Red

Extracellular hydrogen peroxide was measured using Amplex UltraRed (Molecular Probes). Cells were trypsinized (1× Trypsin-EDTA), collected by centrifugation, and resuspended in HBSS supplemented with 1% glucose. Cells were seeded into black 96-well plates at a density of 50'000 cells in 200 μl testing buffer (HBSS 1% glucose containing 0.005 U/mL horseradish peroxidase (Roche) and 50 μM Amplex Red in the presence or absence of compounds according to the invention. As a control, DPI was included at a final concentration of 10 μM The plates were placed in the fluorescent Optima Fluorescent plate reader and kept at 37° C. during 20 min. Fluorescence was measured for 15 min hours with excitation and emission wavelengths of 544 nm and 590 nm respectively. NOX activities were expressed as % of the activity in control cells. Residual activity of DPI-treated cells was usually <10%.

The Table 2 below summarizes the percentage of inhibition of NOX activity as measured by Amplex Red using DMSO-differentiated HL60 cells as described above:

TABLE 2

| Compound n° | Inhibition (%) |
|---|---|
| (1) | 59 |
| (2) | 71 |
| (4) | 84 |
| (8) | 66 |
| (9) | 64 |
| (12) | 61 |
| (17) | 56 |
| (31) | 62 |
| (32) | 62 |
| (34) | 99 |
| (36) | 51 |
| (37) | 64 |
| (39) | 65 |
| (40) | 53 |
| (44) | 57 |
| (48) | 56 |
| (50) | 79 |
| (51) | 70 |
| (52) | 72 |
| (53) | 65 |
| (54) | 61 |
| (55) | 54 |
| (56) | 71 |
| (59) | 83 |
| (60) | 72 |
| (65) | 51 |
| (69) | 51 |
| (72) | 61 |
| (73) | 62 |
| (74) | 57 |
| (87) | 63 |
| (96) | 71 |
| (97) | 62 |
| (102) | 59 |
| (103) | 65 |

The Table 3 below summarizes the $IC_{50}$ of NOX activity as measured by Amplex Red using DMSO-differentiated HL60 cells as described above:

TABLE 3

| Compound n° | $IC_{50}$ (μM) |
|---|---|
| (1) | <5 |
| (2) | <5 |
| (3) | <5 |
| (4) | <5 |
| (8) | <5 |
| (9) | <5 |
| (12) | <5 |
| (24) | <5 |
| (87) | <5 |
| (96) | <5 |
| (97) | <5 |
| (102) | <5 |
| (103) | <5 |

3. Chemiluminescence (Luminol)

ROS was measured using the chemiluminescent probe luminol. Cells were cultured and plated as for Amplex Red except that the Amplex Red agent was replaced by 10 μg/mL luminol (Sigma 09235). Light emission was recorded continuously at 37° C. for 60 minutes using the luminescence function of the FluoStar Optima fluorescent plate reader. The mean of the four blank values was subtracted from each corrected value for each time point. NOX activities were expressed as % of the activity in control cells. Residual activity of DPI-treated cells was usually <10%.

4. 2',7'-dichlorodihydrofluorescein diacetate ($H_2$DCF-DA)

HUVEC were plated on coverslips and made quiescent overnight in 0.5% BSA before stimulation with TGF-β. Cells were loaded for 10 minutes with 5 μM CM-H2DCF-DA in phenol-red-free medium in the dark and then treated with TGF-β (R&D Systems) in the presence or absence of compounds according to the invention. Cells were then visualized by immunofluorescence microscopy after fixation and staining of the nuclei with DAPI or examined live using confocal microscopy. DCF fluorescence was visualized at an excitation wavelength of 488 nm and emission at 515 to 540 nm. To avoid photo-oxidation of the indicator dye, images were collected with a single rapid scan using identical parameters for all samples. For calculation, the absorbance at 540 nm was normalized to absorbance at 540 nm for each individual well. The mean of the four blank values was subtracted from each corrected value for each time point. NOX activities were expressed as % of the activity in control cells. Residual activity of DPI-treated cells was usually <10%.

Example 5

Blood Pressure Measurement in Spontaneous Hypertensive Rats (SHR)

In order to test the ability of compounds according to the invention to treat hypertension, the following assay is carried out.

SHR at 11 weeks of age with systolic blood pressure above 170 mmHg are used. Compound according to the invention are administered orally to rats at a dose of about 3, 10, 30 and 100 mg/kg between 10:00 and 12:00 h. Mean, systolic and diastolic blood pressure and heart rate are monitored 2, 4, 6, 8 and 24 hours after the first administration of a compound according to the invention in order to perform a kinetic analysis over one day. After that, blood pressure is monitored every two days for two weeks, in the morning at 24 h time point and at the half life of the compound.

After the last injection, a 24 hour time point is monitored. The animals are controlled for an additional week without treatment in order to monitor the compound withdrawal. The animals are treated once a day for a period of two weeks by gavage with a special needle adapted for gavage at 5 ml/kg. Before using the animals, they are acclimated for two days and further trained during one week. The blood pressure is measured in awaken rats by tail-cuff plethysmography (Codas 6, Kent). Animals are included into groups after training for several days and if SBP variability was ≤40 mm Hg, i.e. +/−20 min Hg. Baseline measurements were performed at least on two days before the experiment. Before the beginning of the experiment, animals are randomized in order to constitute homogeneous groups.

Example 6

Bleomycine-Induced Lung Injury in Mice

In order to test the ability of compounds according to the invention to prevent or treat respiratory disorder or disease, the following assay is carried out.

In order to produce pulmonary lesion which are comparable to those in respiratory disorder or disease such as idiopathic pulmonary fibrosis, animals receive endotracheally a single sublethal dose of bleomycine (BLM) (2.5 U/kg body weight dissolved in 0.25 ml of 0.9% NaCl). Control animals are subjected to the same protocol but received the same volume of intratracheal saline instead of BLM. Tracheal instillation is carried out under ketamin (80 mg/kg of body weight, i.p.) and xylazine (20 mg/kg de body weight, i.p.) anesthesia.

2 weeks days after endotracheal BLM or saline, the animals are killed by a lethal injection of sodium pentobarbital followed by exsanguination of abdominal aorta. Bronchoalveolar lavage is performed and lungs are weighed and processed separately for biochemical (homogenate right lung, n=10) and histological (left lung, n=10) studies as indicated below. The animals are randomly divided into four groups: control-saline (n=8) and control+BLM (n=10); Compound Dose 1+BLM (n=10) and Compound Dose 2+BLM (N=10). Treatments vehicle or compounds are administered for 2 weeks. Mice are treated by daily oral administration of compound according to the invention or saline/control starting on day 0 for two weeks. Whole lung accumulation of acid-soluble collagen is analyzed by Sircol assay.

Example 7

Animal Models of Cancer

In order to test the ability of compounds according to the invention to treat cancers, in particular to reduce tumour growth and/or angiogenesis, the following assays are carried out.

In Vivo Angiogenesis Assay 7 to 10 weeks old C57BL6/J females are injected subcutaneously with 400 μl of Matrigel growth factor reduced complemented with 500 ng/ml of angiogenic factor (b-FGF or VEGF). One week after the graft, mice are scanned using MicroCT (Skyscan). Mice are injected retro-orbitally with a tracer (400 μl iodated liposomes) to visualize the vessel density. Scan picture are then reconstituted with Recon program and the density of grey in the plug is counted in all the slide of the plug. Compounds of the invention are administered per oral route at the appropriate doses 1 and 2, once-a-day for 10 days. Results are expressed in grey density, which is correlated to vessel density. Matrigel plug are also frozen and stained for CD31 to visualize vessels.

Tumour Growth Assay $5 \cdot 10^5$ Lewis Lung Carcinoma cells (LLC1) are injected subcutaneously in the back of mice. Mice are treated with a compound according to the invention at 40 mg/kg everyday per os. When the control tumour reaches about 1 cm length, mice are sacrificed and tumour are recovered, weight and frozen. For therapeutic assay, mice are injected with LLC1 cells since tumours have grown about 0.5 cm mice are treated and tumour size is assessed every day. After sacrifice, tumour and frozen and sections of tumour are stained with anti-CD31 antibody and ROS level is analyzed.

We claim:

1. A pharmaceutical composition comprising at least one pyrazolo piperidine derivative according to Formula (I) and a pharmaceutically acceptable carrier, diluent or excipient thereof:

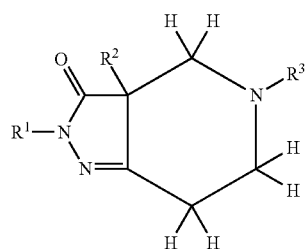

(I)

wherein R¹ is selected from H; optionally substituted alkoxycarbonyl; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl or optionally substituted heterocycloalkyl $C_1$-$C_6$ alkyl; R² is selected from H; optionally substituted $C_1$-$C_6$ alkyl; optionally substituted $C_2$-$C_6$ alkenyl; optionally substituted $C_2$-$C_6$ alkynyl; optionally substituted aryl; optionally substituted heteroaryl; optionally substituted $C_3$-$C_8$-cycloalkyl; optionally substituted heterocycloalkyl; optionally substituted $C_3$-$C_8$-cycloalkyl $C_1$-$C_6$ alkyl; optionally substituted heterocycloalkyl $C_1$-$C_6$ alkyl; optionally substituted aryl $C_1$-$C_6$ alkyl or optionally substituted heteroaryl $C_1$-$C_6$ alkyl; R³ is selected from H, —S(O)—R⁴, —S(O)₂—R⁴, optionally substituted $C_3$-$C_8$-cycloalkyl, optionally substituted heterocycloalkyl and —CR⁵R⁶R⁷; R⁴ is selected from H; optionally substituted amino; optionally substituted $C_1$-$C_6$ alkyl; optionally substituted $C_2$-$C_6$ alkenyl; optionally substituted $C_2$-$C_6$ alkynyl; optionally substituted alkoxy; optionally substituted alkoxy $C_1$-$C_6$ alkyl; optionally substituted aminoalkyl; optionally substituted acyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl or optionally substituted heterocycloalkyl $C_1$-$C_6$ alkyl; R⁵ is selected from H and —CR⁸R⁹R¹⁰; R⁶ is selected from H and —CR¹¹R¹²R¹³; R⁷ is selected from H and —CR¹⁴R¹⁵R¹⁶ and —C(O)—R¹⁷; R⁸, R⁹, R¹⁰, R¹¹, R¹², R¹³, R¹⁴, R¹⁵, R¹⁶ and R¹⁷ are independently selected from H; halogen; optionally substituted amino; optionally substituted acyl; optionally substituted $C_1$-$C_6$ alkyl; optionally substituted $C_2$-$C_6$ alkenyl; optionally substituted $C_2$-$C_6$ alkynyl; optionally substituted aryl; optionally substituted $C_1$-$C_6$ alkyl aryl; optionally substituted aryl $C_1$-$C_6$ alkyl; optionally substituted heteroaryl; optionally substituted $C_1$-$C_6$ alkyl heteroaryl; optionally substituted heteroaryl $C_1$-$C_6$ alkyl; optionally substituted $C_2$-$C_6$ alkenyl aryl; optionally substituted aryl $C_2$-$C_6$ alkenyl; optionally substituted $C_2$-$C_6$ alkenyl heteroaryl; optionally substituted heteroaryl $C_2$-$C_6$ alkenyl; optionally substituted $C_3$-$C_8$-cycloalkyl; optionally substituted heterocycloalkyl; optionally substituted $C_1$-$C_6$ alkyl $C_3$-$C_8$-cycloalkyl; optionally substituted $C_3$-$C_8$-cycloalkyl $C_1$-$C_6$ alkyl; optionally substituted $C_1$-$C_6$ alkyl heterocycloalkyl or optionally substituted heterocycloalkyl $C_1$-$C_6$ alkyl; —CR⁸R⁹R¹⁰, —CR¹¹R¹²R¹³ or —CR¹⁴R¹⁵R¹⁶ can independently form an optionally substituted ring selected from an optionally substituted aryl; an optionally substituted heteroaryl; an optionally substituted $C_3$-$C_8$-cycloalkyl or an optionally substituted heterocycloalkyl; or tautomers, geometrical isomers, optically active forms, and pharmaceutically acceptable salts and thereof.

2. The composition according to claim 1, wherein the pyrazolo piperidine derivative is a tautomer of the compound according to Formula (I) selected from a tautomer of Formula (Ia) and a tautomer of Formula (Ib):

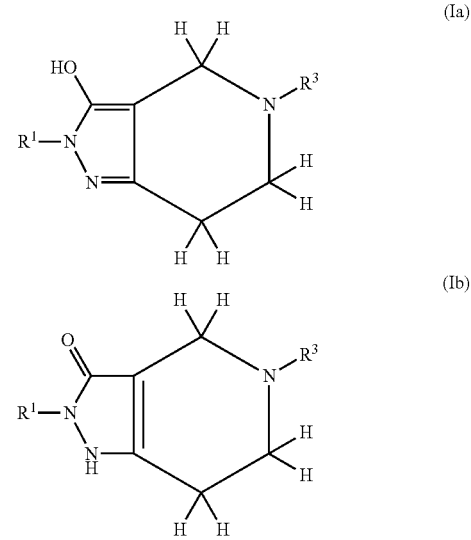

as well as optically active forms and, pharmaceutically acceptable salts thereof, wherein R¹, R³, R⁴, R⁵, R⁶, R⁷, R⁸, R⁹, R¹⁰, R¹¹, R¹², R¹³, R¹⁴, R¹⁵, R¹⁶ and R¹⁷ are as defined in claim 1.

3. The composition according to claim 1, wherein R¹ is selected from optionally substituted aryl or optionally substituted heteroaryl.

4. The composition according to claim 1, wherein R¹ is selected from optionally substituted $C_1$-$C_6$ alkyl; optionally substituted $C_2$-$C_6$ alkenyl; or optionally substituted $C_2$-$C_6$ alkynyl.

5. The composition according to claim 1, wherein R¹ is selected from optionally substituted aryl $C_1$-$C_6$ alkyl or optionally substituted heteroaryl $C_1$-$C_6$ alkyl.

6. The composition according to claim 1, wherein $R^1$ is optionally substituted heterocycloalkyl.

7. The composition according to claim 1, wherein $R^1$ is optionally substituted heterocycloalkyl $C_1$-$C_6$ alkyl.

8. The composition according to claim 1, wherein $R^1$ is optionally substituted alkoxy $C_1$-$C_6$ alkyl.

9. The composition according to claim 1, wherein $R^2$ is H.

10. The composition according to claim 1, wherein $R^2$ is selected from optionally substituted aryl $C_1$-$C_6$ alkyl or optionally substituted heteroaryl $C_1$-$C_6$ alkyl.

11. The composition according to claim 1, wherein $R^3$ is —$CR^5R^6R^7$.

12. The composition according to claim 1, wherein $R^3$ is $S(O)_2$—$R^4$.

13. The composition according to claim 12, wherein $R^3$ is $S(O)_2$—$R^4$ and $R^4$ is selected from optionally substituted $C_1$-$C_6$ alkyl; optionally substituted $C_2$-$C_6$ alkenyl or optionally substituted $C_2$-$C_6$ alkynyl.

14. The composition according to claim 12, wherein $R^3$ is $S(O)_2$—$R^4$ and $R^4$ is selected from optionally substituted aryl or optionally substituted heteroaryl.

15. The composition according to claim 2, wherein the pyrazolo piperidine derivative is selected from the group consisting of:

5-benzyl-2-(4-chlorobenzyl)-1,2,4,5,6,7-hexahydro-3H-pyrazolo[4,3-c]pyridin-3-one;
5-benzyl-2-(2-chloro-4-fluorophenyl)-1,2,4,5,6,7-hexahydro-3H-pyrazolo[4,3-c]pyridin-3-one;
5-benzyl-2-[3-(benzyloxy)phenyl]-1,2,4,5,6,7-hexahydro-3H-pyrazolo[4,3-c]pyridin-3-one;
2-(2-chloro-4-fluorophenyl)-1,2,4,5,6,7-hexahydro-3H-pyrazolo[4,3-c]pyridin-3-one;
2-benzyl-1,2,4,5,6,7-hexahydro-3H-pyrazolo[4,3-c]pyridin-3-one;
5-benzyl-2-(3-chlorophenyl)-1,2,4,5,6,7-hexahydro-3H-pyrazolo[4,3-c]pyridin-3-one;
5-benzyl-2-[2-(4-chlorophenoxy)ethyl]-1,2,4,5,6,7-hexahydro-3H-pyrazolo[4,3-c]pyridin-3-one;
5-benzyl-2-methyl-1,2,4,5,6,7-hexahydro-3H-pyrazolo[4,3-c]pyridin-3-one;
2-benzyl-5-(4-chlorobenzyl)-1,2,4,5,6,7-hexahydro-3H-pyrazolo[4,3-c]pyridin-3-one;
2-benzyl-5-(3-chlorobenzyl)-1,2,4,5,6,7-hexahydro-3H-pyrazolo[4,3-c]pyridin-3-one;
2-benzyl-5-(4-methoxybenzyl)-1,2,4,5,6,7-hexahydro-3H-pyrazolo[4,3-c]pyridin-3-one;
2,5-dibenzyl-1,2,4,5,6,7-hexahydro-3H-pyrazolo[4,3-c]pyridin-3-one;
5-benzyl-2-phenyl-1,2,4,5,6,7-hexahydro-3H-pyrazolo[4,3-c]pyridin-3-one;
5-(4-chlorobenzyl)-2-methyl-1,2,4,5,6,7-hexahydro-3H-pyrazolo[4,3-c]pyridin-3-one;
5-(4-methoxybenzyl)-2-methyl-1,2,4,5,6,7-hexahydro-3H-pyrazolo[4,3-c]pyridin-3-one;
5-(3-chlorobenzyl)-2-methyl-1,2,4,5,6,7-hexahydro-3H-pyrazolo[4,3-c]pyridin-3-one;
2-benzyl-5-(3-methoxybenzyl)-1,2,4,5,6,7-hexahydro-3H-pyrazolo[4,3-c]pyridin-3-one;
2-benzyl-5-(3,5-dimethoxybenzyl)-1,2,4,5,6,7-hexahydro-3H-pyrazolo[4,3-c]pyridin-3-one;
2-[2-(4-chlorophenoxy)ethyl]-5-(4-methoxybenzyl)octahydro-3H-pyrazolo[4,3-c]pyridin-3-one;
5-(4-chlorobenzyl)-2-phenyl-1,2,4,5,6,7-hexahydro-3H-pyrazolo[4,3-c]pyridin-3-one;
2-benzyl-5-(3,4-dichlorobenzyl)-1,2,4,5,6,7-hexahydro-3H-pyrazolo[4,3-c]pyridin-3-one;
2-benzyl-5-(3,5-dichlorobenzyl)-1,2,4,5,6,7-hexahydro-3H-pyrazolo[4,3-c]pyridin-3-one;
2-benzyl-5-(2,4-dichlorobenzyl)-1,2,4,5,6,7-hexahydro-3H-pyrazolo[4,3-c]pyridin-3-one;
5-benzyl-2-(3-methoxyphenyl)-1,2,4,5,6,7-hexahydro-3H-pyrazolo[4,3-c]pyridin-3-one;
5-(4-chlorobenzyl)-2-(3-methoxyphenyl)-1,2,4,5,6,7-hexahydro-3H-pyrazolo[4,3-c]pyridin-3-one;
5-[4-(benzyloxy)benzyl]-2-(3-methoxyphenyl)-1,2,4,5,6,7-hexahydro-3H-pyrazolo[4,3-c]pyridin-3-one;
5-(3-chlorobenzyl)-2-(3-methoxyphenyl)-1,2,4,5,6,7-hexahydro-3H-pyrazolo[4,3-c]pyridin-3-one;
5-benzyl-2-(2-methoxyphenyl)-1,2,4,5,6,7-hexahydro-3H-pyrazolo[4,3-c]pyridin-3-one;
5-(2-chlorobenzyl)-2-(3-methoxyphenyl)-1,2,4,5,6,7-hexahydro-3H-pyrazolo[4,3-c]pyridin-3-one;
4-{[2-(3-methoxyphenyl)-3-oxo-1,2,3,4,6,7-hexahydro-5H-pyrazolo[4,3-c]pyridin-5-yl]methyl}benzonitrile;
5-(4-chlorobenzyl)-2-(1-methylpiperidin-4-yl)-1,2,4,5,6,7-hexahydro-3H-pyrazolo[4,3-c]pyridin-3-one;
5-(4-chlorobenzyl)-2-(3-methoxybenzyl)-1,2,4,5,6,7-hexahydro-3H-pyrazolo[4,3-c]pyridin-3-one;
5-(4-chlorobenzyl)-2-(2-methoxybenzyl)-1,2,4,5,6,7-hexahydro-3H-pyrazolo[4,3-c]pyridin-3-one;
2-(3-methoxyphenyl)-5-(pyridin-2-ylmethyl)-1,2,4,5,6,7-hexahydro-3H-pyrazolo[4,3-c]pyridin-3-one;
5-(4-methoxybenzyl)-2-(2-methoxyethyl)-1,2,4,5,6,7-hexahydro-3H-pyrazolo[4,3-c]pyridin-3-one;
5-(4-methoxybenzyl)-2-(1-methylpiperidin-4-yl)-1,2,4,5,6,7-hexahydro-3H-pyrazolo[4,3-c]pyridin-3-one;
5-(4-chlorobenzyl)-2-(2-methoxyethyl)-1,2,4,5,6,7-hexahydro-3H-pyrazolo[4,3-c]pyridin-3-one;
5-(4-methoxybenzyl)-2-(2-morpholin-4-ylethyl)-1,2,4,5,6,7-hexahydro-3H-pyrazolo[4,3-c]pyridin-3-one;
2-(1,3-benzodioxol-5-yl)-5-(4-chlorobenzyl)-1,2,4,5,6,7-hexahydro-3H-pyrazolo[4,3-c]pyridin-3-one;
2-(1,3-benzodioxol-5-yl)-5-(4-methoxybenzyl)-1,2,4,5,6,7-hexahydro-3H-pyrazolo[4,3-c]pyridin-3-one;
5-(2,4-dichlorobenzyl)-2-(3-methoxyphenyl)-1,2,4,5,6,7-hexahydro-3H-pyrazolo[4,3-c]pyridin-3-one;
5-(4-chlorobenzyl)-2-(4-methoxyphenyl)-1,2,4,5,6,7-hexahydro-3H-pyrazolo[4,3-c]pyridin-3-one;
2-phenyl-5-(pyridin-3-ylmethyl)-1,2,4,5,6,7-hexahydro-3H-pyrazolo[4,3-c]pyridin-3-one;
2-(2-methoxybenzyl)-5-(4-methoxybenzyl)-1,2,4,5,6,7-hexahydro-3H-pyrazolo[4,3-c]pyridin-3-one;
2-(3-methoxybenzyl)-5-(4-methoxybenzyl)-1,2,4,5,6,7-hexahydro-3H-pyrazolo[4,3-c]pyridin-3-one;
4-[(2-benzyl-3-oxo-1,2,3,4,6,7-hexahydro-5H-pyrazolo[4,3-c]pyridin-5-yl)methyl]benzonitrile;
2-(2-hydroxyethyl)-5-(4-methoxybenzyl)-1,2,4,5,6,7-hexahydro-3H-pyrazolo[4,3-c]pyridin-3-one;
4-{[2-(1,3-benzodioxol-5-yl)-3-oxo-1,2,3,4,6,7-hexahydro-5H-pyrazolo[4,3-c]pyridin-5-yl]methyl}benzonitrile;
3-[5-(4-chlorobenzyl)-3-oxo-1,3,4,5,6,7-hexahydro-2H-pyrazolo[4,3-c]pyridin-2-yl]benzonitrile;
5-(4-chlorobenzyl)-2-(2-hydroxyethyl)-1,2,4,5,6,7-hexahydro-3H-pyrazolo[4,3-c]pyridin-3-one;
5-(4-chlorobenzyl)-2-(2-morpholin-4-ylethyl)-1,2,4,5,6,7-hexahydro-3H-pyrazolo[4,3-c]pyridin-3-one;
3a-benzyl-5-(4-chlorobenzyl)-2-methyl-2,3a,4,5,6,7-hexahydro-3H-pyrazolo[4,3-c]pyridin-3-one;
5-(2-phenoxyethyl)-2-phenyl-1,2,4,5,6,7-hexahydro-3H-pyrazolo[4,3-c]pyridin-3-one;

4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;

N-{4-[(3-oxo-2-phenyl-1,2,3,4,6,7-hexahydro-5H-pyrazolo[4,3-c]pyridin-5-yl)methyl]phenyl}acetamide;

N-methyl-4-[(3-oxo-2-phenyl-1,2,3,4,6,7-hexahydro-5H-pyrazolo[4,3-c]pyridin-5-yl)methyl]benzamide;

4-[5-(4-chlorobenzyl)-3-oxo-1,3,4,5,6,7-hexahydro-2H-pyrazolo[4,3-c]pyridin-2-yl]benzonitrile;

5-(methylsulfonyl)-2-phenyl-1,2,4,5,6,7-hexahydro-3H-pyrazolo[4,3-c]pyridin-3-one;

5-[(4-methylphenyl)sulfonyl]-2-phenyl-1,2,4,5,6,7-hexahydro-3H-pyrazolo[4,3-c]pyridin-3-one;

4-{[2-(2-hydroxyethyl)-3-oxo-1,2,3,4,6,7-hexahydro-5H-pyrazolo[4,3-c]pyridin-5-yl]methyl}benzonitrile;

4-{[2-(4-chlorophenyl)-3-oxo-1,2,3,4,6,7-hexahydro-5H-pyrazolo[4,3-c]pyridin-5-yl]methyl}benzonitrile;

2-(1,3-benzodioxol-5-yl)-5-(3-chloro-4-fluorobenzyl)-1,2,4,5,6,7-hexahydro-3H-pyrazolo[4,3-c]pyridin-3-one;

5-(3-chloro-4-fluorobenzyl)-2-(2-methyl-1,3-benzothiazol-6-yl)-1,2,4,5,6,7-hexahydro-3H-pyrazolo[4,3-c]pyridin-3-one;

4-{[2-(3-methoxybenzyl)-3-oxo-1,2,3,4,6,7-hexahydro-5H-pyrazolo[4,3-c]pyridin-5-yl]methyl}benzonitrile;

2-(2-methyl-1,3-benzothiazol-6-yl)-5-[4-(methylsulfonyl)benzyl]-1,2,4,5,6,7-hexahydro-3H-pyrazolo[4,3-c]pyridin-3-one;

5-(4-chlorobenzyl)-2-(2-methyl-1,3-benzothiazol-6-yl)-1,2,4,5,6,7-hexahydro-3H-pyrazolo[4,3-c]pyridin-3-one;

2-benzyl-5-(pyridin-2-ylmethyl)-1,2,4,5,6,7-hexahydro-3H-pyrazolo[4,3-c]pyridin-3-one;

3-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;

2-(2-methyl-1,3-benzothiazol-6-yl)-5-(pyridin-3-ylmethyl)-1,2,4,5,6,7-hexahydro-3H-pyrazolo[4,3-c]pyridin-3-one;

3-[(2-benzyl-3-oxo-1,2,3,4,6,7-hexahydro-5H-pyrazolo[4,3-c]pyridin-5-yl)methyl]benzonitrile;

4-{[2-(4-methoxyphenyl)-3-oxo-1,2,3,4,6,7-hexahydro-5H-pyrazolo[4,3-c]pyridin-5-yl]methyl}benzonitrile;

3-fluoro-4-{[2-(2-methyl-1,3-benzothiazol-6-yl)-3-oxo-1,2,3,4,6,7-hexahydro-5H-pyrazolo[4,3-c]pyridin-5-yl]methyl}benzonitrile;

2-(1,3-benzodioxol-5-yl)-5-[4-(methylsulfonyl)benzyl]-1,2,4,5,6,7-hexahydro-3H-pyrazolo[4,3-c]pyridin-3-one;

2-(1,3-benzodioxol-5-yl)-5-[3-(trifluoromethyl)benzyl]-1,2,4,5,6,7-hexahydro-3H-pyrazolo[4,3-c]pyridin-3-one;

2-(3-methoxybenzyl)-5-(pyridin-3-ylmethyl)-1,2,4,5,6,7-hexahydro-3H-pyrazolo[4,3-c]pyridin-3-one;

2-(2-methoxybenzyl)-5-(pyridin-3-ylmethyl)-1,2,4,5,6,7-hexahydro-3H-pyrazolo[4,3-c]pyridin-3-one;

4-{[2-(2-methoxybenzyl)-3-oxo-1,2,3,4,6,7-hexahydro-5H-pyrazolo[4,3-c]pyridin-5-yl]methyl}benzonitrile;

2-(4-chlorophenyl)-5-(pyridin-3-ylmethyl)-1,2,4,5,6,7-hexahydro-3H-pyrazolo[4,3-c]pyridin-3-one;

3-[3-oxo-5-(pyridin-3-ylmethyl)-1,3,4,5,6,7-hexahydro-2H-pyrazolo[4,3-c]pyridin-2-yl]benzonitrile;

4-{[3-oxo-2-(2-piperidin-1-ylethyl)-1,2,3,4,6,7-hexahydro-5H-pyrazolo[4,3-c]pyridin-5-yl]methyl}benzonitrile;

N-{3-[3-oxo-5-(pyridin-3-ylmethyl)-1,3,4,5,6,7-hexahydro-2H-pyrazolo[4,3-c]pyridin-2-yl]phenyl}acetamide;

2-(2-fluorophenyl)-5-(pyridin-3-ylmethyl)-1,2,4,5,6,7-hexahydro-3H-pyrazolo[4,3-c]pyridin-3-one;

4-{[2-(2-fluorophenyl)-3-oxo-1,2,3,4,6,7-hexahydro-5H-pyrazolo[4,3-c]pyridin-5-yl]methyl}benzonitrile;

5-[(6-chloropyridin-3-yl)methyl]-2-(2-methoxyethyl)-1,2,4,5,6,7-hexahydro-3H-pyrazolo[4,3-c]pyridin-3-one;

N-{3-[5-(3-chloro-4-fluorobenzyl)-3-oxo-1,3,4,5,6,7-hexahydro-2H-pyrazolo[4,3-c]pyridin-2-yl]phenyl}acetamide;

4-{[2-(4-methoxybenzyl)-3-oxo-1,2,3,4,6,7-hexahydro-5H-pyrazolo[4,3-c]pyridin-5-yl]methyl}benzonitrile;

5-(4-chlorobenzyl)-2-methyl-3a-(pyridin-3-ylmethyl)-2,3a,4,5,6,7-hexahydro-3H-pyrazolo[4,3-c]pyridin-3-one;

2-(2-methyl-1,3-benzothiazol-6-yl)-5-[3-(trifluoromethyl)benzyl]-1,2,4,5,6,7-hexahydro-3H-pyrazolo[4,3-c]pyridin-3-one;

5-(3-chloro-4-fluorobenzyl)-2-(4-chlorophenyl)-1,2,4,5,6,7-hexahydro-3H-pyrazolo[4,3-c]pyridin-3-one;

3-[5-(3-chloro-4-fluorobenzyl)-3-oxo-1,3,4,5,6,7-hexahydro-2H-pyrazolo[4,3-c]pyridin-2-yl]benzonitrile;

3-{3-oxo-5-[3-(trifluoromethyl)benzyl]-1,3,4,5,6,7-hexahydro-2H-pyrazolo[4,3-c]pyridin-2-yl}benzonitrile;

3-{5-[(6-chloropyridin-3-yl)methyl]-3-oxo-1,3,4,5,6,7-hexahydro-2H-pyrazolo[4,3-c]pyridin-2-yl}benzonitrile;

2-benzyl-5-(3-chloro-4-fluorobenzyl)-1,2,4,5,6,7-hexahydro-3H-pyrazolo[4,3-c]pyridin-3-one;

2-(4-chlorophenyl)-5-[(6-chloropyridin-3-yl)methyl]-1,2,4,5,6,7-hexahydro-3H-pyrazolo[4,3-c]pyridin-3-one;

5-[(6-chloropyridin-3-yl)methyl]-2-(2-fluorophenyl)-1,2,4,5,6,7-hexahydro-3H-pyrazolo[4,3-c]pyridin-3-one;

5-[(6-chloropyridin-3-yl)methyl]-2-(1-methylpiperidin-4-yl)-1,2,4,5,6,7-hexahydro-3H-pyrazolo[4,3-c]pyridin-3-one;

2-benzyl-5-[(6-chloropyridin-3-yl)methyl]-1,2,4,5,6,7-hexahydro-3H-pyrazolo[4,3-c]pyridin-3-one;

4-{5-[(6-chloropyridin-3-yl)methyl]-3-oxo-1,3,4,5,6,7-hexahydro-2H-pyrazolo[4,3-c]pyridin-2-yl}benzonitrile;

2-benzyl-5-(pyridin-3-ylmethyl)-1,2,4,5,6,7-hexahydro-3H-pyrazolo[4,3-c]pyridin-3-one;

2-(2-methyl-1,3-benzothiazol-6-yl)-5-(pyridin-2-ylmethyl)-1,2,4,5,6,7-hexahydro-3H-pyrazolo[4,3-c]pyridin-3-one;

5-(2-chlorobenzyl)-2-(2-methyl-1,3-benzothiazol-6-yl)-1,2,4,5,6,7-hexahydro-3H-pyrazolo[4,3-c]pyridin-3-one;

2-benzyl-5-(methylsulfonyl)-1,2,4,5,6,7-hexahydro-3H-pyrazolo[4,3-c]pyridin-3-one; and 2-(imidazo[1,2-a]pyridin-2-ylmethyl)-5-[(4-methylphenyl)sulfonyl]-1,2,4,5,6,7-hexahydro-3H-pyrazolo[4,3-c]pyridin-3-one.

* * * * *